United States Patent

Binet et al.

[11] Patent Number: 5,872,115
[45] Date of Patent: Feb. 16, 1999

[54] 2-UREIDO-BENZAMIDE DERIVATIVES

[75] Inventors: Jean Binet; Christian Guffroy, both of Fontaine-lés-Dijon, France; Hirotaka Kasai, Kokubuniji; Nagatoshi Wagatsuma, Kawasaki, both of Japan

[73] Assignees: Grelan Pharmaceutical Co. Ltd., Tokyo, Japan; Laboratoires Fournier S.C.A., Dijon, France

[21] Appl. No.: 765,314
[22] PCT Filed: Apr. 27, 1996
[86] PCT No.: PCT/EP96/01886
    § 371 Date: Dec. 30, 1996
    § 102(e) Date: Dec. 30, 1996
[87] PCT Pub. No.: WO96/34856
    PCT Pub. Date: Nov. 7, 1996

[30] Foreign Application Priority Data

May 5, 1995 [EP] European Pat. Off. .............. 95401049

[51] Int. Cl.⁶ .................. A61K 31/55; A61K 31/445; A61K 31/535; C07D 267/18; C07D 413/10; C07D 401/10
[52] U.S. Cl. .................. 514/211; 514/212; 514/281; 514/235.5; 514/235.8; 514/317; 514/318; 514/326; 514/331; 514/596; 514/597; 540/544; 540/575; 544/129; 544/141; 544/359; 544/372; 544/391; 546/208; 546/231; 546/48; 546/51; 564/48; 564/51
[58] Field of Search .................. 514/211, 212, 514/218, 255, 317, 326, 331, 596, 597, 235.5, 235.8, 397; 540/544, 575; 544/129, 141, 359, 372, 391; 546/208, 231; 564/48, 51

[56] References Cited

U.S. PATENT DOCUMENTS

| | | | |
|---|---|---|---|
| 3,646,136 | 2/1972 | Hoegerle et al. | 564/231 |
| 3,812,168 | 5/1974 | Hoegerle et al. | 514/596 |
| 4,623,662 | 11/1986 | De Vries | 514/596 |
| 4,923,896 | 5/1990 | Trivedi | 514/507 |
| 5,015,644 | 5/1991 | Roth et al. | 514/247 |
| 5,106,873 | 4/1992 | O'Brien et al. | 514/596 |
| 5,116,848 | 5/1992 | Trivedi | 514/332 |

FOREIGN PATENT DOCUMENTS

| | | |
|---|---|---|
| 0105196 | 4/1984 | European Pat. Off. . |
| 0235878 | 9/1987 | European Pat. Off. . |
| 0335374 | 10/1989 | European Pat. Off. . |
| 0335375 | 10/1989 | European Pat. Off. . |
| 0477778 | 4/1992 | European Pat. Off. . |
| 0370740 | 7/1992 | European Pat. Off. . |
| 0405233 | 10/1993 | European Pat. Off. . |
| 0447116 | 12/1994 | European Pat. Off. . |
| 56-73054 | of 1981 | Japan . |
| 59-181257 | 10/1984 | Japan . |

OTHER PUBLICATIONS

CA 96:34910, 1981.
Journal of Lipid Research —vol. 26, 1985 "Role of Acyl–CoA: cholesterol acyltransferase . . . " (pp. 647–671).
European Journal of Clinical Investigation (1979) Esterification of Cholesteral in Human Small Intestine . . . pp. 55–62.
The Enzymes, vol. XVI "Acyl Coenzyme A: Cholesterol O–Acyltransferase" pp. 523–539, 1983.
Journal of Medicinal Chemistry, vol. 36, No.11, 1993 pp. 1641–1653.

(List continued on next page.)

*Primary Examiner*—Yogendra N. Gupta
*Attorney, Agent, or Firm*—Ladas & Parry

[57] ABSTRACT

This invention is concerned with 2-ureido-benzamide compounds of the formula (1)

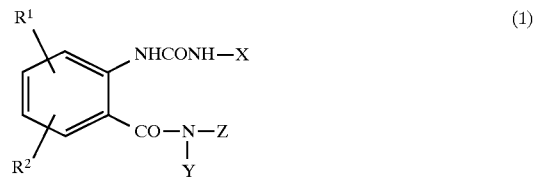

in which $R^1$ is H, halogen atom, $(C_1–C_4)$alkyl, $(C_1–C_4)$alkoxy or $(C_1–C_4)$dialkylamino and $R^2$ is H, halogen atom, hydroxy, nitro, $(C_1–C_4)$alkyl, $(C_1–C_4)$alkoxy, $(C_3–C_6)$ cycloalkylmethoxy, $(C_1–C_4)$ alkylthio, $(C_1–C_4)$ alkylsulfinyl, $(C_1–C_4)$alkylsulfonyl or

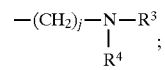

wherein j is an integer of from 0 to 2 and $R^3$ and $R^4$ are each independently H, $(C_1–C_4)$alkyl, $(C_1–C_4)$alkanoyl, $(C_1–C_4)$alkylsulfonyl or $(C_1–C_4)$alkylcarbamoyl, $NR^3R^4$ can to form a pyrrolidine, piperidine, morpholine, imidazole or pyrazole ring;

X is a $(C_3–C_{15})$alkyl, $(C_3–C_6)$ cycloalkyl, $(C_3–C_6)$ cycloalkylmethyl, ω-$(C_1–C_4)$ alkoxy-$(C_1–C_4)$ alkyl group or

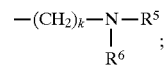

wherein k is an integer of from 1 to 4 and $R^5$ and $R^6$ are each independently H,
Y is H or $(C_1–C_4)$alkyl and Z is

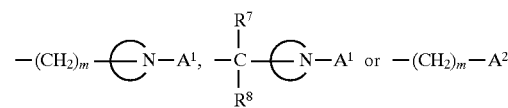

wherein m is an integer of from 0 to 4.

26 Claims, No Drawings

OTHER PUBLICATIONS

Patent Abstracts of Japan vol.9, No. 36 (C–266), 15 Feb.1985 & JP,A,59 181257 (Chugai Seiyaku K.K.), 15 Oct. 1984.

Indian Journal of Chemistry, vol.26b, No. 12, 1987, pp. 1133–1139, XP000196273 B.P. Acharya et al: "Structure of the . . . ".

Monatshefte Fur Chemie, vol. 98, No. 3, 1967, pp. 633–642, XP000578294 W. Metlesics et al.: "Chinazoline und 1,4–Benzodiazepine . . . ".

2-UREIDO-BENZAMIDE DERIVATIVES

BACKGROUND OF THE INVENTION

1. Field of the Invention

The present invention relates to novel 2-ureido-benzamide derivatives having potent acyl coenzyme A:cholesterol acyltransferase (ACAT: EC2.3.1.26) inhibiting activity, to pharmaceutical composition containing these compounds and to use thereof for the treatment and prevention of atherosclerosis.

Ischemic circulatory diseases such as myocardial infarction and cerebral infarction resulting from atherosclerosis have been a major cause of human death. The studies on atherosclerosis have been carried out in the various fields for long years.

Recently, it has been found that esterification of intracellular cholesterol is effectively catalyzed by the enzyme: ACAT which is found later in various tissues such as liver, intestine, adrenal and macrophages. It is said that ACAT may be present in all tissues [The Enzymes, 16, 523–539 (1983)].

In intestine, ACAT plays a key role in the gastrointestinal absorption of cholesterol. In intestinal mucosal cells, dietary and biliary cholesterol derived from the diet and biosynthesis must be esterified by the action of ACAT before it can be incorporated into the chyromicron particles which are then released into the blood stream [Eur. J. Clin. Invest., 9, 55 (1971)]. Thus inhibition of ACAT in intestinal mucosa appears to block intestinal absorption of cholesterol, resulting in the decrease of blood cholesterol level. However, such an intestinal ACAT inhibitor may involve unfavorable increase of the endogenous cholesterol synthesis and possible ineffectiveness of such inhibitor on patients having no hyper-function in cholesterol absorption.

Although the role of ACAT in liver, especially in human, is less clearly known, the ACAT may participate in the synthesis and secretion of VLDL and the control of biliary excretion of cholesterol [J. Lipid Res., 26, 647 (1985)] and inhibition of the liver ACAT may result in lowering of the blood lipid level.

Cholesterol esters are a major component of atherosclerotic lesions and also a major storage form of cholesterol in arterial wall cells. Accumulation of cholesterol esters is linked to the form cell formation which is catalyzed by ACAT in macrophages. Thus, inhibition of the macrophage ACAT may prevent directly the progression of atherosclerotic lesion formation by decreasing the form cell formation without unfavorable effects as in the case of ACAT inhibition in intestine.

2. Description of the Prior Art

Certain phenylurea derivatives having ACAT inhibiting activity are disclosed as shown below.

(a) U.S. Pat. No. 4,623,662 (1986) discloses substituted urea and thiourea compounds such as

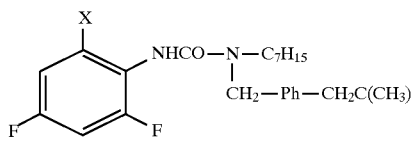

(b) EP Publication No. 477,778 (1992) and J. Med. Chem., 36, No. 11, 1641–1653 (1993) disclose benzene, pyridine and pyrimidine derivatives such as

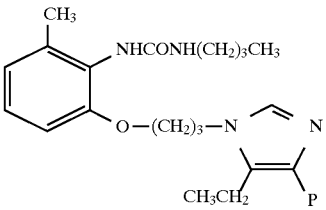

(c) EP Publication No. 370,740 (1990) discloses diaryl compounds as inhibitors of ACAT such as

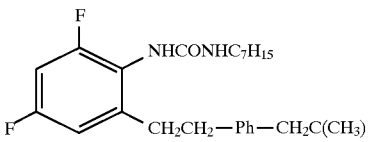

(d) U.S. Pat. No. 5,116,848 (1992) discloses N-phenylalkyl(thio)urea derivatives such as

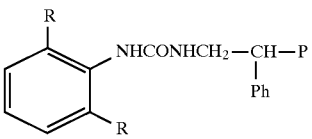

(e) A variety of urea compounds can be found in the other literatures, for example, in EP Publication Nos. 335,375 (1989), 405,233 (1991) and 447,116 (1991) and in U.S. Pat. Nos. 4,923,896 (1990), 5,015,644 (1991) and 5,106,873 (1992).

On the other hand, phenylurea derivatives having other pharmacological or agricultural activities such as blood sugar lowing activity, 5-HT M-receptor antagonist activity and herbicidal activity are disclosed in JP Unexamined Publication No. 59-181,257 (1984) [Chem. Abst., 102, No. 78735 (1985)], EP Publication No. 235,878 (1987) and U.S. Pat. No. 3,812,168 (1974), respectively. And some organic reactions for phenylurea derivatives are disclosed in literatures such as Indian J. Chem., 266 No. 12, 1133–1139 (1987) and Mh. Chem., 98, No. 3, 633–642 (1967).

However, there are no known literature references disclosing such 2-ureido-benzamide derivatives as those in this invention and their use as ACAT inhibitors for the treatment of atherosclerosis.

The present inventors synthesized various novel 2-ureido-benzamide compounds having substituents on both of amide and urea(ureido) nitrogen atoms and intensively investigated their activities, and, as the result, found that the useful as a drug for atherosclerosis and related diseases.

SUMMARY OF THE INVENTION

The present invention provides (i) a novel 2-ureido-benzamide derivative of the formula (1)

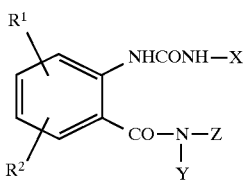 (1)

in which $R^1$ is H, halogen atom, $(C_1-C_4)$ alkyl, $(C_1-C_4)$ alkoxy or $(C_1-C_4)$ dialkylamino and $R^2$ is H, halogen atom, hydroxy, nitro, $(C_1-C_4)$ alkyl, $(C_1-C_4)$ alkoxy, $(C_3-C_6)$ cycloalkylmethoxy, $(C_1-C_4)$ alkylthio, $(C_1-C_4)$ alkylsulfinyl, $(C_1-C_4)$ alkylsulfonyl or

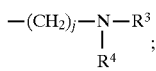

wherein j is an integer of from 0 to 2 and $R^3$ and $R^4$ are each independently H, $(C_1-C_4)$ alkyl, $(C_1-C_4)$ alkanoyl, $(C_1-C_4)$ alkylsulfonyl or $(C_1-C_4)$ alkylcarbamoyl, or $NR^3R^4$ can form a pyrrolidine, piperidine, morpholine, imidazole or pyrazole ring;

X is a $(C_3-C_{15})$ alkyl, $(C_3-C_6)$ cycloalkyl, $(C_3-C_6)$, cycloalkylmethyl, $\omega$-$(C_1-C_4)$ alkoxy-$(C_1-C_4)$ alkyl group or

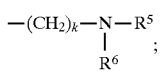

wherein k is an integer of from 1 to 4 and $R^5$ and $R^6$ are each independently H, $(C_1-C_6)$ alkyl or $(C_1-C_4)$ alkoxycarbonyl; and Y is H or $(C_1-C_4)$ alkyl and Z is

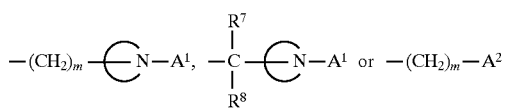

wherein m is an integer of from 0 to 4,

is a pyrrolidinyl or piperidyl ring and $A^1$ is a phenyl, benzyl, diphenylmethyl, pyridyl, dibenzoxepinyl, phenoxycarbonyl or biphenylmethyl group optionally carrying halogen atom, hydroxy, $(C_1-C_7)$ alkyl, $(C_1-C_4)$ alkoxy, $(C_1-C_4)$ alkoxymethyl, phenyl or halogenophenyl, and $A^2$ is a phenyl, benzyl, diphenylmethyl, dibenzoxepinyl or phenoxycarbonyl group optionally carrying halogen atom, hydroxy, $(C_1-C_7)$ alkyl, $(C_1-C_4)$ alkoxy, $(C_1-C_4)$ alkoxymethyl, phenyl or halogenophenyl, and $R^7$ is H or $(C_1-C_4)$ alkyl and $R^8$ is $(C_1-C_4)$ alkyl or $CR^7R^8$ can form a cyclopentyl, cyclohexyl or cycloheptyl ring; or —NYZ can form a ring

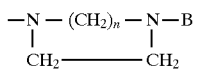

wherein n is an integer of from 1 to 3 and B is a phenyl, diphenylmethyl or dibenzocycloheptenyl group optionally carrying halogen atom or $(C_1-C_4)$ alkoxy;

and pharmaceutically acceptable acid addition salts thereof, having excellent ACAT inhibiting activity;

(ii) an ACAT inhibitor composition which contains anyone of the compounds of the formula (1) and the use of said compounds as ACAT inhibitors; and (iii) a method of producing the compounds of formula (1).

DETAILED DESCRIPTION

This invention relates to the compound of formula (1). Referring to the formula (1), the term "halogen" is fluorine (F), chlorine (Cl) or bromine (Br) and the terms "alkyl", "alkoxy" and "alkanoyl" mean straight- and branched-chain alkyl, alkoxy and alkanoyl, respectively. For example, $(C_1-C_4)$ alkyl is methyl, ethyl, n- or iso-propyl, n-, iso-, sec- or tert-butyl; $(C_1-C_4)$ alkylthio, $(C_1-C_4)$alkylsulfinyl, $(C_1-C_4)$ alkylsulfonyl and $(C_1-C_4)$ alkylcarbonyl are thio, sulfinyl, sulfonyl and carbonyl substituted by such $(C_1-C_4)$ alkyl, respectively; $(C_1-C_4)$ alkoxy is methoxy, ethoxy, n- or iso-propoxy or n-, iso-, sec- or tert-butoxy; $(C_1-C_4)$ alkoxycarbonyl is carbonyl substituted by such $(C_1-C_4)$ alkoxy; and $(C_1-C_4)$ alkanoyl is acetyl, propionyl or n- or iso-butyryl. Alkyl higher than $C_4$ such as $(C_5-C_{15})$ alkyl may be represented by pentyl $(C_5)$, hexyl$(C_6)$, heptyl $(C_7)$, octyl $(C_8)$, nonyl $(C_9)$, decyl $(C_{10})$, undecyl $(C_{11})$, dodecyl $(C_{12})$, tridecyl $(C_{13})$, tetradecyl $(C_{14})$, pentadecyl $(C_{15})$ and their branched-chain form. Furthermore, referring to the formula (1), the term <<$(C_3-C_6)$>> means cyclopropyl, cyclobutyl, cyclopentyl or cyclohexyl.

As mentioned hereinabove, $A^1$ is a phenyl, benzyl, diphenylmethyl, pyridyl, dibenzoxepinyl, phenoxycarbonyl or biphenylmethyl group which is optionally substituted by one (preferably) or several substituents such as halogen, hydroxy, $(C_1-C_7)$ alkyl, $(C_1-C_4)$ alkoxy, $(C_1-C_4)$ alkoxymethyl, phenyl or halogenophenyl; in a similar manner, $A^2$ is a phenyl, benzyl, diphenylmethyl, dibenzoxepinyl or phenoxycarbonyl group which is optionally substituted by one (preferably) or several substituents such as halogen, hydroxy, $(C_1-C_7)$ alkyl, $(C_1-C_4)$ alkoxy, $(C_1-C_4)$ alkoxymethyl, phenyl or halogenophenyl.

Preferred embodiments of this invention represented by the formula (1), in view of such as the ACAT inhibiting properties, exhibit one or more of the following features: (a) $R^1$ is H and $R^2$ is H, di-substituted amino group or morpholino group; (b) X is $(C_3-C_{10})$ alkyl, more preferably, $(C_3-C_8)$ alkyl; and/or (c) Y is H and Z is a (N-aralkyl) aminoalkyl group such as a (N-diphenylmethyl) piperidyl group with or without intermediary alkylene chain between the nitrogen atom of the amide and the piperidyl ring; or Y and Z considered together with the N atom to which they are bonded are combined to form a ring such as the (N-diphenylmethyl)piperazinyl ring.

Preferred example of the compounds (1) includes:

2-(N'-n-heptylureido)-5-dimethylamino-N-[(1-diphenylmethylpiperidin-4-yl)methyl]-benzamide;

2-(N'-n-butylureido)-N-[(1-diphenylmethylpiperidin-4-yl)methyl]benzamide;

2-(N'-n-pentylureido)-N-[(1-diphenylmethylpiperidin-4-yl)methyl]benzamide;

2-(N'-n-hexylureido)-N-[(1-diphenylmethylpiperidin-4-yl)methyl]benzamide;

2-(N'-n-heptylureido)-N-[(1-diphenylmethylpiperidin-4-yl)methyl]benzamide;

2-(N'-n-octylureido)-N-[(1-diphenylmethylpiperidin-4-yl)methyl]benzamide;

2-(N'-n-butylureido)-N-(1-diphenylmethylpiperidin-4-yl)benzamide;

2-(N'-n-hexylureido)-N-(1-diphenylmethylpiperidin-4-yl)benzamide;
2-(N'-n-octylureido)-N-(1-diphenylmethylpiperidin-4-yl)benzamide;
2-(N'-n-decylureido)-N-(1-diphenylmethylpiperidin-4-yl)benzamide;
2-(N'-n-heptylureido)-N-(1-phenoxycarbonylpiperidin-4-yl)benzamide;
2-(N'-n-heptylureido)-5-hydroxy-N-(3,3-diphenylpropyl)benzamide;
2-(N'-n-heptylureido)-N-[2-(1-diphenylmethylpiperidin-4-yl)ethyl]benzamide;
2-(N'-n-pentylureido)-N-[2-(1-diphenylmethylpiperidin-4-yl)ethyl]benzamide;
2-(N'-n-hexylureido)-N-[2-(1-diphenylmethylpiperidin-4-yl)ethyl]benzamide;
2-(N'-n-heptylureido)-5-dimethylamino-N-(1-diphenylmethylpiperidin-4-yl)benzamide;
1-[2-N'-n-heptylureido)benzoyl]-4-diphenylmethylhomopiperazine;
1-[2-(N'-n-heptylureido)benzoyl]-4-(10,11-dihydro-5H-dibenzo[a,d]cyclohepten-5-yl)-piperazine;
2-(N'-n-heptylureido)-N-(1-diphenylmethylpiperidin-4-yl)benzamide;
N-(2-bromo-6,11-dihydrodibenz[b,e]oxepin-11-yl)methyl-2-(N'-n-heptylureido)benzmide;
2-(N'-n-heptylureido)-5-acetylamino-N-(1-diphenylmethylpiperidin-4-yl)benzamide;
N-(3,3-diphenylpropyl)-2-(N'-n-heptylureido)benzamide;
1-[2-(N'-n-heptylureido)benzoyl]-4-diphenylmethylpiperazine;
2-(N'-n-butylureido)-5-diethylamino-N-[(1-diphenylmethylpiperidin-4-yl)-methyl]benzamide;
2-(N'-n-butylureido)-5-dimethylamino-N-[(1-diphenylmethylpiperidin-4-yl)methyl]benzamide;
2-(N'-n-butylureido)-5-(pyrrolidin-1-yl)-N-[(1-diphenylmethylpiperidin-4-yl)methyl]-benzamide;
5-dimethylamino-2-(N'-n-propylureido)-N-[(1-diphenylmethylpiperidin-4-yl)methyl]-benzamide;
2-(N'-butylureido)-5-methoxy-N-[(1-diphenylmethylpiperidin-4-yl)methyl]-benzamide;
2-(N'-n-butylureido)-5-ethoxy-N-[(1-diphenylmethylpiperidin-4-yl)methyl]-benzamide;
2-(N'-n-butylureido)-5-cyclopropylmethoxy-N-[(1-diphenylmethylpiperidin-4-yl)methyl]-benzamide;
2-(N'-n-butylureido)-5-(morpholin-4-yl)-N-[(1-diphenylmethylpiperidin-4-yl)methyl]-benzamide;
5-(morpholin-4-yl)-2-(N'-n-propylureido)-N-[(1-diphenylmethylpiperidin-4-yl)methyl]-benzamide;
2-(N'-n-butylureido)-5-methylthio-N-[(1-diphenylmethylpiperidin-4-yl)methyl]benzamide;
5-n-butylcarbamyloxy-2-(N'-n-butylureido)-N-[(1-diphenylmethylpiperidin-4-yl)methyl]-benzamide;
2-(N'-n-heptylureido)-5-methoxy-N-[(1-diphenylmethylpiperidin-4-yl)methyl]-benzamide;
2-(N'-n-heptylureido)-5-(morpholin-4-yl)-N-[(1-diphenylmethylpiperidin-4-yl)methyl]-benzamide;
2-(N'-n-heptylureido)-5-(pyrazol-1-yl)-N-[(1-diphenylmethylpiperidin-4-yl)methyl]benzamide;
2-(N'-n-heptylureido)-5-(pyrrolidin-1-yl)-N-[(1-diphenylmethylpiperidin-4-yl)methyl]-benzamide;
5-ethoxy-2-(N'-n-heptylureido)-N-[(1-diphenylmethylpiperidin-4-yl)methyl]-benzamide;
2-(N'-n-heptylureido)-5-dimethylamino-N-[(1-diphenylmethylpiperidin-3-yl)methyl]-benzamide;
5-(N-acetyl-N-methyl)amino-2-(N'-n-heptylureido)-N-[(1-diphenylmethylpiperidin-4-yl)-methyl]benzamide;
2-(N'-n-heptylureido)-5-dimetyhylamino-N-[[1-bis(4-fluorophenyl)methylpiperidin-4-yl]-methyl]benzamide;
2-(N'-n-heptylureido)-5-dimethylamino-N-[[1-bis(4-methoxyphenyl)methylpiperidin-4-yl]-methyl]benzamide;
2-(N'-n-heptylureido)-5-dimethylamino-N-[1-(2-biphenylmethylpiperidin-4-yl)methyl]-benzamide;
5-dimethylamino-2-(N'-n-pentylureido)-N-[(1-diphenylmethylpiperidin-4-yl)methyl]benzamide;
2-(N'-3-methoxypropylureido)-5-dimethylamino-N-[(1-diphenylmethylpiperidin-4-yl)-methyl]benzamide;
2-(N'-3-methoxypropylureido)-5-(morpholin-4-yl)-N-[(1-diphenylmethylpiperidin-4-yl)-methyl]benzamide;
2-(N'-cyclopropylmethylureido)-5-(morpholin-4-yl)-N-[(1-diphenylmethylpiperidin-4-yl)-methyl]benzamide;
2-(N'-n-butylureido)-5-methylsulfinyl-N-[(1-diphenylmethylpiperidin-4-yl)methyl]benzamide;
2-(N'-n-butylureido)-5-methylsulfonyl-N-[(1-diphenylmethylpiperidin-4-yl)methyl]benzamide;

The above compounds (1) may be in the form of their pharmaceutical acceptable acid addition salts which are included within the scope of this invention. Preferred example of the salts include non-toxic salts with inorganic and organic acids, such as hydrochloric, hydrobromic, sulfuric, phosphoric, acetic, lactic, tartaric, citric, fumaric, malic, maleic, succinic, methanesulfonic, benzenesulfonic and p-toluenesulfonic acids. Preparation of the salts can be carried out in accordance with well known techniques for forming salts.

This invention also relates to a method of or use for reducing the cholesterol content of the arterial walls and treating atherosclerosis and related diseases of mammals which comprises administrating to said mammals an effective amount of a compound as recited above. The compounds (1) have potent ACAT inhibiting activity with weak toxicity as shown in the following test example. ACAT catalyzes the esterification of cholesterol with higher fatty acids and it plays an important role in the absorption of cholesterol and in the intracellular accumulation of cholesterol esters. ACAT inhibitor can reduce absorption of dietary cholesterol and intracellular cholesterol ester accumulation in the arterial wall, thereby, lowering the blood cholesterol level with retarding the build-up of atherosclerotic lesions. Accordingly, the compounds (1) of this invention are useful as safe prophylactic and therapeutic agents for hypercholesterolemia, atherosclerosis and diseases resulting from these (e.g. ischemic heart diseases such as myocardial infarction, cerebrovascular diseases such as cerebral infarction and cerebral apoplexy) in mammals (e.g. mouse, rat, rabbit, dog, monkey, human).

This invention further relates to pharmaceutical compositions which comprise an effective anti-atherosclerotic amount of a compound as recited above. For prophylactic or therapeutic use vis-a-vis the above diseases, the compounds of formula (1) are preferably presented with pharmaceutically acceptable appropriate carriers, excipients or diluents as pharmaceutical formulations such as powders, granules, tablets, capsules or injectable solutions, which can be prepared by any of the well known techniques of pharmacy and administered either orally or non-orally.

For the purpose of inhibiting cholesterol absorption or accumulation, the oral route of administration may be preferred. The amount of a compound of formula (1) which is required to achieve the desired biological effect will, of course, depend on the kind of compound (1), the mode of administration, the clinical condition and age of the recipient and the other factors. In general, a daily dose per kilogram of body weight is expected to lie in the range of from 10 μg to 100 mg, typically from 50 μg to 50 mg, and such daily dose is preferably administrated as a single dose or in two or three divided doses.

This invention still further relates to process for preparing compounds as recited above.

Preparation Process for the Compound (1)

There are several alternate approaches to the preparation of the compounds in this invention.

A. Synthesis of the 2-ureido-benzamides. 2-Ureido-benzamide derivatives of the formula (1) can be prepared by, for instance, the following processes which are outlined in Reaction Scheme I.

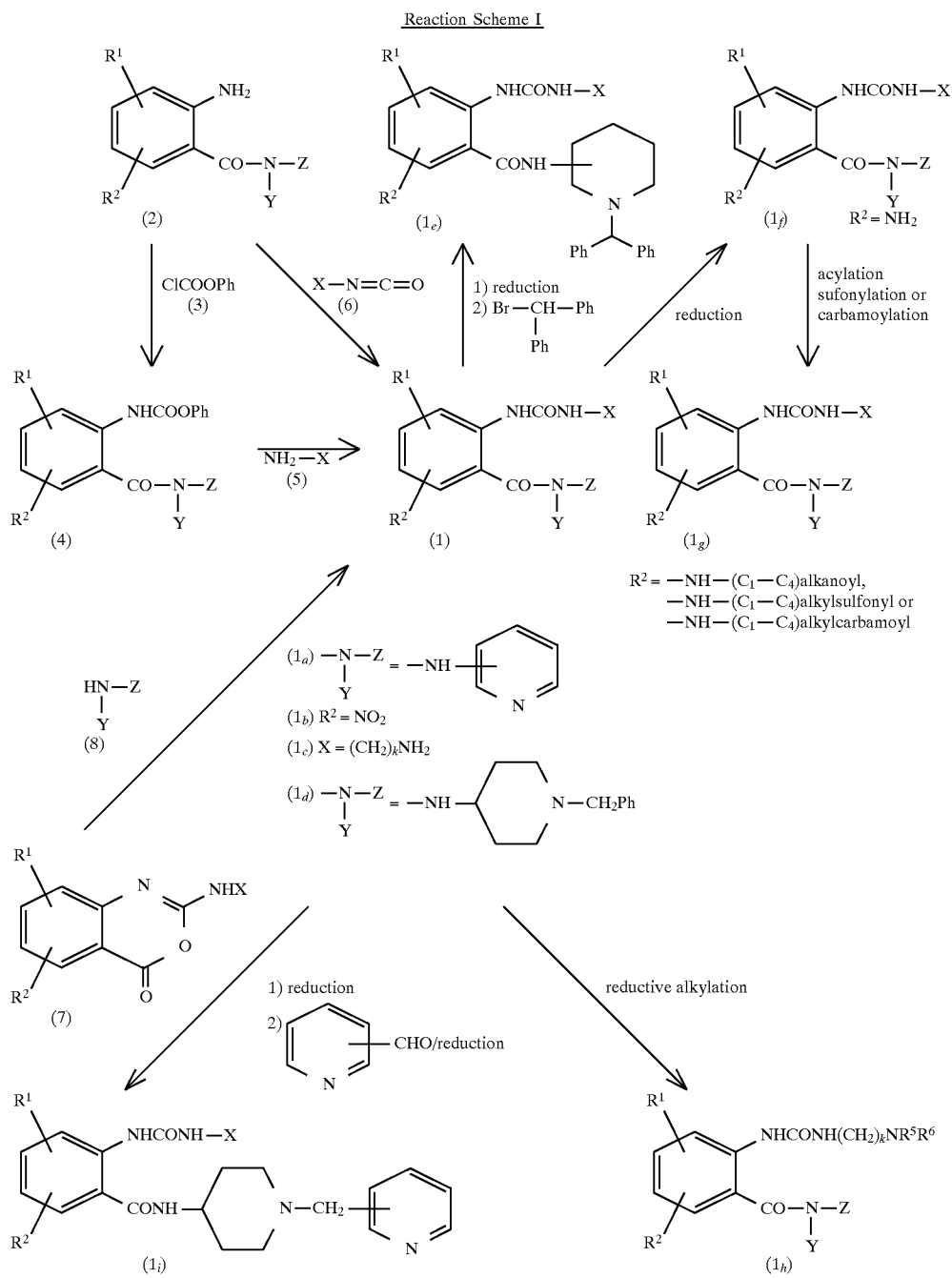

Reaction Scheme I (The Symbols in the above formula are as defined hereinabove and phenyl and pyridyl ring may be optionally substituted as defined hereinabove).

A1) The reaction of the 2-amino-benzamide (2) with formic acid ester halide such as phenylchloroformate (3) is generally carried out in a solvent in the presence of a base. A suitable base, may be for instance an organic base such as pyridine, triethylamine, picoline, 4-dimethylaminopyridine and N,N-diethylaniline and an inorganic base such as potassium carbonate. Among the suitable solvent are used any inert solvent to the reaction, for instance, benzene, toluene, chloroform and dichloromethane. The reaction is generally conducted at an appropriate temperature of −20° C. to the boiling point of the solvent which is used. The 2-phenoxycarbonylamino-benzamide (4) thus obtained is reacted with the amine (5) to give 2-ureido-benzamide (1). The reaction is generally carried out in an appropriate solvent such as benzene, toluene, chloroform and dichloromethane. The amine (5) may be prepared by a known method, for example, by the processes described by C. A. Buecheler et. al. in Survey of Organic Synthesis, 394–459 (1977) or modifications thereof.

A2) Alternatively, the 2-ureido-benzamide (1) can be prepared by reacting 2-amino-benzamide (2) with the isocyanate (6). This reaction is conducted in the absence of a solvent or in an inert solvent such as ethyl acetate, dichloromethane, chloroform, tetrahydrofuran, acetonitrile, benzene, toluene and N,N-dimethylformamide. The reaction temperature is generally comprised between room temperature and the refluxing temperature of the solvent which is used. In the absence of a solvent, this reaction can be carried out by heating the 2-amino-benzamide (2) with the isocyanate (6) directly at 90°–250° C. The isocyanate (6) is obtained by reacting the corresponding carboxylic acid with an azide compound such as diphenylphosphoryl azide in the presence of a tertiary amine such as triethylamine, pyridine and picoline in an appropriate solvent such as acetonitrile and chloroform.

A3) Further, the compound (1) can be prepared by reacting the benzoxazin (7) with the amine (8) in an appropriate solvent such as benzene, toluene, N,N-dimethylformamide, acetonitrile and chloroform. The temperature is generally comprised between room temperature and the boiling point of the solvent which is used. The benzoxazin (7) may be obtained by a known method [e.g. J. Heterocyclic Chemistry, 19, 267 (1982) and EP Patent No. 147,211 (1985)] or its modified method. The amine (8) is commercially available or readily prepared by a known method described for instance in U.S. Pat. No. 4,267,318 or a modification thereof.

B. Conversion of the 2-ureido-benzamides. Certain compounds of 2-ureido-benzamide derivatives of the formula (1) prepared by the above mentioned processes A1), 2) and 3) are then further converted to the another 2-ureido-benzamide derivatives. For example, the compounds described as structures ($1_a$), ($1_b$), ($1_c$) and ($1_d$) are successfully converted to the objective 2-ureido-benzamide derivatives of the formulae ($1_e$), ($1_f$), ($1_g$), ($1_h$) and ($1_i$) by the following processes which are also outlined in Reaction Scheme I.

B1) The N-pyridyl-2-ureido-benzamide ($1_a$) can be reduced to the corresponding N-piperidyl compound and then reacted with diphenylmethyl halide such as bromodiphenylmethane in the presence of a base such as potassium carbonate in a solvent such as dimethyl sulfoxide to give the N-(N-diphenylmethyl)piperidyl-2-ureido-benzamide ($1_e$). The reduction can be effectively performed by catalytic reduction using an appropriate catalyst such as platinum and platinum oxide under hydrogen atmosphere at an appropriate pressure of 20–100 psi in a solvent such as acetic acid.

B2) The 5-amino-2-ureido-benzamide ($1_f$) may be prepared by reducing 5-nitro-2-ureido-benzamide ($1_b$). This reaction can be conducted in the manner of catalytic reduction using appropriate catalyst or can be conducted in the presence of a reducing agent. As such catalyst, there may be mentioned, for example, palladium on charcoal, platinum on charcoal and Raney nickel. As examples of said reducing agent is metal (e.g. zinc, iron and tin) in an acid such as hydrochloric acid, acetic acid and aqueous sulfuric acid. The reduction is generally carried out under hydrogen atmosphere at an appropriate pressure of ambient to 5 kg/cm$^2$ in a solvent such as methanol, ethanol, acetic acid and ethyl acetate at an appropriate temperature of room temperature to 100° C. The reaction using the reducing agent is generally carried out in the similar manner to a known method described for instance in J. Org. Chem., 31, 684(1966).

B3) Alternatively, 5-amino-2-ureido-benzamide ($1_f$) thus obtained may be converted to the formula ($1_g$). The compound ($1_f$) can be acylated with an acid anhydride such as acetic anhydride or an acid chloride such as acetyl chloride in the presence of an appropriate base in a solvent such as dichloromethane and chloroform. Useful as said base are cited organic bases, for instance, triethylamine, pyridine and N,N-diethylaniline. The reaction temperature is generally comprised between 0° C. and the boiling point of the solvent which is used.

Sulfonylating the compound ($1_f$) can be performed in the similar manner as the above mentioned acylating, but replacing acid anhydride or acid chloride with alkylsulfonyl chloride such as methanesulfonyl chloride.

The compound ($1_f$) can be converted to the 2,5-diureido-benzamide according to the similar manner as for the preparation process A2) by reacting with the corresponding isocyanate.

B4) 2-(N'-Alkylaminoalkylureido)-benzamide ($1_h$) may be prepared by reductive alkylation of the 2-(N'-aminoalkylureido)benzamide ($1_c$) with the corresponding carbonyl compound. The reaction can be carried out by the use of a reducing agent such as sodium cyanoborohydride, sodium borohydride or lithium cyanoborohydride in an appropriate solvent such as methanol, ethanol and ethyl ether at an appropriate temperature of from −20° C. to the boiling point of the solvent which is used.

B5) The benzyl group of the N-benzylpiperidyl-2-ureido-benzamide ($1_d$) is removed by reduction and the resulting N-piperidyl-2-ureido-benzamide may be reacted with the corresponding formyl pyridine in the presence of a reducing agent such as sodium cyanoborohydride to give the N-pyridylmethylpiperidyl-2-ureido-benzamide ($1_i$). The reduction of the compound ($1_d$) is generally performed by hydrogen over an appropriate catalyst such as palladium on charcoal.

C. Preparation of the intermediates: The 2-amino-benzamide (2) which is important as a starting compound for the preparation of the 2-ureido-benzamide (1) can be synthesized, for example, by the following processes outlined in Reaction Scheme II.

Reaction Scheme II

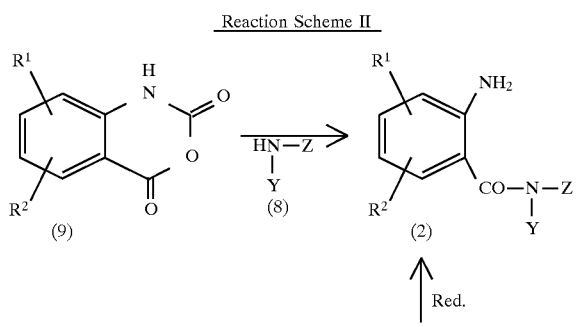

-continued
Reaction Scheme II

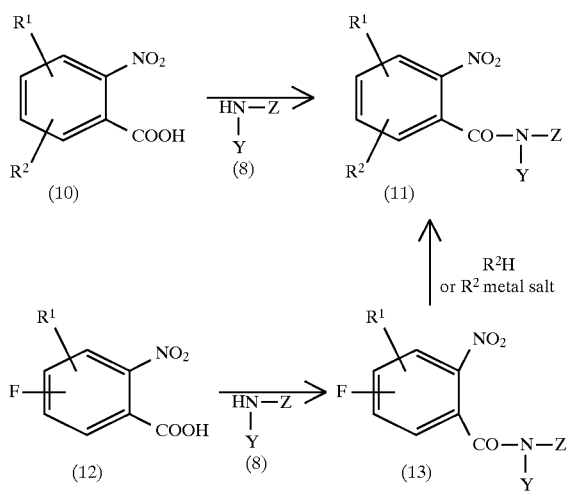

C1) 2-Amino-benzamide (2) can be prepared by reacting the isatoic anhydride (9) with the amine (8) in a solvent such as dichloromethane and chloroform at an appropriate temperature of from room temperature to the boiling point of the solvent which is used.

C2) The condensation reaction of the 2-nitrobenzoic acid (10) with the amine (8) can be carried out in the presence of a condensing agent in an inert solvent such as dichloromethane, chloroform and tetrahydrofurane at an appropriate temperature of from 0° C. to room temperature. The useful condensing agents are 1,3-dicyclohexyl-carbodiimide, N-ethyl-N'-(3-dimethylaminopropyl) carbodiimide and 1,1-carbonyl-diimidazole. The 2-nitrobenzamide (11) thus obtained is reacted with a reducing agent to give the 2-amino-benzamide (2). This reductive reaction can be conducted essentially in the same manner as the preparation process B2) mentioned above.

C3) The condensation of the 2-nitrobenzoic acid (12) with the amine (8) can be carried out in the presence of a condensing agent in the same manner as the preparation process C2) or by using thionyl chloride, compound (12) to convert into the acid chloride, followed by reacting with the amine (8). The fluorine substituent on 5-position of the 2-nitrobenzamide (13) thus obtained is substituted for other substituents by reacting with $R^2H$ (e.g. monomethylamine, dimethylamine, diethylamine, di-n-propylamine, di-n-butylamine, pyrrolidine, piperidine, morpholine, pyrazole, imidazole) or $R^2$ metal salt (e.g. sodium methoxide, sodium ethoxide, sodium thiomethoxide, sodium thioethoxide) in an inert solvent such as tetrahydrofuran, dioxane and N,N-dimethylformamide with or without a sealed tube at an appropriate temperature (from ambient to refluxed temperature). The 2-nitrobenzamide (11) thus obtained is reacted with reducing agents in the same manner as the preparation process B2) to give the aminobenzamide (2).

The desired compounds (1) thus obtained can be purified and recovered by using per se known separation or purification procedures (e.g. concentration, solvent extraction, column chromatography, recrystallization).

Activity

The following pharmacological test results indicate that the 2-ureido-benzamide derivatives (1) according to the inventions are of great utility.

1. Acyl-CoA:cholesterol Actyltransferase (ACAT) Inhibiting Activity

[Test Method]

(1) In-vitro Test Using Hep G2 Microsome

ACAT enzyme fraction was prepared from microsome of human derived hepatoma Hep G2 cell according to Sandra's method [Journal of Lipid Research, 27, 875 (1986)].

Microsome was suspended at a concentration of 200 μg protein/20 μl in 0.1M phosphate buffer solution (pH7.4) and the suspension was preincubated at 37° C. for 5 minutes after addition of 10 μl of each test compound dissolved in 0.1M phosphate buffer solution containing bovine serum albmin (BSA). Then, the reaction was initiated by the addition of 5 nmoles of labeled [$^{14}$C]-oleoyl-CoA dissolved in 20 μl of the said phosphate buffer solution containing BSA and the reaction was stopped by the addition of 20 μl of 2N HCl after 10 minutes. [$^{14}$C] cholesterol-oleate formed was separated by thin-layer chromatography and the radioactivity was counted with liquid scintillation counter.

ACAT inhibitory activities of the test compounds were shown as $IC_{50}$ values.

(2) In-vitro Test Using THP-1 Intact Cell

About 2 million cells of human leukemia cell line, THP-1 were seeded in a well with 2 ml of medium and differentiated into macrophage-like cells by phorbol ester. Then, the cells were washed with phosphate-buffered saline (PBS) solution and the medium was replaced by fresh medium supplemented with 10% of lipoprotein-deficient serum. After the addition of each test compound dissolved in dimethyl sulfoxide and 100 μg protein-containing human low density lipoprotein (LDL), the reaction was initiated by the addition of 10 nmoles of labeled [$^{14}$C]oleic acid and 10 nmoles of oleic acid complexed with BSA in PBS solution. After 22 hours, the reaction was stopped by removal the medium and $CHCl_3$-MeOH (2:1) were added to the cell suspension in order to extract lipids.

Intracellular [$^{14}$C] cholesterol-oleate formed was separated by thin-layer chromatography and the radioactivity was counted with lipid scintillation counter.

ACAT inhibitory activities of the test compounds were shown as $IC_{50}$ values.

(3) In-vivo Test Using Mouse Peritoneal Macrophages

Male mice were fed a standard powder diet containing the test compounds for 16 days. After 14 and 15 days on this diet, aggregated-LDL (containing 4 mg cholesterol) prepared from LDL receptor deficient KHC rabbit and [$^{14}$C] oleic acid together with the said aggregated-LDL (containing 0.5 mg cholesterol) were injected into the peritoneal cavity of these animals, respectively. After 16 days on this treatment, peritoneal macrophages were harvested by peritoneal lavage with PBS solution and $CHCl_3$-MeOH (2:1) were added to the cell suspension in order to extract lipids. Formed [$^{14}$C] cholesterol oleate was separated by thin-layer chromatography and the radioactivity was counted.

ACAT inhibitory activities of the test compounds were shown as inhibiting percentage referred to control group.

(4) In Vitro Test Using THP-1 Microsome

ACAT enzyme fraction was prepared from microsome of human leukemia THP-1 cell as described above in method (1).

Microsome was suspended at a concentration of 200 μg protein/20 μl in 0.1M phosphate buffer solution (pH7.4) and the suspension was preincubated at 37.5 minutes after addition of 10 μl of each test compound dissolved in 0.1M phosphate buffer solution containing BSA. Then, the reaction was initiated by the addition of 5 nmoles of labeled [$^{14}$C] oleoyl-CoA dissolved in 20 μl of said phosphate buffer solution containing BSA and the reaction was stopped by the addition of 20 μl of 2N HCl after 10 minutes. [$^{14}$C]

cholesterol-oleate formed was separated by thin-layer chromatography and the radioactivity was counted with liquid scintillation counter.

ACAT inhibitory activities of the test compounds were shown as $IC_{50}$ values.

(5) Bioavailability Assessment of ACAT Inhibitors by Their <<ex vivo>> Activity

Five non-fasted female mice weighing 19.0–20.0 g were administered at 10 a.m. per os 30 mg/kg of oral suspension (1% carboxymethyl cellulose sodium salt (CMC-Na) 0.2% Tween 80). Blood samples were collected 0.5, 1, 1.5, 2, 6 hour postdose. Serum were harvested after gentle centrifugation and stored at −20.

The following day, 10 μl serum were preincubated at 37 for 5 minutes with 20 μl of THP-1 microsomal ACAT and then incubated 10 minutes with 20 μl of radiolabeled oleoyl-CoA as described above in method (4). The serum is used instead of the drug solution.

ACAT inhibitory activities of the test compounds were shown as maximum inhibition percentages ($I_{max}$).

(6) In Vivo Test Using Peritoneal Macrophages in C57BL/6J Mice

A standard pellet diet fed female C57BL/6J mice were administered at 10 a.m. per os 30 mg/kg/day of oral suspension (1% CMC-Na 0.2% Tween 80) for 4 days. Thioglycollate and [$^{14}$C] cholesterol were injected into the injection of labeled cholesterol, mice were sacrificed for the collection of peritoneal macrophages. Lipid was extracted, formed [$^{14}$C] cholesterol-ester was separated by thin-layer chromatography and radioactivity was counted as described above in method (3).

In vivo ACAT inhibitory activities on macrophages were expressed as percentage of inhibition compared to control group.

[Results]

(1) and (2): As can be seen in Table 1, the compounds caused a significant inhibitory activity on ACAT.

(3): As can be seen in Table 2, the compounds caused a significant inhibitory activity on ACAT.

(4) and (5): As can be seen in Table 3, the compounds showed a significant inhibitory activity on ACAT and high bioavailability.

(6) As can be seen in Table 4, the compounds caused a significant inhibitory activity on ACAT.

TABLE 1

$IC_{50}$ values of ACAT inhibitors on ACAT of HepG2 microsome and THP-1 cells.

| | $IC_{50}$ (μM) | |
|---|---|---|
| | HepG2 (microsome) | THP1 (intact cell) |
| 1 | 0.6 | 0.07 |
| 2 | 1.0 | 0.1 |
| 3 | 0.9 | 0.1 |
| 4 | 0.9 | 0.09 |
| 5 | 1.6 | 0.07 |
| 6 | 1.6 | 0.05 |
| 12 | 8.0 | 0.7 |
| 19 | 3.6 | 0.1 |
| 28 | 1.2 | 0.1 |
| 29 | 1.6 | 0.2 |
| 30 | 1.2 | 0.2 |
| 31 | 0.8 | 0.2 |
| 45 | 2.8 | 0.8 |

TABLE 2

Inhibition rate on ACAT of macrophage

| Test Compound (Example No.) | Inhibition rate (%) (macrophages) |
|---|---|
| 1 | 65 |
| 5 | 64 |
| E5324*[a] | 38 |
| CI976*[b] | 50 |

Notes:
*[a]: N-[6-methyl-2-{3-(5-ethyl-4-phenyl-1H-imidazol-1-yl)propoxy}]-phenyl-N'-butylurea
*[b]: 2,2-dimethyl-N-(2,4,6-trimethoxyphenyl)-dodecanamide

TABLE 3

| Test compound (Example No.) | $IC_{50}$ (μM) THP1 microsome | $I_{max}$ (%) Ex vivo |
|---|---|---|
| 62 | 0.03 | 62.57 |
| 63 | 0.05 | 68.52 |
| 64 | 0.2 | 43.14 |
| 65 | 0.06 | 37.43 |
| 66 | 0.08 | 77.59 |
| 67 | 0.05 | 51.97 |
| 68 | 0.03 | 50.51 |
| 69 | 0.03 | 40.11 |
| 70 | 0.06 | — |
| 71 | 0.09 | 81.1 |
| 73 | 0.02 | 38.17 |
| 77 (b) | 0.05 | 41.37 |
| 79 | 0.22 | 63.26* |
| 80 | 0.17 | — |
| 81 | 0.04 | 74.11* |
| 82 | 0.1 | 50.15 |
| 83 | 0.27 | — |
| 84 | 0.1 | 5.75 |
| 85 | 0.06 | 11.33 |
| 86 | 0.04 | — |
| 87 | 0.2 | — |
| 89 | 0.06 | — |
| 91 | 0.08 | 61.47 |
| 92 | 0.3 | — |
| 93 | 0.04 | 24.17 |
| 94 | 0.1 | 28.35 |
| 96 | 0.08 | 20.45 |
| 100 | 0.04 | 39.01 |
| 103 | 0.09 | — |
| 104 | 0.1 | — |
| 105 | 0.1 | — |
| 106 | 0.22 | — |
| 109 | 0.4 | — |
| 111 (a) | 0.1 | 62.01 |
| (b) | 0.09 | 63.56 |
| 112 | 0.2 | — |

*: Compounds were tested at 100 mg/kg in a suspension of 0.5% CMC-Na.

TABLE 4

| Test Compound (Example No.) | Inhibition rate (%) (macrophages) |
|---|---|
| [Experiment 1]*[a] | |
| 1 | 81.0 |
| 63 | 72.3 |
| 66 | 73.5 |
| E5324*[b] | 55.4 |
| PD132301-2*[c] | 93.2 |

TABLE 4-continued

| Test Compound (Example No.) | Inhibition rate (%) (macrophages) |
|---|---|
| [Experiment 2]*a | |
| 63 | 61.0 |
| 70 | 73.0 |
| 71 | 73.5 |

Notes:
*a: Two separate experiment were carried out on same method.
*b: N-[6-methyl-2-[3-(5-ethyl-4-phenyl-1H-imidazol-1-yl)propyloxy]]-phenyl-N'-butylurea
*c: N-[2,6-bis(1-metnylethyl)-phenyl]-N'-[[1-[4-(dimethylamino)-phenyl]cyclopentyl]methyl]urea, hydrochloride 2. Test for Toxicity

[Test Method]

(1) Acute toxicity: Nine compounds (Example Nos. 1, 2, 5, 6, 12, 19, 28, 31 and 45) were tested by using male ICR strain mouse weighing 23.0±0.7 g. Each test compound was suspended with 0.5% CMC-Na and orally administered in a dose of 1000 mg/10 ml/kg of body weight, and general signs were observed for seven days. Seven days after administration of each test compounds, no macroscopic changes were observed on any organs at autopsy.

(2) Acute toxicity: Five compounds (Example Nos. 1, 63, 66, 70, 71) were tested by using female C57BL/6J mice. Each test compound was suspended in 1% CMC-Na containing 0.2% Tween 80 solution and orally administered at a dose of 2000 mg/20 ml/kg of body weight.

[Results]

(1) No toxicological findings were observed in each test compound treated group.

(2) The lethal dose was not reach at 2000 mg/kg.

The following Preparations and Examples are further illustrative of the present invention. It is to be noted, however, that such Examples are by no means limitative of the scope of the invention. All compounds were identified by proton NMR spectrometry, mass spectrometry and/or other analytical or physical technique.

PREPARATIONS

Preparations 1 to 11 and Preparations 21 to 23 are described for synthesis of the amine (8) and Preparations 12 to 20 and Preparations 24 to 33 are described for synthesis of the 2-amino-benzamide (2), both of which are intermediate for the preparation of the objective 2-ureido-benzamide (1).

Preparation 1

4-Aminomethyl-1-diphenylmethylpiperidine

Step 1): Bromodiphenylmethane (2.5 g, 0.01 mol) in DMF (10 ml) was added dropwise at 0°–5° C. to a mixture of isonipecotamide (1.3 g, 0.01 mol) and $K_2CO_3$ (1.4 g) in DMF (25 ml). The reaction mixture was stirred for 2 hours at 0°–5° C., then poured into water. The mixture was extracted with ethylether, then the extract was washed with brine, dried ($MgSO_4$) and evaporated to give 1-diphenylmethylpiperidine-4-carboxamide (66%): mp 150° C.

Step 2): 1-Diphenylmethylpiperidine-4-carboxamide (1.5 g, 5.1 mmol) was added dropwise to a suspension of $LiAlH_4$ (0.4 g, 10.5 mmol) in THF (30 ml). The mixture was heated at 70° C. for 3 hours and then cooled. To the mixture, water (0.4 ml), 15% NaOH solution (0.4 ml) and water (1.2 ml) were added dropwise in order, and insoluble materials were filtered off. The filtrate was concentrated. The residue was purified by column chromatography on silica gel (10% methanol in dichloromethane) to give 4-aminomethyl-1-diphenylmethylpiperidine (57.0%) as colorless crystals: mp 80° C.

Preparation 2

4-(2-Aminoethyl)-1-diphenylmethylpiperidine

Step 1): In a similar manner to that of Preparation 1, but replacing isonipecotamide and 1-diphenylmethylpiperidine-4-carboxamide with ethyl isonipecotate and ethyl 1-diphenylmethyl-4-piperidinecarboxylate respectively, 1-diphenylmethyl-4-hydroxymethylpiperidine was prepared.

Step 2): $SOCl_2$ (0.6 ml, 8.2 mmol) was added dropwise to a solution of 1-diphenylmethyl-4-hydroxymethylpiperidine (1.0 g, 3.6 mmol) in benzene (7 ml) at room temperature. The mixture was refluxed for 18 hours and then concentrated. The residue was dissolved in ethyl acetate, washed with 5% NaOH solution, dried ($MgSO_4$) and concentrated. The residue was recrystallized (ethyl acetate/ether/hexane) to give 1-diphenylmethyl-4-chloromethylpiperidine (70.1%): mp 73°–75° C.

Step 3): NaCN (2.5 g, 51 mmol) was added to a solution of 1-diphenylmethyl-4-chloromethyl-piperidine (8.9 g, 29.7 mmol) in dimethyl sulfoxide (DMSO) (100 ml). The mixture was heated at 60° C. for 20 hours and then poured into 3% $NaHCO_3$ solution and extracted with ethyl acetate. The organic layer was dried ($MgSO_4$) and concentrated. The residue was purified by column chromatography on silica gel (10% ethyl acetate in hexane) to give 4-cyanomethyl-1-diphenylmethylpiperidine (61.4%): mp 103°–104° C. and 3-(2-cyanoethyl)-1-diphenylmethyl pyrrolidine (20.9%):oil.

Step 4): In a similar manner to that of Preparation 1 Step 2), but replacing 1-diphenyl-methylpiperidine-4-carboxamide with 4-cyanomethyl-1-diphenylmethylpiperidine, 4-(2-aminoethyl)-1-diphenylmethylpiperidine was obtained as an oily product.

Preparation 3

4-(3-Aminopropyl)-1-diphenylmethylpiperidine

Step 1): In a similar manner to that of Preparation 1 Step 1), but replacing isonipecotamide with 4-(2-hydroxyethyl)piperidine, 1-diphenylmethyl-4-(2-hydroxyethyl)piperidine was prepared.

Step 2): In a similar manner to that of Preparation 2 Step 2) to 4), but replacing 1-diphenylmethyl-4-hydroxymethylpiperidine with 1-diphenylmethyl-4-(2-hydroxyethyl)piperidine, 4-(3-aminopropyl)-1-diphenylmethylpiperidine was prepared.

Preparation 4

3-(3-Aminopropyl)-1-diphenylmethylpyrrolidine

In a similar manner to that of Preparation 1 Step 2), but replacing 1-diphenylmethyl-piperidine-4-carboxamide with 3-(2-cyanoethyl)-1-diphenylmethylpyrrolidine which was obtained according to Preparation 2 Step 3), 3-(3-aminopropyl)-1-diphenylmethyl-pyrrolidine was prepared.

Preparation 5

1-Diphenylmethyl-homopiperazine

In a similar manner to that of Preparation 1 Step 1), 1-diphenylmethylhomopiperazine was prepared from homopiperazine and bromodiphenylmethane.

Preparation 6

4-(10,11-Dihydrodibenzo[a,d]hepten-5-yl)piperazine

In a similar manner to that of Preparation 1 Step 1), 4-(10,11-dihydro-5-H-dibenzo[a,d]-cyclohepten-5-yl) piperazine was prepared from piperazine and 5-chlorodibenzosuberane.

Preparation 7

11-Aminomethyl-2-bromo-6,11-dihydrodibenz[b,e]oxepin

A solution of $AlCl_3$ (1.0 g, 7.5 mmol) in dry ether (10 ml) was added rapidly to a solution of $LiAlH_4$ (0.5 g, 13.2 mmol) in dry ether (13 ml). After 5 minutes, a suspension of 2-bromo-11-cyano-6,11-dihydrodibenz[b,e]oxepin (2.0 g, 6.7 mmol) in dry ether (100 ml) was added to the mixture of hydride. The reaction mixture was stirred for 4.5 hours. Water and Rochelle Salt were added to the reaction mixture. The mixture was poured into ether. The organic layer was dried ($MgSO_4$) and concentrated. The residue was purified by column chromatography on silica gel to give 11-aminomethyl-2-bromo-6,11-dihydrodibenz[b,e]oxepin (48.9%).

Preparation 8

11-(4-Aminopiperidin-1-yl)-2-bromo-6,11-dihydrodibenz[b,e]oxepin

Step 1): A solution of 2,11-dibromo-6,11-dihydrodibenz[b,e]oxepin (8.0 g, 22.7 mmol in benzene (100 ml) was added by portions to the solution of 1,4-dioxa-8-azaspiro[4,5]decane (6.5 g, 45.4 mmol) in acetonitrile (50 ml) in an ice bath. The reaction mixture was stirred at room temperature for 1 hour and then poured into water. The organic layer was washed with water, then dried ($MgSO_4$) and concentrated to give 11-(1,4-dioxa-8-azaspiro[4,5]decane-1-yl)-2-bromo-6,11-dihydrodibenz[b,e]oxepin (89.6%).

Step 2): A suspension of 11-(1,4-dioxa-8-azaspiro[4,5]decane-8-yl)-2-bromo-6,11-dihydrodibenz[b,e]oxepin (5.5 g, 13.2 mmol) in 4N HCl was heated at 60°–70° C. for 30 minutes. Then ethanol was added to the mixture. The mixture was heated at 60°–70° C. for 1.5 hours. After ethanol was evaporated, the reaction mixture was made alkaline with 50% NaOH solution, then extracted with ethyl acetate and chloroform. The organic layer was washed with water, dried ($MgSO_4$) and concentrated to give 11-(4-oxopiperidin-1-yl)-2-bromo-6,11-dihydrodibenz[b,e]oxepin (100%): mp 196°–200° C.

Step 3): A suspension of $NH_2OHHCl$ (1.22 g, 17.5 mmol) in ethanol (15 ml) was added to the solution of 11-(4-oxopiperidin-1-yl)-2-bromo-6,11-dihydro-dibenz[b,e]oxepin (6.5 g, 17.5 mmol) in ethanol (100 ml) under refluxing. The reaction mixture was refluxed for 1 hour, then concentrated. The residue was suspended with saturated $NaHCO_3$ solution and then extracted with ethyl acetate. The extract was washed with water, dried ($MgSO_4$) and concentrated to give 11-(4-hydroxyiminopiperidin-1-yl)-2-bromo-6,11-dihydrodibenz[b,e]oxepin (100%): mp 223°–225° C.

Step 4): $LiAlH_4$ (0.14 g, 3.7 mmol) was added to a solution of 11-(4-hydroxyiminopiperidin-1-yl)-2-bromo-6,11-dihydrodibenz[b,e]oxepin (1.5 g, 3.7 mmol) in dry THF (50 ml) under nitrogen atmosphere. The reaction mixture was heated at 60°–70° C. for 3 hours. After cooled at 0° C., the reaction mixture was hydrolyzed with water and diluted with ether, then filtered. The filtrate was concentrated to give 11-(4-aminopiperidin-1-yl)-2-bromo-6,11-dihydrodibenz[b,e]oxepin (69.1%): mp 142°–144° C.

Preparation 9

2-[2-(4-Aminopiperidin-1-yl)ethyl]thio-4,5-diphenylimidazole

Step 1): 1-Bromo-2-chloroethane (10.0 g, 0.07 mmol) was added by portions to a solution of 1,4-dioxa-8-azaspiro[4,5]decane (1.0 g, 7.0 mmol) and Et3N (0.7 g, 7.0 mmol) in acetonitrile (10 ml) at 0° C. The mixture was stirred at 0° C. for 48 hours, poured into ethyl acetate and washed with water. The organic layer was dried ($MgSO_4$) and concentrated to give 8-(2-chloroetyl)-1,4-dioxa-8-azaspiro-[4,5] decane (0.914 g, 63.5%) as a solid product.

Step 2): NaH (0.213 g, 8.8 mmol) was added to a suspension of 4,5-diphenyl-2-imidazolethiol (1.12 g, 4.4 mmol) in THF (30 ml). The mixture was refluxed for 1 hour. To the reaction mixture, 8-(2-chloroethyl)-1,4-dioxa-8-azaspiro[4,5]decane (0.914 g, 4.4 mmol) was added at 0° C. under stirring and refluxed 24 hours and then concentrated. The residue was poured into water and extracted with ethyl acetate. The organic layer was dried ($MgSO_4$) and concentrated.

The precipitate was recrystallized (toluene) to give 2-[2-(1,4-dioxa-8-azaspiro[4,5]decane-8-yl)ethyl]thio-4,5-diphenylimidazole (0.970 g, 52.3%).

Step 3): A suspension of 2-[2-(1,4-dioxa-8-azaspiro[4,5] decane-8-yl)ethyl]-thio-4,5-diphenylimidazole (0.86 g, 2.0 mmol) in concentrated HCl (20 ml) was heated at 60° C. for 2 hours. The reaction mixture was made basic with 10% NaOH solution and extracted with ethyl acetate. The organic layer was dried ($MgSO_4$) and concentrated to give 2-[2-(4-oxopiperidin-1-yl)ethyl]thio-4,5-diphenylimidazole (0.75 g, 98.7%) as a clear oil.

Step 4): Sodium cyanoborohydride (0.06 g, 9.5 mmol) was added to solution of 2-[2-(4-oxopiperidin-1-yl)ethyl]thio-4,5-diphenylimidazole (0.34 g, 0.91 mmol), powdered 3A molecular sieves (0.268 g) and ammonium acetate (0.73 g, 9.5 mmol) in methanol (10 ml). The mixture was stirred at room temperature under nitrogen atmosphere for 65 hours and then filtered and washed with methanol. The filtrate was concentrated. The residue was dissolved in 10% NaOH solution and ethyl acetate. The organic layer was washed with water and saturated NaCl solution, dried ($MgSO_4$) and concentrated. The residue was purified by column chromatography on silica gel (0.8% $NH_4OH$ in chloroform/methanol) to give 2-[2-(4-aminopiperidin-1-yl)ethyl]thio-4,5-diphenylimidazole (172 mg, 49.9%) as a pale yellow oil.

Preparation 10

2-(2-Aminoethylthio)-4,5-diphenylimidazole

60% NaH in oil (0.91 g, 22.8 mmol) was added to a suspension of 4,5-diphenyl-2-imidazolethiol (2.5 g, 9.9 mmol) in dry THF (80 ml) at room temperature under stirring. After 15 minutes, 2-bromoethylamine hydrobromide (2.0 g, 9.9 mmol) was added to the mixture. The reaction mixture was refluxed for 1 hour, then poured into water (500 ml) and extracted with ethyl acetate. The extract was dried ($MgSO_4$) and concentrated. The residue was recrystallized (toluene) to give 2-(2-aminoethylthio)-4,5-diphenylimidazole (51.3%): mp 152°–154° C.

Preparation 11

1-(2-Aminoethyl)-4,5-diphenylimidazole

Step 1): A solution of 4,5-diphenylimidazole (2.5 g, 11.3 mmol) in dry DMF (20 ml) was added to a suspension of NaH (0.33 g, 13.8 mmol) in dry DMF (5 ml) at 50° C. under nitrogen atmosphere. The reaction mixture was heated at 60° C. for 2 hours. After heating, the mixture was added dropwise to a solution of 1-bromo-2-chloroethane (4.9 g, 33.9 mmol) in dry DMF (30 ml) over 1 hour at 50° C. The reaction mixture was heated continuously at 40° C. for 5 hours, then poured into water and extracted with ethyl acetate. The organic layer was washed with water, dried (MgSO$_4$) and concentrated. The precipitates were filtered off. The filtrate was concentrated. The residue was purified by column chromatography on silica gel (ethyl acetate and hexane) to give 1-(2-chloroethyl)-4,5-diphenylimidazole (17.7%).

Step 2): A mixture of potassium phthalimide (0.21 g, 1.1 mmol) and 1-(2-chloroethyl)-4,5-diphenylimidazole (0.32 g, 1.1 mmol) in dry DMF (10 ml) was heated at 60°–70° C. for 6 hours. The reaction mixture was cooled, diluted with chloroform, poured into water and extracted with chloroform. The organic layer was dried (MgSO$_4$) and concentrated. The residue was purified by column chromatography on silica gel (40% ethyl acetate in chloroform) to give 1-(2-phthalimidoethyl)-4,5-diphenylimidazole (73.0%).

Step 3): 80% Hydrazine monohydrate (0.062 ml, 1.3 mmol) was added to a solution of 1-(2-phthalimidoethyl)-4,5-diphenylimidazole (0.32 g, 0.8 mmol) in methanol (20 ml) under refluxing. The reaction mixture was refluxed for 1 hour, then cooled. The mixture was made acidic slightly with 6N HCl and then filtered to remove phthalhydrazide. The filtrate was concentrated and then the residue was suspended in 2N NaOH. The suspended mixture was extracted with chloroform. The organic layer was washed with brine, dried (MgSO$_4$) and concentrated. The precipitates were recrystallized (ethyl acetate/hexane) to give 1-(2-aminoethyl)-4,5-diphenylimidazole (88.1%): mp 96°–98° C.

Preparation 12

2-Amino-5-dimethylamino-N-[(1-diphenylmethylpiperidin-4-yl)methyl]benzamide

Step 1): A mixture of 5-dimethylamino-2-nitrobenzoic acid [J. Med. Chem., 24, 742 (1981)](9.0 g, 40 mmol), 4-aminomethyl-1-diphenylmethylpiperidine (12.0 g, 40 mmol), 1-(3-dimethylamino-propyl)-3-ethylcarbodiimido hydrochloride (WSC) (8.0 g, 40 mmol) and 4-dimethylaminopyridine (DMAP) (5 g, 40 mmol) in dichloromethane (400 ml) was stirred at 0° C. for 1 hour, then at room temperature for 3 days. The reaction mixture was washed with 1N HCl, then water. The organic layer was dried (MgSO$_4$) and concentrated. The residue was purified by column chromatography on silica gel (5% methanol in dichloromethane) to give 5-dimethylamino-2-nitro-N-[(1-diphenylmethyl-piperidin-4-yl)methyl]benzamide (47%) as yellow solid: mp 200° C.

Step 2): A mixture of 5-dimethylamino-2-nitro-N-[(1-diphenylmethylpiperidin-4-yl)-methyl]benzamide (2.4 g, 5 mmol) and Raney Ni in methanol (50 ml) was hydrogenated at room temperature under stirring under 50 psi hydrogen pressure for 2 hours and then filtered. The filtrate was concentrated to give 2-amino-5-dimethylamino-N-[(1-diphenylmethylpiperidin-4-yl)-methyl]benzamide (2.2 g, 100%).

Preparation 13

2-Amino-5-dimethylamino-N-(1-diphenylmethylpiperidin-4-yl)benzamide

In a similar manner to that of Preparation 12, but replacing 4-aminomethyl-1-diphenylmethylpiperidine with 4-amino-1-diphenylmethylpiperidine (U.S. Pat. No. 4,267,318), 2-amino-5-dimethylamino-N-(1-diphenylmethylpiperidin-4-yl)benzamide was prepared.

Preparation 14

2-Amino-5-fluoro-N-(1-diphenylmethylpiperidin-4-yl)benzamide

In a similar manner to that of Preparation 12, 2-amino-5-fluoro-N-(1-diphenylmethylpiperidin-4-yl)benzamide was prepared from 5-fluoro-2-nitrobenzoic acid and 4-amino-1-diphenylmethylpiperidine.

Preparation 15

2-Amino-3-dimethylamino-N-(1-diphenylmethylpiperidin-4-yl)benzamide

Step 1): In a similar manner to Preparation 12 Step 1), 3-chloro-2-nitro-N-(1-diphenylmethylpiperidin-4-yl)benzamide was prepared from 3-chloro-2-nitrobenzoic acid and 4-amino-1-diphenylmethylpiperidine.

Step 2): A solution of 3-chloro-2-nitro-N-(1-diphenylmethylpiperidin-4-yl)benzamide (13.5 g, 30 mmol) and 40% dimethylamine (20 ml) in DMF (60 ml) was heated at 130° C. for 15.5 hours in a sealed tube. The mixture was poured into water and extracted with ether. The organic layer was washed with water, dried (MgSO$_4$) and concentrated. The residue was recrystallized (ethyl acetate/hexane) to give 3-dimethylamino-2-nitro-N-(1-diphenylmethyl piperidin-4-yl)benzamide (88.5%): mp 176° C.

Step 3): In a similar manner to Preparation 12 Step 2), but replacing 5-dimethylamino-2-nitro-N-[(1-diphenylmethylpiperidin-4-yl)methyl]benzamide with 3-dimethylamino-2-nitro-N-(1-diphenylmethylpiperidin-4-yl)benzamide, 2-amino-3-dimethylamino-N-(1-diphenylmethylpiperidin-4-yl)benzamide was prepared.

Preparation 16

2-Amino-3,5-dimethoxy-N-(1-diphenylmethylpiperidin-4-yl)benzamide

Step 1): A solution of SOCl$_2$ (0.5 ml, 6.6 mmol) in chloroform (10 ml) was added dropwise to a solution of 3,5-dimethoxy-2-nitrobenzoic acid [Bull. Soc. Chim. Fr., 127, 258 (1990)] (1.0 g, 4.4 mmol) and a catalytic amount of DMF in chloroform (20 ml) at room temperature. The reaction mixture was refluxed for 1 hour and then concentrated. The residue was dissolved in THF (10 ml). The THF solution was added dropwise to a solution of 4-amino-1-diphenylmethylpiperidine (1.2 g, 4.4 mmol) and triethylamine (0.5 ml, 6.6 mmol) in THF (20 ml) at 5° C. The mixture was stirred at room temperature for 1 hour and then concentrated. The residue was dissolved in ethyl acetate and washed with water. The organic layer was dried (MgSO$_4$) and concentrated. The residue was purified by column chromatography on silica gel (10% ethyl acetate in dichloromethane) to give 3,5-dimethoxy-2-nitro-N-(1-diphenylmethylpiperidin-4-yl)benzamide (81.0%): mp 148°–150° C.

Step 2): In a similar manner to that of Preparation 12 Step 2), but replacing 5-dimethylamino-2-nitro-N-(1-diphenylmethylpiperidin-4-yl)methylbenzamide with 3,5-dimethoxy-2-nitro-N-(1-diphenylmethylpiperidin-4-yl) benzamide, 2-amino-3,5-dimethoxy-N-(1-diphenylmethyl-piperidin-4-yl)benzamide was prepared: 100%.

Preparation 17

2-Amino-N-(2,6-diisopropylphenyl)benzamide

Step 1): In a similar manner to that of Preparation 16 Step 1), 2-nitro-N-(2,6-diisopropylphenyl)benzamide was prepared from 2-nitrobenzoyl chloride and 2,6-diisopropylaniline: 67.9%, mp 119°–121° C.

Step 2): Zinc powder (7.81 g, 119 mmol) was added slowly to a solution of 2-nitro-N-(2,6-diisopropylphenyl)benzamide (2.0 g, 6.3 mmol) in acetic acid (38.3 ml) below 10° C. The mixture was stirred for 2 hours at room temperature. The excess reagent was filtered off and the filtrate was neutralized with 10% NaOH solution. The mixture was extracted with ethyl acetate. The organic layer was dried (MgSO$_4$) and concentrated. The residue was recrystallized (ethyl acetate/hexane) to give 2-amino-N-(2,6-diisopropylphenyl)benzamide (77.1%): mp 207°–209° C.

Preparation 18

2-Amino-5-hydroxy-N-(3,3-diphenylpropyl)benzamide

In a similar manner to that of Preparation 12 Step 2), but replacing 5-dimethylamino-2-nitro-N-[(1-diphenylmethylpiperidin-4-yl)methyl]benzamide with 5-benzyloxy-2-nitro-N-(3,3-diphenylpropyl)benzamide [J. Med. Chem. 31, 2136 (1988)], 2-amino-5-hydroxy-N-(3,3-diphenylpropyl)benzamide was prepared.

Preparation 19

2-Amino-N-[(1-diphenylmethylpiperidin-4-yl)methyl]benzamide and Its Analogue Compounds of the Formula (2)

A solution of 4-aminomethyl-1-diphenylmethylpiperidine (2.5 g, 9.15 mmol) in dichloromethane (10 ml) was added to a suspension of isatoic anhydride (1.0 g, 6.1 mmol) in dichloromethane (25 ml) at room temperature. The reaction mixture was stirred for 1 hour and then poured into chloroform and washed with 5% NaHCO$_3$ solution. The organic layer was concentrated. The residue was dissolved in dichloromethane (25 ml) and poured into hexane (400 ml) to give 2-amino-N-[(1-diphenylmethylpiperidin-4-yl)methyl]benzamide as precipitate (100%): mp 153°–154° C.

In a similar manner, but replacing the 4-aminomethyl-1-diphenylmethylpiperidine and the isatoic anhydride with other appropriately substituted amine and other appropriately substituted isatoic anhydride respectively, the following compounds were prepared and identified.

2-amino-N-(1-diphenylmethylpiperidin-4-yl)benzamide;
2-amino-3-isopropyl-N-(1-diphenylmethylpiperidin-4-yl)benzamide;
2-amino-5-nitro-N-(1-diphenylmethylpiperidin-4-yl)benzamide;
2-amino-N-[2-(1-diphenylmethylpiperidin-4-yl)ethyl]benzamide;
2-amino-N-[3-(1-diphenylmethylpiperidin-4-yl)propyl]benzamide;
2-amino-N-(1-benzylpiperidin-4-yl)benzamide;
2-amino-N-[3-(1-diphenylmethylpyrrolidin-3-propyl]benzamide;
2-amino-N-(pyridin-3-yl)benzamide;
2-amino-N-(pyridin-2-yl)benzamide;
1-(2-aminobenzoyl)-4-diphenylmethylpiperazine;
1-(2-aminobenzoyl)-4-(2-methoxyphenyl)piperazine;
1-(2-aminobenzoyl)-4-diphenylmethylhomopiperazine;
1-(2-aminobenzoyl)-4-(10,11-dihydro-5H-dibenzo[a,d]cyclohepten-5-yl)piperazine.

Preparation 20

2-Amino-N-methyl-N-[(1-diphenylmethylpiperidin-4-yl)-methyl]benzamide

Step 1): To a cooled solution (0°–5° C.) of 4-aminometyl-1-diphenylmethylpiperidine (3.0 g, 0.01 mol) in formic acid (7.5 ml), acetic anhydride (6 ml) was added and the reaction mixture was stirred at room temperature for 17 hours. An aqueous NaOH solution was added to adjust the mixture to pH 12 and the mixture was extracted with ether. The organic layer was washed with water and brine, dried (MgSO$_4$) and concentrated. The residue was recrystallized (diisopropyl ether) to give 4-(N-formylamino)methyl-1-diphenylmethylpiperidine (2.9 g, 88%); mp 125° C.

Step 2): In a similar manner to that of Preparation 1 step 2), 4-(N-formylamino)methyl-1-diphenylmethylpiperidine was reduced by LiAlH4 to give 4-(N-methylamino)methyl-1-diphenylmethylpiperidine; yield 100%.

Step 3): A solution of 4-(N-methylamino)methyl-1-diphenylmethylpiperidine (1.8 g, 6.0 mmol), isatoic anhydride (0.9 g, 5.5 mmol) and 4-dimethylaminopyridine (0.74 g) in DMF (25 ml) was stirred at room temperature for 2 hours. The reaction mixture was poured into 1% NaHCO$_3$ solution and extracted with ethyl acetate. The organic layer was washed with water, dried and concentrated. The residue was purified by column chromatography on silica gel (ethyl acetate and hexane) to give 2-amino-N-methyl-N-[(1-diphenylmethylpiperidin-4-yl)methyl]benzamide (1.5 g, 67%).

Preparation 21

3-Aminomethyl-1-diphenylmethylpiperidine

Step 1): A solution of bromodiphenylmethane (48.2 g, 195 mmol) in DMSO (30 ml) was added dropwise to a solution of nipecotamide (25 g, 195 mmol) and K$_2$CO$_3$ (27 g, 195 mmol) in CH$_3$CN (100 ml) and DMSO (50 ml) under stirring and cooling in an ice-bath for 1 hour. After the addition was complete, the mixture was stirred overnight at room temperature. The insoluble precipitates were filtered off and then the filtrate was evaporated. To the residue was added H$_2$O and AcOEt, and agitated. The organic layer was washed with H$_2$O, dried over MgSO$_4$ and evaporated to give 1-diphenylmethylpiperidin-3-carboxamide, 33 g (57.5%): mp 86°–87° C.

Step 2): To a suspension of LiAlH$_4$ (10 g, 263 mmol) in THF (100 ml) was added dropwise a solution of 1-diphenylmethylpiperidin-3-carboxamide (32 g, 109 mmol) in THF (130 ml) for 40 mins under stirring and cooling in an ice-bath. After the addition was complete, the mixture was refluxed for 2 hours and then cooled. To the resulting mixture, 15% NaOH aqueous solution and H$_2$O were added dropwise in order, and the insoluble materials were filtered off. The filtrate was dried over MgSO$_4$ and evaporated. The residue was purified by column chromatography on silica gel to give 3-aminomethyl-1-diphenylmethylpiperidine as a colorless oil, 23 g (75.5%).

Preparation 22

4-Aminomethyl-1-(dibenzosuberan-5-yl)piperidine

4-Aminomethyl-1-(biphenyl-2-methyl)piperidine

4-Aminomethyl-1-(biphenyl-4-methyl)piperidine

4-Aminomethyl-1-[bis(4-fluorophenyl)methyl]piperidine

4-Aminomethyl-1-[bis(4-chlorophenyl)methyl]piperidine

4-Aminomethyl-1-[bis(4-methoxyphenyl)methyl]piperidine

In a similar manner to that of Preparation 1, but replacing bromodiphenylmethane with 5-chlorodibenzosuberane, 2-(bromomethyl)biphenyl, 4-(chloromethyl)biphenyl, chloro-bis(4-fluorophenyl)methane, chloro-bis(4-chlorophenyl)methane and chloro-bis(4-methoxyphenyl)methane, the above-mentioned amine derivatives were prepared.

Preparation 23

4-(1-Amino-1-methyl)ethyl-1-diphenylmethylpiperidine

Step 1): A solution of 1-diphenylmethylpiperidine-4-carboxamide (14.79 g, 50 mmol) in $POCl_3$ (300 ml) was refluxed for 3.5 hours. The reaction mixture was concentrated under vacuum. The residue was dissolved into the mixture of sat. $NaHCO_3$ aq. solution and AcOEt. After separation, the aqueous layer was extracted with AcOEt. The combined organic layer was washed with $H_2O$ and brine, dried over $MgSO_4$ and then concentrated. The residue was recrystallized from iso-PrOH to give 4-cyano-1-diphenylmethylpiperidine, 12.36 g (89%): mp 219°–230° C.

Step 2): $CeCl_3 \cdot 7H_2O$ (29.18 g, 105 mmol) was dried with stirring at 150° C. under vacuum for 2 hours, and then THF (200 ml) was added to make suspension. MeLi (1.4N sodium in $Et_2O$: 75 ml, 105 mmol) was added dropwise at the temperature under −70° C. The mixture was stirred at −75° C. for 1 hour. A solution of 4-cyano-1-diphenylmethylpiperidine (9.69 g) in THF (50 ml) was added dropwise at the same temperature. The mixture was allowed to warm to room temperature and stirred for 2 hours. The mixture was filtered, and the filtrate was concentrated. The residue was dissolved into the mixture of $H_2O$ and $CH_2Cl_2$. After separation, the aqueous layer was extracted with $CH_2Cl_2$. The combined organic layer was washed with $H_2O$ and brine, dried over $MgSO_4$, and then concentrated. The residue was chromatographed on silica gel (10% MeOH in AcOEt+$NH_4OH$) to give 4-(1-amino-1-methyl)ethyl-1-diphenylmethylpiperidine, 6.69 g (62%): mp 110°–115° C.

Preparation 24

2-Amino-5-dimethylamino-N-[(1-diphenylmethylpiperidin-4-yl)methyl]benzamide

Step 2): Conc. $HNO_3$ (25 ml) was added dropwise to a solution of 3-fluorobenzoic acid (25 g, 178 mmol) in conc. $H_2SO_4$ (190 ml) under cooling in an ice-bath and stirring for 30 mins. After the addition was complete, the mixture was stirred at 0° C. and at room temperature for each 30 mins. The resulting solution was poured into an ice water and extracted with AcOEt. The extract was washed with brine, dried over $MgSO_4$ and evaporated to give 5-fluoro-2-nitrobenzoic acid as yellow powder, 32.1 g (97.2%): mp 141°–142° C.

Step 2): A mixture of 5-fluoro-2-nitrobenzoic acid (15 g, 81 mmol), thionyl chloride (20 g, 168 mmol) and DMF (10 drops) in $CHCl_3$ (120 ml) was refluxed for 6 hours and then the resulting solution was evaporated to give colorless paste. This paste was used in the next step without purification.

Step 3): To a solution of 4-aminomethyl-1-diphenylmethylpiperidine (23 g, 82 mmol) and triethylamine (22 g, 217 mmol) in THF (140 ml) was added dropwise a solution of the above-obtained paste in THF (60 ml) under stirring and cooling in an ice-bath, and then the mixture was stirred for additional 20 hours at room temperature. The insoluble precipitates were filtered off and the filtrate was evaporated to give 5-fluoro-2-nitro-N-[(1-diphenylmethylpiperidin-4-yl)methyl]benzamide as pale yellow powders, 33.5 g (92.4%): mp 164°–166° C.

Step 4): A mixture of 5-fluoro-2-nitro-N-[(1-diphenylmethylpiperidin-4-yl)-methyl]benzamide (13.4 g, 30 mmol) and 2.0M MeOH solution of dimethylamine (45 ml, 90 mmol) in THF (100 ml) was refluxed for 22 hours. The resulting solution was evaporated to give 5-dimethylamino-2-nitro-N-[(1-diphenylmethylpiperidin-4-yl)methyl]benzamide as yellow powders, 14.1 g (99.6%).

Step 5): To a solution of 5-dimethylamino-2-nitro-N-[(1-diphenylmethylpiperidin-4-yl)methyl]benzamide (3.55 g, 7.5 mmol) in a mixture of MeOH/AcOEt (50 ml/50 ml) was added $PtO_2$ (100 mg). The suspended mixture was agitated under $H_2$ atmosphere (3 kg/cm$^2$) for 3 hours. The mixture was filtered, and the filtrate was concentrated under vacuum. The residue was triturated with $Et_2O$ to give 2-amino-5-dimethylamino-N-[(1-diphenylmethylipe-ridin-4-yl)methyl]benzamide as a colorless powder product, 3.0 g (92.0%).

Preparation 25

2-Amino-5-(N-tert-butoxycarbonyl-N-methyl)amino-N-[(1-diphenylmethylpiperidin-4-yl)methyl]benzamide Step 1): A mixture of 5-fluoro-2-nitro-N-[(1-diphenylmethylpiperidin-4-yl)methyl]benzamide (2.68 g, 6 mmol) and 40% methylamine in MeOH (5 ml, 64 mmol) in DMF (30 ml) was heated in a sealed tube at 180° C. for 7 hours. After cooling, the reaction mixture was poured into $H_2O$ and extracted with AcOEt. The extract was washed with $H_2O$, dried over $MgSO_4$ and evaporated, followed by crystallization from EtOH to give 5-methylamino-2-nitro-N-[(1-diphenylmethylpiperidin-4-yl)methyl]benzamide, 2.28 g (83%): mp 185° C.

Step 2): A mixture of 5-methylamino-2-nitro-N-[(1-diphenylmethylpiperidin-4-yl)methyl]benzamide (1.1 g, 2.4 mmol), di-tert-butyl dicarbonate (5.3 g, 24.3 mmol), triethylamine (5 drops) and DMF (1 ml) was heated at 180° C. overnight. After cooling, the reaction mixture was dissolved in $CHCl_3$ and the solution was washed with $H_2O$, dried over $MgSO_4$ and evaporated. The residue was purified by column chromatography on silica gel to give 5-(N-tert-butoxycarbonyl-N-methyl)amino-2-nitro-N-[(1-diphenylmethylpiperidin-4-yl)methyl]benzamide, 840 mg (62.5%): mp 167°–168° C.

Step 3): A mixture of 5-(N-tert-butoxycarbonyl-N-methyl)amino-2-nitro-N-[(1-diphenylmethylpiperidin-4-yl)methyl]benzamide (650 mg, 1.16 mmol) and $PtO_2$ (110 mg) in MeOH (50 ml) was agitated under $H_2$ atmosphere (3 kg/cm$^2$) at room temperature for 5 hours. The catalysts were filtered off and the filtrate was evaporated to give 2-amino-5-(N-tert-butoxycarbonyl-N-methyl)amino-N-[(1-diphenylmethylpiperidin-4-yl)methyl]benzamide as colorless powders, 550 mg (89.4%): mp 219°–221° C. (decomp.).

Preparation 26

2-Amino-5-methylthio-N-[(1-diphenylmethylpiperidin-4-yl)methyl]benzamide

Step 1): To a solution of 5-fluoro-2-nitro-N-[(1-diphenylmethylpiperidin-4-yl)methyl]benzamide (2.0 g, 4.46 mmol) in DMF (10 ml) was added dropwise a solution of sodium thiomethoxide (343 mg, 4.9 mmol) in DMF (10 ml) under stirring at room temperature. After the mixture was stirred overnight, an additional sodium thiomethoxide (34 mg, 0.49 mmol) was added to the mixture. The reaction mixture was diluted with AcOEt and washed twice with $H_2O$. The organic layer was dried over $MgSO_4$ and evaporated to give 5-methylthio-2-nitro-N-[(1-diphenylmethylpiperidin-4-yl)methyl]benzamide as colorless powders, 1.7 g (80%): mp 179°–181° C.

Step 2): A mixture of 5-methylthio-2-nitro-N-[(1-diphenylmethylpiperidin-4-yl)methyl]benzamide (500 mg, 1.05 mmol), Fe powder (587 mg, 1.05 mmol), conc. HCl (0.05 ml), $H_2O$ (8 ml) and EtOH (35 ml) was refluxed overnight. The insoluble precipitates were filtered off and then the filtrate was evaporated to give 2-amino-5-methylthio-N-[(1-diphenylmethylpiperidin-4-yl)methyl]benzamide as colorless powder, 450 mg (96%): mp 156°–157° C.

Preparation 27

2-Amino-5-hydroxy-N-[(1-diphenylmethylpiperidin-4-yl)methyl]benzamide

Step 1): A solution of 5-hydroxyanthranilic acid (500 mg, 3.26 mmol) and triphosgene (1.45 g, 4.9 mmol) in 1,4-dioxane (20 ml) was refluxed overnight. The reaction mixture was poured into $H_2O$ (30 ml), and then the precipitates were filtered and dried to give 6-hydroxy-1,2-dihydro-4H-3,1-benzoxazin-2,4-dione, 360 mg (62%).

Step 2): A mixture of 6-hydroxy-1,2-dihydro-4H-3,1-benzoxazin-2,4-dione (360 mg, 2 mmol) and 4-aminomethyl-1-diphenylmethylpiperidine (420 mg, 1.5 mmol) in DMSO (5 ml) was stirred for 3 hours at room temperature. The reaction mixture was diluted with AcOEt and washed twice with brine. The organic layer was dried over $MgSO_4$ and evaporated, and then the residue was purified by column chromatography on silica gel to give 2-amino-5-hydroxy-N-[(1-diphenylmethylpiperidin-4-yl)methyl]benzamide, 520 mg (63%).

Preparation 28

2-Amino-5-nitro-N-[(1-diphenylmethylpiperidin-4-yl)methyl]benzamide

4-Dimethylaminopyridine (122 mg, 1.0 mmol) was added to a solution of 6-nitro-1,2-dihydro-4H-3,1-benzoxazin-2,4-dione (prepared by nitration of isatoic anhydride) (2.0 g, 9.6 mmol) in DMF (15 ml) and stirred for 5 mins.

To this solution was added 4-aminomethyl-1-diphenylmethylpiperidine (2.7 g, 9.6 mmol) and stirred for 5 hours at room temperature. The reaction mixture was diluted with AcOEt (50 ml) and $H_2O$ (50 ml). The aqueous layer was extracted with AcOEt. The combined AcOEt layer was washed twice with brine, dried over $MgSO_4$ and evaporated. The residue was purified by column chromatography on silica gel to give 2-amino-5-nitro-N-[(1-diphenylmethylpiperidin-4-yl)methyl]benzamide, 2.47 g (58%).

Preparation 29

2-Amino-5-isopropyl-N-[(1-diphenylmethylpiperidin-4-yl)methyl]benzamide

Step 1): 30% $H_2O_2$ (6 ml) was added to a solution of 5-isopropyl-1H-indole-2,3-dione [J. Med. Chem., 19, 391 (1976)] (4.0 g, 21.1 mmol) in 1N-NaOH (15 ml) at 5° C. The mixture was stirred for 3 hours at room temperature and then poured into $H_2O$ and acidified. The precipitates were filtered to give 5-isopropylanthranilic acid, 2.6 g (68.6%): mp 93°–95° C.

Step 2): $(BOC)_2O$ (2.5 g, 14.3 mmol) was added to a solution of 5-isopropyl-anthranilic acid (2.5 g, 13.9 mmol) in t-BuOH. The mixture was stirred for 18 hours at room temperature and then poured into $H_2O$ and extracted with AcOEt. The extract was washed with $H_2O$, dried over $MgSO_4$ and evaporated. The residue was purified by column chromatography on silica gel to give 5-isopropyl-N-tert-butoxycarbonylanthranilic acid, 2.5 g (63.4%): mp 175° C.

Step 3): A mixture of 5-isopropyl-N-tert-butoxycarbonylanthranilic acid (1.0 g, 3.58 mmol), 4-aminomethyl-1-diphenylmethylpiperidine (1.0 g, 3.57 mmol), triethylamine (0.37 g, 3.66 mmol) and DPPA (1.0 g, 3.63 mmol) in DMF was stirred at 0° C. for 30 mins and at room temperature for 2 hours. The mixture was poured into $H_2O$ and extracted with AcOEt. The extract was washed with $H_2O$, dried over $MgSO_4$ and evaporated and then the residue was purified by column chromatography on silica gel to give 2-(tert-butoxycarbonyl)amino-5-isopropyl-N-[(1-diphenylmethylpiperidin-4-yl)methyl]benzamide, 1.86 g (96.4%): mp 88°–90° C.

Step 4): A mixture of 2-tert-butoxycarbonyl)amino-5-isopropyl-N-[(1-diphe-nylmethyl-piperidin-4-yl)methyl]benzamide (1.86 g, 3.43 mmol) in TFA (5 ml) was stirred at 0° C. for 30 mins and at room temperature for 30 mins. The mixture was poured into $H_2O$, neutralized with 15% NaOH aq. solution and extracted with AcOEt. The extract was washed with $H_2O$, dried over $MgSO_4$ and evaporated to give 2-amino-5-isopropyl-N-[(1-diphenylmethylpiperidin-4-yl)methyl]benzamide, 1.49 g (97.7%): mp 114°–116° C.

Preparation 30

2-Amino-4-chloro-N-[(1-diphenylmethylpiperidin-4-yl)methyl]benzamide

To a solution of 7-chloro-1,2-dihydro-4H-3,1-benzoxazin-2,4-dione (prepared by cyclization of N-benzyloxycarbonyl-4-chloroanthranilic acid with phosphorus tribromide) (1.0 g, 5.06 mmol) in DMF (18 ml) was added 4-dimethylaminopyridine (62 mg). After 5 mins of agitation at room temperature, 4-aminomethyl-1-diphenylmethylpiperidine (1.56 g, 5.56 mmol) was added to the solution and stirred for 5 hours. The reaction mixture was diluted with AcOEt, washed twice with $H_2O$, dried over $MgSO_4$ and evaporated. The residue was purified by column chromatography on silica gel to give 2-amino-4-chloro-N-[(1-diphenylmethylpiperidin-4-yl)methyl]benzamide, 892 mg (41%): mp 161°–162° C.

Preparation 31

2-Amino-6-dimethylamino-N-(1-diphenylmethylpiperidin-4-yl)benzamide

Step 1): An ice cooled solution of bromine (2.5 ml, 48.5 mmol) in 1N KOH aq.solution was added to the solution of 3-nitrophthalimide (9.66 g, 50 mmol) in 1N KOH aq.solution (150 ml) followed by 1N KOH at 0. The mixture was refluxed for 1.5 hours. After cooling, the mixture was neutralized with 2N HCl and stirred at 0 to precipitate 2-amino-6-nitrobenzoic acid, 6.23 g (68%): mp 190° C.

Step 2): A mixture of 2-amino-6-nitrobenzoic acid (3.64 g, 20 mmol), 4-amino-1-diphenylmethylpiperidine (5.33 g, 20 mmol), EDCI (4.00 g, 21 mmol) and DMAP (2.45 g, 20 mmol) in $CH_2Cl_2$ (60 ml) was stirred at room temperature for 56.5 hours. The reaction mixture was diluted with $CH_2Cl_2$, washed with $H_2O$ and brine. The organic layer was dried over $MgSO_4$ and concentrated under vacuum. The residue was purified with chromatography on SiO₂ (30–50% AcOEt in hexane) and recyrstallized from toluene to obtain 2-amino-6-nitro-N-(1-diphenyl-methylpiperidin-4-yl) benzamide, 2.33 g (27%): mp 217° C.

Step 3): A suspension of 2-amino-6-nitro-N-(1-diphenylmethyl-piperidin-4-yl) benzamide (2.00 g, 4.4 mmol) and NaBH₄ (1.25 g, 33 mmol) in THF (35 ml) was added slowly to an ice cooled mixture of 37% HCHO aq.solution (2.15 ml, 26.5 mmol) and 3M H₂SO₄ aq.solution (3.7 mol) at 0. The mixture was stirred at 0 for 1.5 hours, and then made strongly alkaline with NaOH aq.solution and extracted with Et₂O. The organic layer was washed with H₂O and brine. dried over MgSO₄ and concentrated under vacuum. The residue was recrystallized from a mixture of cyclohexane and AcOEt to obtain 2-dimethylamino-6-nitro-N-(1-diphenylmethylpiperidin-4-yl)benzamide 2.07 g (97%): mp 122° C.

Step 4): A mixture of 2-dimethylamino-6-nitro-N-(1-diphenylmethylpiperidin-4-yl)benzamide (1.60 g, 3.5 mmol) and Raney Nickel in EtOH (75 ml) was stirred under H₂ at room temperature for 4 hours. The mixture was filtered, and the filtrate was concentrated under vacuum to obtain 2-amino-6-dimethylamino-N-(1-diphenylmethylpiperidin-4-yl) benzamide. 1.42 g (95%).

PREPARATION 32

2-Amino-4-dimethylamino-N-(1-diphenylmethylpiperidin-4-yl)benzamide

Step 1): A hot solution of sodium polysulfate was added dropwise to the solution of 2,4-dinitrobenzoic acid (8.9 g, 42 mmol) in boiling water (400 ml). The mixture was refluxed for 1 hour.

After cooling, conc. HCl was added to the mixture to adjust the pH value of 2. And then, reflux was continued for 1 hour to remove excess Na polysulfate. The mixture was cooled, made alkaline with 40% NaOH aq. solution to adjust the pH value of 10 and filtered. The solids was washed with 5% Na₂CO₃ aq. solution. The filtrate was acidified with conc.HCl to adjust the pH value of 5 and treated with AcOH (50 ml) to obtain a precipitate. The recrystallization from H₂O afforded 4-amino-2-nitrobenzoic acid 4.2 g (55%): mp 230° C.

Step 2): A suspension of 4-amino-2-nitrobenzoic acid (0.80 g, 4.4 mmol) and NaBH₄ (1.25 g, 33 mmol) in THF (35 ml) was added slowly to an ice cooled mixture of 37% HCHO aq. solution (2.15 ml. 26.5 mmol) and 3M H₂SO₄ (3.7 ml) aq. solution at 0. The mixture was stirred at 0 for 1.5 hours, and then neutralized with NaOH aq.solution to adjust the pH value of 3 and extracted with Et₂O. The organic layer was washed with H₂O and brine. dried over MgSO₄ and concentrated under vacuum. The residue was recrystallized from MeOH to obtain 4-dimethylamino-2-nitrobenzoic acid 0.74 g (80%).

Step 3): The mixture of 4-dimethylamino-2-nitrobenzoic acid (4.20 g, 20 mmol), 4-amino-1-diphenylmethylpiperidine (5.33 g, 20 mmol). EDCl (4.00 g, 21 mmol) and DMAP (2.45 g, 20 mmol) in CH₂Cl₂ (60 ml) was stirred at room temperature for 17.5 hours. The reaction mixture was diluted with CH₂Cl₂, washed with H₂O and brine. The organic layer was dried over MgSO₄ and concentrated under vacuum. The residue was purified with chromatography on SiO₂ (50% AcOEt in hexane) and recrystallized from AcOEt to obtain 4-dimethylamino-2-nitro-N-(1-diphenylmethylpiperidin-4-yl)benzamide. 5.44 g (59%): mp 183° C.

Step 4): The mixture of 4-dimethylamino-2-nitro-N-(1-diphenylmethylpiperidin-4-yl)-bezamide (1.60 g, 3.5 mmol) and Raney Nickel in EtOH (75 ml) was stirred under H₂ at room temperature for 4 hours. The mixture was filtered, and the filtrate was concentrated under vacuum. The residue was purified with chromatography on silica gel (30–50% AcOEt in hexane) and recrystallized from diisopropyl ether to obtain 2-amino-4-dimethylamino-N-(1-diphenylmethyl-piperidin-4-yl)benzamide 1.18 g (79%): mp 118° C.

PREPARATION 33

2-Amino-5-(N-acetyl-N-methyl)amino-N-[(1-diphenylmethylpiperidin-4-yl)-methyl]-benzamide Step 1): A mixture of 5-methylamino-2-nitro-N-[(1-diphenylmethyl-piperidin-4-yl)methyl]benzamide (Preparation 24) (810 mg, 177 mmol) and acetic anhydride (3 g, 29.4 mmol) was refluxed for 1.5 hours. To the reaction mixture was added MeOH and evaporated to give oil. This oil was triturated with Et₂O to give 5-(N-acetyl-N-methyl) amino-2-nitro-N-[(1-diphenyl-methylpiperidin-4-yl) methyl]benzamide. 470 mg (53.2%) as pale yellow powders product. mp 175°–176° C.

Step 2): A mixture of 5-N-acetyl-N-methyl)amino-2-nitro-N-[(1-diphenylmethylpiperidin-4-yl)methyl] benzamide (500 mg, 1.0 mmol) and PtO₂ (110 mg) in MeOH (40 ml) was stirred under H₂ atmosphere (3 kg/cm²) at room temperature. The catalysts were filtered off and the filtrate was evaporated to give 2-amino-5-(N-acetyl-N-methyl) amino-N-[(1-diphenylmethylpiperidin-4-yl)methyl] benzamide as a colorless powder product. That product was used in the next step without purification. mp 224°–226° C.

EXAMPLE 1

2-(N'-n-Heptylureido)-5-dimethylamino-N-[(1-diphenylmethylpiperidin-4-yl)methyl]-benzamide A solution of phenyl chloroformate (0.7 ml. 5 mmol) in dichloromethane (5 ml) was added dropwise to a solution of 2-amino-5-dimethylamino-N-[(1-diphenylmethylpiperidin-4-yl)methyl]benzamide (2.2 g, 5 mmol) and NaHCO₃ (1.0 g, 11.9 mmol) in dichloromethane (50 ml).

The reaction mixture was stirred at 0° C. for 30 minutes and then poured into water and extracted with dichloromethane. The organic layer was dried (MgSO₄) and concentrated to give 2-phenoxy-carbonylamino-5-dimethylamino-N-[(1-diphenylmethylpiperidin-4-yl) methyl]benzamide.

n-Heptylamine (2.3 g, 20.2 mmol) was added to a solution of the carbamate described above in dichloromethane (50 ml). The mixture was refluxed for 3 hours and then concentrated. The residue was purified by column chromatography on silica gel to give 2-(N'-n-heptylureido)-5-dimethylamino-N-dimethylamino-N-[(1-diphenylmethylpiperidin-4-yl) methyl]benzamide (1.8 g, 62.0%): mp 178°–179° C.; ¹H NMR (DMSO-d₆)ppm: 0.86 (3H, t), 1.14–1.47 (12H, m), 1.50–1.68 (3H, m), 1.79 (2H, t), 2.70–2.89 (8H, m), 2.97 (2H, dt), 3.14 (2H, t), 4.27 (1H, s), 6.78–6.90 (3H, m), 7.13–7.41 (10H, m), 7.85 (1H, d), 8.51 (1H, t), 9.17 (1H, s).

In a similar manner, the following compounds (Examples 2 to 26) were prepared from other appropriately substituted 2-amino-benzamides and other appropriately substituted amines which were described in braces: {} after title of these compounds.

EXAMPLE 2

2-(N'-n-Butylureido)-N-[(1-diphenylmethylpiperidin-4-yl)methyl]benzamide

{2-amino-N-[(1-diphenylmethylpiperidin-4-yl)methyl] benzamide and n-butylamine}: yield 80.2%; mp 197°–198°

C.; ¹H NMR (DMSO-d₆)ppm: 0.86 (3H, t), 1.24–1.83 (11H, m), 2.79 (2H, d), 3.02(2H, dd), 3.15 (2H, t), 4.27 (1H, s), 6.91 (1H, t), 7.13–7.41 (12H, m), 7.57 (1H, d), 8.21 (1H, d), 8.57 (1H, t), 9.92 (1H, s).

EXAMPLE 3

2-(N'-n-Pentylureido)-N-[(1-diphenylmethylpiperidin-4-yl)methyl]benzamide

{2-amino-N-[(1-diphenylmethylpiperidin-4-yl)methyl]benzamide and n-pentylamine}:yield 29.9%; mp 178°–180° C. (EtOH); ¹NMR (DMSO-d₆)ppm: 0.86 (3H, t), 1.24–1.83 (13H, m), 2.79 (2H, d), 2.96 (2H, dd), 3.15 (2H, t, ), 4.26 (1H, s), 6.91 (1H, t), 7.13–7.41 (12H, m), 7.57 (1H, d), 8.22 (1H, d), 8.58 (1H, t), 9.93 (1H, s).

EXAMPLE 4

2-(N'-n-Hexylureido)-N-[(1-diphenylmethylpiperidin-4-yl)methyl]benzamide

{2-amino-N-[(1-diphenylmethylpiperidin-4-yl)methyl]benzamide and n-hexylamine}: yield 56.9%; mp 168°–169° C. (EtOH); ¹H NMR (DMSO-d₆)ppm: 0.86 (3H, t), 125–1.83 (15H, m), 2.79 (2H, d), 3.01 (2H, dd), 3.17 (2H, t), 4.26 (1H, s), 6.91 (1H, t), 7.13–7.40 (12H, m), 7.57 (1H, d), 8.21 (1H, d), 8.57 (1H, t), 9.95 (1H, s).

EXAMPLE 5

2-(N'-n-Heptylureido)-N-[(1-diphenylmethylpiperidin-4-yl)methyl]benzamide

{2-amino-N-[(1-diphenylmethylpiperidin-4-yl)methyl]benzamide and n-heptylamine}: yield 67%; mp 146°–148° C. ¹H NMR (DMSO-d₆)ppm: 0.86 (3H, t), 3.00 (2H, dd), 3.15 (2H, m), 4.27 (1H, s), 6.89–7.58 (14H, m), 8.04 (1H, d), 8.19 (1H, q), 8.59 (1H, t), 9.93 (1H, s).

EXAMPLE 6

2-(N'-n-Octylureido)-N-[(1-diphenylmethylpiperidin-4-yl)methyl]benzamide

{2-amino-N-[(1-diphenylmethylpiperidin-4-yl)methyl]benzamide and n-octylamine}: yield 72.1%; mp 155°–157° C. (EtOH); ¹H NMR (DMSO-d₆)ppm: 0.86 (3H, t), 1.25–1.83 (19H, m), 2.79 (2H, d), 3.01 (2H, dd), 3.15 (2H, t), 4.26 (1H, s), 6.91 (1H, t), 7.13–7.41 (12H, m), 7.57 (1H, d), 8.21 (1H, d), 8.58 (1H, t), 9.95 (1H, s).

EXAMPLE 7

2-(N'-n-Butylureido)-N-(1-diphenylmethylpiperidin-4-yl)benzamide

{2-amino-N-(1-diphenylmethylpiperidin-4-yl)benzamide and n-butylamine}: yield 93.0%; mp 204°–206° C.; ¹H NMR (CDCl₃)ppm: 0.92 (3H, t), 1.23–1.67 (6H, m), 2.04 (4H, m), 2.84 (2H,m), 3.24 (2H, q), 4.11 (1H, m), 4.28 (1H, s), 4.53 (1H, t), 6.55 (1H, d), 6.94 (1H, dd), 7.15–7.44 (12H, m), 8.40 (1H, d), 10.26 (1H, s).

EXAMPLE 8

2-(N'-n-Pentylureido)-N-(1-diphenylmethylpiperidin-4-yl)benzamide

{2-amino-N-(1-diphenylmethylpiperidin-4-yl)benzamide and n-pentylamine}: yield 65.0%; mp 199°–201° C.; ¹H NMR (CDCl₃)ppm: 0.89 (3H, t), 1.29–1.70 (8H, m), 1.92–2.15 (4H, m), 2.79–2.88 (2H, m), 3.23 (2H, q), 3.87–4.05 (1H, m), 4.28 (1H, s), 4.56 (1H, t), 6.08(1H, d), 6.91–7.44 (13H, m), 8.41 (1H, d), 10.25 (1H, s).

EXAMPLE 9

2-(N'-n-Hexylureido)-N-(1-diphenylmethylpiperidin-4-yl)benzamide

{2-amino-N-(1-diphenylmethylpiperidin-4-yl)benzamide and n-hexylamine}: yield 52.0%; mp 192°–194° C.; ¹H NMR (CDCl₃)ppm: 0.87 (3H, t), 1.25–1.67 (10H, m), 1.92–2.13 (4H, m), 2.79–2.87(2H, m), 3.24 (2H, q), 3.88–4.02 (1H, m), 4.28 (1H, s), 4.54 (1H, t), 6.05 (1H, d), 6.91–7.46 (13H, m), 8.41 (1H, d), 10.27 (1H, s).

EXAMPLE 10

2-(N'-n-Octylureido)-N-(1-diphenylmethylpiperidin-4-yl)benzamide

{2-amino-N-(1-diphenylmethylpiperidin-4-yl)benzamide and n-octylamine}: yield 51.0%: mp 149°–151° C.; ¹H NMR (CDCl₃)ppm: 0.87 (3H, t), 1.23–1.68 (14H, m), 1.92–2.15 (4H, m), 2.80–2.88(2H, m), 3.23 (2H, q), 3.86–4.02 (1H, m), 4.28 (1H, s), 4.57 (1H, t), 6.06 (1H, d), 6.91–7.48 (13H, m), 8.41 (1H, d), 10.26 (1H, s).

EXAMPLE 11

2-(N'-n-Nonylureido)-N-(1-diphenylmethylpiperidin-4-yl)benzamide

{2-amino-N-(1-diphenylmethylpiperidin-4-yl)benzamide and n-nonylamine}: yield 94.0%: mp 149°–150° C.; ¹H NMR (CDCl₃)ppm: 0.87 (3H, t), 1.25 (12H, m), 1.56 (6H, m), 2.04 (4H, m), 2.84 (2H, m), 3.23 (2H, q), 3.91 (1H, m), 4.28 (1H, s), 4.54 (1H, t), 6.05 (1H, d), 6.94 (1H, dd), 7.15–7.44 (12H, m), 8.40 (1H, d), 10.26 (1H, s).

EXAMPLE 12

2-(N'-n-Decylureido)-N-(1-diphenylmethylpiperidin-4-yl)benzamide

{2-amino-N-(1-diphenylmethylpiperidin-4-yl)benzamide and n-decylamine}: yield 83.0%: mp 204°–206° C.; ¹H NMR (CDCl₃)ppm: 0.92 (3H, t), 1.23–1.67 (6H, m), 2.04 (4H, m), 2.84 (2H,m), 3.24 (2H, q), 4.11 (1H, m), 4.28 (1H, s), 4.53 (1H, t), 6.55 (1H, d), 6.94 (1H, dd), 7.15–7.44 (12H, m), 8.40 (1H, d), 10.26 (1H, s).

EXAMPLE 13

3,5-Dimethoxy-2-(N'-n-heptylureido)-N-(1-diphenylmethylpiperidin-4-yl)-benzamide {2-amino-3,5-dimethoxy-N-(1-diphenylmethylpiperidin-4-yl)benzamide and n-heptylamine}: yield 64.0%; mp 195°–198° C.; ¹H NMR (CDCl₃)ppm: 0.85 (3H, t), 2.78 (2H, d), 3.18 (2H, dd), 3.76 (3H, s), 3.81 (3H, s), 3.95 (1H,m), 4.23 (1H, s), 4.86 (1H, t), 5.89 (1H, s), 6.48 (1H, d), 6.84 (1H, d), 7.35 (1H, d).

EXAMPLE 14

5-Fluoro-2-(N'-n-heptylureido)-N-(1-diphenylmethylpiperidin-4-yl)benzamide

{2-amino-5-fluoro-N-(1-diphenylmethylpiperidin-4-yl)benzamide and n-heptylamine}: yield 67%: mp 208°–210°

C.; ¹H NMR (CDCl₃)ppm: 0.87 (3H, t), 2.58 (2H, d), 3.22 (2H, dd), 3.90 (1H, m),4.23 (1H, s), 4.52 (1H, t), 5.05 (1H, d), 8.34 (1H, q), 9.94 (1H, s).

EXAMPLE 15

2-(N'-n-Heptylureido)-3-isopropyl-N-(1-diphenylmethylpiperidin-4-yl)benzamide

{2-amino-3-isopropyl-N-(1-diphenylmethylpiperidin-4-yl)benzamide and n-heptylamine}: yield 71.2%; mp 209°–212° C.; ¹H NMR (DMSO-d₆)ppm: 0.84 (3H, t), 1.21 (6H, d), 3.02 (2H, q), 3.10(1H, m), 3.69 (1H, m), 4.29 (1H, s), 6.50 (1H, t), 7.14–7.42 (13H, m), 7.66 (1H, s), 8.03 (1H, d).

EXAMPLE 16

2-(N'-n-Heptylureido)-5-nitro-N-(1-diphenylmethylpiperidin-4-yl)benzamide

{2-amino-5-nitro-N-(1-diphenylmethylpiperidin-4-yl)benzamide and n-heptylamine}: yield 52.0%: mp 165°–166° C.: ¹H NMR (CDCl₃)ppm: 0.86 (3H, t), 1.27–1.96 (12H, m), 2.02 (4H, m), 2.89 (2H, q), 3.24 (2H, q), 3.92 (1H, m), 4.30 (1H, s), 4.76 (1H, t), 6.33 (1H, d), 7.16–7.42 (10H, m), 8.25 (1H, dd), 8.30 (1H, d), 8.67 (1H, d), 10.86 (1H, s).

EXAMPLE 17

2-(N'-n-Heptylureido)-N-[3-(1-diphenylmethylpyrrolidin-3-yl)propyl]benzamide

{2-amino-N-[3-(1-diphenylmethylpyrrolidin-3-yl)propyl]benzamide and n-heptylamine}: yield 76.1%; mp 109°–111° C.; ¹H NMR (CDCl₃)ppm: 0.88 (3H, t), 1.24–1.62 (15H, m), 1.92–2.98 (2H, m), 2.10–2.24 (1H, m), 2.31–2.43 (1H, m), 2.42–2.63 (1H, m), 2.71 (1H, dd), 3.24 (1H, dt), 3.37 (2H, dt), 4.16 (1H, s), 4.64 (1H, t), 6.22 (1H, t), 6.92 (1H, dd), 7.10–7.50 (12H, m), 8.41 (1H, d), 10.26 (1H, s).

EXAMPLE 18

2-(N'-n-Heptylureido)-N-(2,6-diisopropylphenyl)benzamide

{2-amino-N-(2,6-diisopropylphenyl)benzamide and n-heptylamine}: yield 63.2%: mp 123°–125° C.; ¹H NMR (CDCl₃)ppm: 0.88 (3H, t), 1.16–1.30 (20H, m), 1.45–1.51 (2H, m), 3.07–3.25 (4H, m)4.59–4.63 (1H, t), 7.04–7.10 (1H, m), 7.25–7.71 (6H, m), 8.52–8.55 (1H, d), 10.36 (1H, s).

EXAMPLE 19

2-(N'-n-Heptylureido)-5-hydroxy-N-(3,3-diphenylpropyl)benzamide

{2-amino-5-hydroxy-N-(3,3-diphenylpropyl)benzamide and n-heptylamine}: yield 81.3%; mp 161.0–161.5° C.; ¹H NMR (CDCl₃)ppm: 0.87 (3H, t), 1.26 (8H, t), 1.39–1.55 (2H, m), 2.32 (2H,dt), 3.17 (2H, dt), 3.30 (2H, dt), 3.96 (1H, t), 4.69 (1H, t), 6.46 (1H, t), 6.58 (1H, d), 6.71 (1H, dd), 7.04 (1H, s), 7.13–7.30 (10H, m), 7.75 (1H, d), 9.41 (1H, s).

EXAMPLE 20

2-[N'-(3,5-Di-t-butyl-4-hydroxyphenyl)ureido]-N-(1-diphenylmethylpiperidin-4-yl)-benzamide {2-amino-N-(1-diphenylmethylpiperidin-4-yl)benzamide and 4-amino-2,6-di-t-butylphenol [G. M. Coppinger, Tetrahedron 18.61 (1962)]}: yield 27.0%: mp 218°–225° C.; ¹H NMR (CDCl₃)ppm: 1.43 (18H, m), 1.55–1.64 (2H, m), 1.89–2.13 (2H, m), 3.90–3.98 (1H, m), 4.37 (1H, s), 5.07 (1H, s), 5.43 (1H, d), 6.33 (1H, s), 6.95 (1H, t), 7.16–7.46 (14H, m), 8.43 (1H, d), 10.35 (1H, s).

EXAMPLE 21

2-[N'-(4-n-Heptylphenyl)ureido]-N-(1-diphenylmethylpiperidin-4-yl)-benzamide

{2-amino-N-(1-diphenylmethylpiperidin-4-yl)benzamide and 4-heptylaniline}: yield 86.0%; mp 173°–175° C.; ¹H NMR (CDCl₃)ppm: 0.87 (3H, t), 1.28 (6H, m), 1.58 (6H, m), 2.01 (4H, m), 2.25 (2H, t), 2.83 (2H, m), 3.88 (1H, bs), 4.26 (1H, s), 6.07 (1H, d), 6.54 (1H, s), 6.90–7.43 (18H, m), 8.37 (1H, d), 10.41 (1H, s).

EXAMPLE 22

2-[N'-(2-t-Butoxycarbonylaminoethyl)ureido]-N-(1-diphenylmethylpiperidin-4-yl)-benzamide {2-amino-N-(1-diphenylmethylpiperidin-4-yl)benzamide and t-butyl N-(2-aminoethyl) carbamate}: yield 89.0%: mp 226°–228° C.; ¹H NMR (CDCl₃)ppm: 1.41 (9H, s), 1.63 (2H, m), 1.94–2.12 (4H, m), 2.84 (2H, m), 3.33 (4H, m), 3.92 (1H, m), 4.28 (1H, s), 4.97 (2H, m), 6.10 (1H, d), 6.96 (1H, t), 7.25 (12H, m), 8.36 (1H, d), 10.29 (1H, s).

EXAMPLE 23

1-[2-(N'-n-Heptylureido)benzoyl]-4-(2-methoxyphenyl)piperazine

{1-(2-aminobenzoyl)-4-(2-methoxyphenyl)piperazine and n-heptylamine}: yield 64.0%: mp 209°–212° C.; ¹NMR (CDCl₃)ppm: 0.88 (3H, t), 3.19 (2H, q), 3.87 (3H, s), 4.96 (1H, m), 3.69 (1H,m), 4.29 (1H, t), 6.87–7.39 (7H, m), 8.04 (1H, d), 8.09 (1H, d).

EXAMPLE 24

1-[2-(N'-n-Heptylureido)benzoyl]-4-diphenylmethylpiperazine

{1-(2-aminobenzoyl)-4-diphenylmethylpiperazine and n-heptylamine}: yield 86.0%: mp 125°–127° C.; ¹H NMR (CDCl₃)ppm: 0.89 (3H, t), 1.29–1.31 (8H, m), 1.47–1.49 (2H, m), 2.32–2.50 (4H,m), 3.19 (2H, q), 3.41–3.80 (4H, m), 4.23 (1H, s), 3.90 (1H, t), 6.93 (1H, t), 7.09–7.41 (12H, m), 8.01 (1H, s), 8.04 (1H, d).

EXAMPLE 25

2-[N'-(2-Aminoethyl)ureido]-N-(1-diphenylmethylpiperidin-4-yl)benzamide

{2-amino-N-(1-diphenylmethylpiperidin-4-yl)benzamide and 1,2-diaminoethane}: yield 90.0%; ¹H NMR (CDCl₃)ppm: 1.58–2.07 (6H,m), 2.83 (4H, m), 3.25 (2H, m), 3.87 (1H, s), 4.25 (1H, s), 5.70 (1H, s), 6.45,(1H, d), 6.92 (1H, t), 7.14–7.4 (12H, m), 8.30 (1H, d), 10.11 (1H, s).

EXAMPLE 26

2-[N'-(2-Aminoethyl)ureido]-N-[(1-diphenylmethylpiperidin-4-yl)methyl]-benzamide {2-amino-N-[(1-diphenylmethylpiperidin-4-yl)methyl]benzamide and 1,2-diaminoethane}: yield 97%; mp 101°–103° C.; $^1$H NMR (CDCl$_3$)ppm: 1.34–1.43 (2H, m), 1.54–1.68 (3H, m), 1.83 (2H, t), 2.81–2.92 (6H, m), 3.27–3.31 (4H, m), 4.24 (1H, s), 5.31 (1H, bt), 6.39 (1H, bt), 6.82 (1H, d), 7.10–7.42 (12H, m), 8.33 (1H, d. J=8.2 Hz), 10.20 (1H, s).

EXAMPLE 27

2-(N'-n-Heptylureido)-N-(1-phenoxylcarbonylpiperidin-4-yl)benzamide

Phenyl chloroformate (5.0 ml, 40 mmol) was added to a solution of 2-amino-N-(1-benzylpiperidin-4-yl)benzamide (3.1 g, 10 mmol) in chloroform (50 ml). The mixture was refluxed for 2 hours. After cooling, ether was added and then the solution was washed with saturated NaHCO$_3$ solution and brine. The organic layer was concentrated to give 2-phenoxy carbonylamino-N-(1-phenoxylcarbonylpiperidin-4-yl)benzamide.

A solution of 2-phenoxycarbonylamino-N-(1-phenoxylcarbonylpiperidin-4-yl)benzamide (1.6 g, 3.5 mmol) and n-heptylamine (0.45 g, 3.9 mmol) in toluene (20 ml) was refluxed for 4 hours and then concentrated. The residue was purified by column chromatography on silica gel (50% ethyl acetate in petroleum ether) to give 2-(N'-n-heptylureido)-N-(1-phenoxy carbonylpiperidin-4-yl) benzamide: yield 95.0%: mp 142°–144° C.; $^1$H NMR (CDCl$_3$)ppm: 0.88 (3H, t) 1.28–1.33 (7H, m), 19–1.62 (4H, m), 2.05–2.17 (2H, m), 3.04–3.19 (2H, m), 3.25 (2H, q), 4.10–4.15 (1H, m), 4.24–4.40 (2H, m), 4.59 (1H, t), 6.35 (1H, d), 6.92 (1H, t), 6.97–7.44 (8H, m), 8.40 (1H,d), 10.20 (1H, s).

EXAMPLE 28

2-(N'-n-Heptylureido)-N-[2-(1-diphenylmethylpiperidin-4-yl)ethyl]benzamide

A solution of octanoic acid (0.5 g, 3.5 mmol), diphenylphosphoryl azide (1.0 g, 3.6 mmol) and Et$_3$N (0.4 g, 4 mmol) in acetonitrile (10 ml) was refluxed for 1 hour and then concentrated. The residue was dissolved in chloroform (10 ml). 2-Amino-N-[2-(1-diphenylmethylpiperidin-4-yl) ethyl]benzamide (0.74 g, 1.79 mmol) was added to the solution. The mixture was refluxed for 50 hours and then concentrated. The residue was purified by column chromatography on silica gel (10% to 30% ethyl acetate in hexane) to give 2-(N'-n-heptylureido)-N-[2-(1-diphenylmethylpiperidin-4-yl)ethyl]benzamide(0.88 g, 88.9%): mp 125°–127° C.; $^1$H NMR (CDCl$_3$)ppm: 0.88 (3H, t), 1.09–1.43 (10H, m), 1.44–1.77 (7H, m), 1.78–1.93 (2H,m), 2.88 (2H, d), 3.24 (2H, dt), 3.42 (2H, dt), 4.23 (1H, s), 4.58 (;1H, t), 6.16 (1H, t), 6.93 (1H,t), 7.13–7.45 (12H,m), 8.41 (1H,d), 10.28 (1H, s).

In a similar manner, the following compounds (Examples 29 to 42) were prepared from other appropriately substituted 2-amino-benzamides and other appropriately substituted carboxylic acids which were described in braces: {} after titles of these compounds.

EXAMPLE 29

2-(N'-n-Pentylureido)-N-[2-(1-diphenylmethylpiperidin-4-yl)ethyl]benzamide

{2-amino-N-[2-(1-diphenylmethylpiperidin-4-yl)ethyl]benzamide and n-hexanoic acid}: yield 40.6%: mp 124°–127° C.; $^1$H NMR (CDCl$_3$)ppm: 0.90 (3H, t), 1.25–1.44 (6H, m), 1.47–1.61 (5H,m), 1.61–1.71(2H, m), 1.83 (2H, t), 2.88 (2H, d), 3.27 (2H, dt), 3.45 (2H, dt), 4.23 (1H, s), 4.60 (1H, t), 6.15 (1H, t), 6.56 (1H, t), 7.13–7.44 (12H, m), 8.41 (1H, d), 10.28 (1H, s).

EXAMPLE 30

2-(N'-n-Hexylureido)-N-[2-(1-diphenylmethylpiperidin-4-yl)ethyl]benzamide

{2-amino-N-[2-(1-diphenylmethylpiperidin-4-yl)ethyl] benzamide and n-heptanoic acid}: yield 91.3%: mp 143°–144° C.; $^1$H NMR (CDCl$_3$)ppm: 0.88 (3H, t), 1.22–1.46 (8H, m), 1.46–1.75 (7H,m), 1.83 (2H, t), 2.88 (2H, d), 3.24 (2H, dt), 3.42 (2H, dt), 4.23 (1H, s), 4.58 (1H, t), 6.17 (1H, t), 6.93 (1H, t), 7.13–7.44 (12H, m), 8.40 (1H, d), 10.24 (1H, s).

EXAMPLE 31

2-(N'-n-Heptylureido)-5-dimethylamino-N-(1-diphenylmethylpiperidin-4-yl)-benzamide {2-amino-5-dimethylamino-N-(1-diphenylmethylpiperidin-4-yl)benzamide and n-octanoic acid}: yield 70.0%; mp 204°–206° C.; $^1$H NMR (CDCl$_3$) ppm: 0.86 (3H, t), 2.86 (6H, m), 3.76 (1H, m),4.30 (1H, s), 6.81–7.84 (3H, m), 7.15–7.44 (10H, m), 8.35 (1H, d), 9.08 (1H, s).

EXAMPLE 32

2-(N'-n-Heptylureido)-3-dimethylamino-N-(1-diphenylmethylpiperidin-4-yl)-benzamide {2-amino-3-dimethylamino-N-(1-diphenylmethylpiperidin-4-yl)benzamide and n-octanoic acid}: yield 38.0%; mp 203° C.; $^1$H NMR (CDCl$_3$)ppm: 0.85 (3H, t), 1.12–1.34 (8H, m), 1.35–1.61 (4H,m), 1.92(2H, d), 2.03 (2H, t), 2.55 (6H, s), 2.80 (2H, d), 3.16 (2H, dt), 3.86–4.05 (1H, m), 4.24 (1H, s), 5.56 (1H, d), 6.66 (1H, d), 6.93 (1H, s), 7.09–7.41 (13H, m).

EXAMPLE 33

2-(N'-n-Heptylureido)-N-methyl-N-[1-diphenylmethylpiperidin-4-yl)methyl]-benzamide {2-amino-N-methyl-N-[(1-diphenylmethylpiperidin-4-yl)methyl]benzamide and n-octanoic acid}: yield 68.0%; mp 140° C.; $^1$H NMR (CDCl$_3$)ppm: 0.88 (3H, t), 1.24–1.78 (19H, m), 2.93 (3H,s), 2.85–3.20 (5H, m), 3.42 (1H, d), 4.21 (1H, s), 5.07 (1H, t), 6.98–7.36 (14H, m), 7.98 (1H, s).

EXAMPLE 34

2-(N'-n-Heptylureido)-N-(pyridin-3-yl)benzamide

{2-amino-N-(pyridin-3-yl)benzamide and n-octanoic acid}: yield 85.2%: mp 144.5° C.; $^1$H NMR (CDCl$_3$)ppm: 0.85 (3H, t), 1.10–1.34 (8H, m), 1.35–1.49 (2H, m), 3.03 (2H, q), 7.05 (1H, t), 7.21 (1H, bt), 7.38–7.48 (2H, m), 7.72 (1H, d), 8.09–8.14 (1H, m), 8.22 (1H, d), 8.32–8.35 (1H, m), 8.90 (1H, t), 9.24 (1H, s), 10.57 (1H, s).

EXAMPLE 35

2-(N'-n-Heptylureido)-N-(pyridin-2-yl)benzamide

{2-amino-N-(pyridin-2-yl)benzamide and n-octanoic acid}: yield 84.0%: mp 118.5° C.; $^1$H NMR (CDCl$_3$)ppm: 0.88 (3H, t), 1.18–1.40 (8H, m), 1.44–1.62 (2H, m), 3.27

(2H, q), 4.66 (1H, t),6.99–7.11 (2H, m), 7.49 (1H, t), 7.63 (1H, d), 7.76 (1H, t), 8.24 (1H, d), 8.29–8.33 (1H, m), 8.49 (1H, d), 8.68 (1H, s), 10.11 (1H, s).

EXAMPLE 36

2-[N'-(1,1-Dimethyltridecyl)ureido]-N-(1-diphenylmethylpiperidin-4-yl)benzamide

{2-amino-N-(1-diphenylmethylpiperidin-4-yl)benzamide and 2,2-dimethyl tetradecanoic acid}: yield 38.0%: mp 146°–148° C.; $^1$H NMR (CDCl$_3$)ppm: 0.88 (3H, t), 1.24–1.32 (22H, m), 1.55 (6H, s), 1.62–1.66 (2H, m), 1.96–2.12 (4H, m), 2.83–2.87 (2H, m), 3.87–3.94(1H,m), 4.28 (1H, s), 4.44 (1H, t), 6.08 (1H, d), 6.89–6.95 (1H, t), 7.16–7.42 (12H, m),8.37(1H, d), 10.04 (1H, s).

EXAMPLE 37

2-[N'-(2,6-Diisopropylphenyl)ureido]-N-(1-diphenylmethylpiperidin-4-yl)-benzamide {2-amino-N-(1-diphenylmethylpiperidin-4-yl)benzamide and 2,6-diisopropyl benzoic acid}: yield 63.0%: mp 118° C.;) $^1$H NMR (CDCl$_3$)ppm: 1.17 (12H, d), 1.43–1.49 (2H, m), 1.816 (2H, m), 1.96–2.04 (2H, m), 2.77–2.81 (2H, m), 3.23–3.33 (2H, m), 3.75 (1H, m), 4.25 (1H, s), 5.82–5.91 (2H, m), 6.95 (1H, t), 7.16–7.41 (15H, m), 8.43 (1H, d), 9.53–9.54 (1H, m).

EXAMPLE 38

1-[2-(N'-n-Heptylureido)benzoyl]-4-diphenylmethylhomopiperazine

{1-(2-aminobenzoyl)-4-diphenylmethylhomopiperazine and n-octanoic acid}: yield 82.0%; mp 125° C.; $^1$H NMR (CDCl$_3$)ppm: 0.88 (3H, t), 1.29 (8H, bs), 1.42–1.56 (2H, s), 1.65–1.78 (1H, m), 1.83–1.95 (4H, m), 2.51–2.82 (4H, m), 3.13–3.28 (1H, m), 3.35–3.61 (2H, m), 3.67–3.88 (2H, m), 4.56 (1H, d), 4.85–5.00 (1H, m), 6.98 (1H, dt), 7.09–7.49 (12H, m), 7.82–8.16 (2H, m).

EXAMPLE 39

1-[2-(N'-n-Heptylureido)benzoyl]-4-10,11-dihydro-5H-dibenzo[a,d]cyclohepten-5-yl)piperazine {1-(2-aminobenzoyl)-4-(10,11-dihydro-5H-dibenzo[a,d] cyclohepten-5-yl)piperazine and n-octanoic acid}: yield 39.0%: mp 144° C.; $^1$H NMR (CDCl$_3$)ppm: 0.89 (3H, t), 1.18–1.43 (8H, m), 1.44–1.63 (2H,m), 2.18–2.48 (4H, m), 2.77–2.88 (2H, m), 3.22 (2H, q), 3.26–3.93 (4H, m), 3.94–4.02 (3H, m), 4.67 (1H, t), 6.92 (1H, t), 7.04–7.35 (10H, m), 8.07 (2H, t).

EXAMPLE 40

2-(N'-n-Heptylureido)-N-[3-(1-diphenylmethylpiperidin-4-yl)propyl]benzamide

{2-amino-N-[3-(1-diphenylmethylpiperidin-4-yl)propyl]benzamide and n-octanoic acid}: yield 45.3%: mp 123°–124.5° C. (AcOEt/hexane; $^1$H NMR (CDCl$_3$)ppm: 0.88 (3H,t), 1.14–1.40 (13H,m), 1.45–166 (6H,m), 1.81 (2H, t), 2.87 (2H, d), 3.24 (1H, dt), 3.38 (2H, dt), 4.22 (1H, s), 4.60 (1H, t), 6.24 (1H, t), 6.93 (1H, t), 7.13–7.32 (7H, m), 7.34–7.44 (5H, m), 8.40 (1H, d), 10.28 (1H, s).

EXAMPLE 41

N-(1-Benzylpiperidin-4-yl)-2-(N'-n-heptylureido) benzamide

{2-amino-N-(1-benzylpiperidin-4-yl)benzamide and n-octanoic acid}: yield 48.4%: mp 134° C.; $^1$H NMR (CDCl$_3$)ppm: 0.88 (3H,t), 1.20–1.40 (8H,m), 1.45–1.69 (4H,d), 2.18 (2H,t), 2.86 (2H,d), 3.24 (2H,q), 3.25 (2H, s), 3.83–4.03 (1H, m), 4.62 (1H,t), 6.13 (1H,d), 6.94 (1H,dt), 7.24–7.43 (7H,m), 8.40 (1H,dd), 10.26 (1H,s).

EXAMPLE 42

N-(1-Benzylpiperidin-4-yl)-2(N'-n-octylureido) benzamide

{2-amino-N-(1-benzylpiperidin-4-yl)benzamide and n-nonanoic acid}: yield 81.9%; mp 129° C.; $^1$H NMR (CDCl$_3$)ppm: 0.88 (3H,t), 1.17–1.41 (10H,m), 2.00 (2H,d), 2.18 (2H,t), 2.86 (2H,d), 3.25(2H,q), 3.52 (2H,s), 3.83–4.02 (1H,m), 4.56 (1H,t), 6.06 (1H,d), 6.95 (1H, dt), 7.24–7.45 (7H,m), 8.42 (1H,dd), 10.29 (1H,s).

EXAMPLE 43

N-[1-[2,6-Diisopropyl-4-(4-fluorophenyl)-5-(methoxymethyl)pyridin-3-yl]methylpiperidin-4-yl]-2-(N'-n-heptylureido)benzamide Step 1): 10% Pd/C was added to a solution of the N-(1-benzylpiperidin-4yl)-2-(N'-n-heptylureido)benzamide (1.4 g, 3.1 mmol) obtained in Example 41 in methanol (25 ml) under nitrogen. The mixture was shaken under 50 psi hydrogen pressure for 5 hours, and then filtered under nitrogen. The filtrate was concentrated. The residue was purified by column chromatography on silica gel (50% methanol and 0.8% NH$_4$OH in dichloromethane) to give N-(piperidin-4-yl)-2-(N'-n-heptylureido)benzamide: 48.4%: mp 159° C.

Step 2): N-(Piperidin-4-yl)-2-(N'-n-heptylureido) benzamide (0.96 g, 2.7 mmol) and NaBH$_3$CN (0.17 g, 2.7 mmol) were added into a solution of 2.6-diisopropyl-4-(4-fluorophenyl)-3-formyl-5-methoxymethylpyridine (0.9 g, 2.7 mmol) in MeOH (30 ml). The mixture was stirred at room temperature for 72 hours, and then water was added at 0° C. extracted with dichloromethane, dried (MgSO$_4$) and concentrated. The residue was purified by column chromatography on silica gel (10 to 50% ethyl acetate in hexane) to give N-[1-[2,6-diisopropyl-4-(4-fluorophenyl)-5-(methoxymethyl)pyridin-3-yl]methylpiperidin-4-yl]-2-(N'-n-heptylureido)benzamide (0.65 g, 35.7%): mp 123° C.: $^1$NMR (CDCl$_3$)ppm: 0.88 (3H, t), 1.17–1.46 (22H, m), 1.49–1.66 (2H, m), 1.80–2.00 (4H, m), 2.57 (2H, d), 3.09–3.53 (9H, m), 3.68–3.89 (1H, m), 3.49 (2H, s), 4.53 (1H, t), 5.98 (1H, d), 6.93 (1H, t), 7.05–7.24 (4H, m), 7.33–7.48 (2H, m), 8.41 (1H, d), 10.30 (1H, s).

The following compound (Example 44) was prepared in a similar manner, but replacing N-(1-benzylpiperidin-4-yl)-2-(N'-n-heptylureido)benzamide with N-(1-benzylpiperidin-4-yl)-2-(N'-n-octylureido)benzamide.

EXAMPLE 44

N-[1-[2,6-Diisopropyl-4-(4-fluorophenyl)-5-(methoxymethyl)pyridin-3-yl]methylpiperidin-4-yl]-2-(N'-n-octylureido)benzamide Yield 34.1%; mp 132° C.; $^1$H NMR (CDCl$_3$)ppm: 0.88 (3H, t), 117– 1.46 (24H, m), 1.49–1.66 (2H, m),1.80–2.00 (4H, m), 2.57 (2H, d), 3.09–3.55 (9H, m), 3.68–3.89 (1H, m), 3.49 (2H, s), 4.53 (1H, t), 5.98 (1H, d), 6.93 (1H, t), 7.05–7.24 (4H, m), 7.33–7.48 (2H, m), 8.41 (1H, d), 10.30 (1H, s).

EXAMPLE 45

2-(N'-n-Heptylureido)-N-(1-diphenylmethylpiperidin-4-yl)benzamide

A mixture of 2-n-heptylamino-4H-3,1-benzoxazin-4-one (3.0 g, 10 mmol) and 4-amino-1-diphenylmethylpiperidine (3.0 g, 10 mmol) in toluene (20 ml) was refluxed for 3 hours and then concentrated. The residue was purified by column chromatography on silica gel (20% ethyl acetate in hexane) to give 2-(N'-n-heptylureido)-N-(1-diphenylmethylpiperidin-4-yl)benzamide (2.3 g, 40%): mp 182° C.; $^1$H NMR (CDCl$_3$)ppm: 0.87 (3H, t), 1.27–1.30 (8H, m), 1.47–1.67 (4H, m), 1.95–2.12 (4H, m), 2.84 (2H, d), 3.24 (2H, q), 3.90–3.94 (1H, m), 4.26 (1H, s), 4.56 (1H, t), 6.09 (1H, d), 6.92–6.98 (1H, m), 7.16–7.44 (12H, m), 8.41 (1H, d), 10.26 (1H, s).

In a similar manner, the following compounds (Examples 46 to 53) were prepared from 2-n-heptylamino-4H-3,1-benzoxadin-4-one and other appropriately substituted amines which were described in braces: {} after titles of these compounds.

EXAMPLE 46

N-(3,5-Di-t-butyl-4-hydroxyphenyl)-2-(N'-heptylureido)benzamide

{4-amino-2,6-t-butylphenol}: yield 22.0%; mp 211°–214° C.; $^1$H NMR (CDCl$_3$)ppm: 0.86 (3H, d), 1.27–1.51 (28H, m), 3.16–3.23 (2H, q), 5.34 (1H, s), 5.60 (1H, s), 6.97 (1H, d), 7.00–7.45 (4H, m), 7.64 (1H, d), 8.34 (1H, d), 9.17 (1H, s), 9.84 (1H, s).

EXAMPLE 47

N-(4-n-Heptylphenyl)-2-(N'-n-heptylureido)benzamide

{4-n-heptylaniline}: yield 40.0%; mp 155°–157° C.; $^1$H NMR (CDCl$_3$)ppm: 0.85–0.94 (6H, d), 1.28–1.32 (20H, m), 2.61 (2H, t), 3.25 (2H, q), 4.61 (1H, s), 6.94–7.03 (1H, m), 7.19–7.65 (6H, m), 8.00 (1H, s), 8.40 (1H, d), 10.01 (1H, s).

EXAMPLE 48

N-(2-Bromo-6,11-dihydrodibenz[b,e]oxepin-11-yl)methyl-2-(N'-n-heptylureido)benzamide {11-aminomethyl-2-bromo-6,11-dihydrodibenz[b,e]oxepin}: yield 60.0%: mp 71°–76° C.; $^1$NMR (CDCl$_3$)ppm: 0.88 (3H, t), 1.32–1.62 (8H, m), 3.23–3.30 (2H, m), 4.77 and 5.69 (2H, q), 6.39(1H, s), 6.90–7.43 (10H, m), 8.40 (1H, d), 10.21 (1H, d).

EXAMPLE 49

N-[1-[2-(4,5-Diphenylimidazol-2-yl)thioethyl]piperidin-4-yl]-2-(N'-n-heptylureido)benzamide {2-[2-(4-aminopiperidin-1-yl)ethyl]thio-4,5-diphenylimidazole}: yield 45.6%: mp 160°–161° C.: $^1$H NMR (CDCl$_3$)ppm: 0.88 (3H, t), 1.08 (3H, ddd), 1.28–1.31 (8H, m), 1.51–1.56 (2H, m), 1.80(2H, d), 2.16 (2H, t), 2.93 (2H, t), 3.08–3.04 (4H, m), 3.24 (2H, dt), 3.80 (1H, m), 4.63 (1H, t), 5.27 (1H, d), 7.02–7.54 (13H, m), 8.43 (1H, d), 10.10 (1H, s).

EXAMPLE 50

N-(3,3-Diphenylpropyl)-2(N'-n-heptylureido)benzamide

{3,3-diphenylpropylamine}: yield 60.0%: mp 118° C.; $^1$H NMR (CDCl$_3$)ppm: 0.88 (3H,t), 1.06–1.72 (10H, b), 2.38 (2H,q), 3.00–3.60 (4H, m), 4.00 (1H, t), 4.60 (1H, t), 6.13 (1H, b), 6.64–7.52 (13H, m), 8.73 (1H, d), 10.28 (1H, s).

EXAMPLE 51

N-[1-(2-Bromo-6,11-dihydrodibenz[b,e]oxepin-11-yl)piperidin-4-yl]-2-(N'-n-heptylureido)benzamide {11-(4-aminopiperidin-1-yl)-2-bromo-6,11-dihydrodibenz[b,e]oxepin}: yield 54.1%: mp 198°–199° C.; $^1$H NMR (CDCl$_3$)ppm: 0.82–0.93 (3H, m), 1.27–1.64 (12H, m), 1.93–1.95 (2H, m), 2.12 (2H, q), 2.70 (1H, d), 2.87 (1H, d), 3.24 (2H, q), 3.90–4.00 (2H, m), 4.57 (2H, t), 6.03 (1H, d), 6.77–6.96 (4H, m), 7.09– 7.45 (9H, m), 8.40 (1H, d), 10.26 (1H, s).

EXAMPLE 52

N-[2-(4,5-Diphenylimidazol-2-yl)thioethyl]-2-(N'-n-heptylureido)benzamide

{2-(2-aminoethylthio)-4,5-diphenylimidazole}: yield 35.9%; mp 285°–288° C.; $^1$H NMR (CDCl$_3$)ppm: 0.97 (3H, t), 1.17–1.86 (10H, m), 3.24–3.31 (2H, m), 3.43 (2H, t), 3.86–3.92 (2H, m), 4.62–4.66 (1H, m), 6.36 (1H, t), 7.18–7.70 (13H, m), 8.36 (1H, d), 8.71–8.74 (1H, m), 10.53 (1H, s).

EXAMPLE 53

N-[2-(4,5-Diphenylimidazol-1-yl)ethyl]-2-(N'-n-heptylureido)benzamide

{1-(2-aminobenzoyl)-4-diphenylmethylpiperazine}: yield 86.0%; mp 169.7° C.; $^1$H NMR (CDCl$_3$)ppm: 0.89 (3H, t), 1.18–1.59 (10H, m), 3.20–3.7 (2H, dt), 3.45–3.51 (2H, dt), 4.06 (2H, t), 5.09–5.15 (1H, m), 6.45 (1H, t), 6.88–6.93 (1H, m), 7.15–7.46 (12H, m), 7.59 (1H, s), 8.45 (1H, d), 9.69–9.70 (1H, m).

EXAMPLE 54

2-(N'-n-Heptylureido)-N-(1-diphenylmethylpiperidin-3yl)-benzamide

Step 1): A mixture of 2-(N'-n-heptylureido)-N-(pyridin-3-yl)benzamide obtained in the Example 34 (5.0 g, 14 mmol) and PtO$_2$ in acetic acid (70 ml) was stirred at 40° C. under hydrogen atmosphere (50 psi) for 17 hours and then filtered. The filtrate was neutralized with 30% NaOH solution, extracted with ethyl acetate and washed with saturated NaHCO$_3$ solution. The organic layer was dried (MgSO$_4$) and concentrated. The residue was purified by column chromatography on silica gel (20% methanol and 0.8% NH$_4$OH in dichloromethane) to give 2-(N'-n-heptylureido)-N-(piperidin-3-yl)benzamide (83.8%): mp 165° C.

Step 2): Bromodiphenylmethane (1.4 g, 5.6 mmol) was added to a solution of 2-(N'-n-heptylureido)-N-(piperidin-3-yl)benzamide (1.0 g, 2.8 mmol) and K$_2$CO$_3$ (0.4 g, 2.9 mmol) in DMSO (5 ml) at 0° C. The mixture was refluxed for 18 hours, poured into 1% NaHCO$_3$ solution, extracted with ethyl acetate and washed with 1% NaHCO$_3$ solution. The organic layer was dried (MgSO$_4$) and concentrated. The residue was purified by column chromatography on silica gel (25% to 50% ethyl acetate in hexane) to give 2-(N'-n-heptylureido)-N-(1-diphenylmethylpiperidin-3-yl) benzamide (0.3 g, 20.5%): mp 112° C. $^1$H NMR (CDCl$_3$) ppm: 0.88 (3H, t), 1.23–1.35 (8H, m), 1.47–1.85 (6H, m), 2.05–2.20 (1H, m), 2.35–2.49 (1H, m), 2.57–2.80 (2H, m), 3.24 (2H, q), 4.12–4.23 (1H, m), 4.35 (1H, s), 4.57–4.65 (1H, m), 6.90–7.55 (14H, m), 8.48 (1H, d), 10.37 (1H, s).

EXAMPLE 55

2(N'-n-Heptylureido)-5-amino-N-(1-diphenylmethylpiperidin-4-yl)benzamide

In a similar manner to that of Example 54 step 1), but replacing 2-(N'-n-heptylureido)-N-(pyridin-3-yl)benzamide with 2-(N'-n-heptylureido)-5-nitro-N-(1-diphenylmethylpiperidin-4-yl) benzamide, 2-(N'-n-heptylureido)-5-amino-N-(1-diphenylmethyl-piperidin-4-yl)benzamide was prepared: yield 84.0%: mp 190°–192° C.; $^1$H NMR (CDCl$_3$)ppm: 0.84 (3H, t),1.26 (8H, m), 1.53 (8H, m), 1.92–2.11 (4H, m), 2.82 (2H, m), 3.19 (2H, td), 3.55 (2H,m), 3.91 (1H, s), 4.27 (1H, s), 4.46 (1H, m), 6.08 (1H, d), 6.71 (1H, d), 6.78 (1H, dd), 7.15–7.41 (10H, m), 8.00 (1H, d), 9.27 (1H, s).

EXAMPLE 56

2-(N'-n-Heptylureido)-5-methylsulfonylamino-N-(1-diphenylmethylpiperidin-4-yl)benzamide Methanesulfonyl chloride (0.05 ml, 0.65 mmol) was added dropwise to a solution of triethylamine (0.09 ml, 0.6 mmol) and 2-(N'-n-heptylureido)-5-amino-N-(1-diphenylmethylpiperidin-4-yl)benzamide (0.32 g, 0.59 mmol) in dichloromethane (15 ml) at 0° C. The mixture was stirred for 24 hours and then concentrated. The residue was purified by column chromatography on silica gel (50% ethyl acetate in cyclohexane) to give 2-(N'-n-heptylureido)-5-methylsulfonylamino-N-(1-diphenylmethylpiperidin-4-yl) benzamide (0.29 g, 79.0%): mp 180°–182° C.; $^1$H NMR (CDCl$_3$)ppm: 0.85 (3H, t), 1.28 (4H, m), 1.57 (6H, m), 2.00 (4H, m),2.85 (2H, m), 2.95 (3H, s), 3.12 (2H, td), 3.90 (1H, m), 4.29 (1H, s), 4.63 (1H, m), 6.22 (1H, d), 6.46 (1H, d), 7.15–7.41 (12H, m), 8.36 (1H, d), 10.17 (1H, s).

EXAMPLE 57

2-(N'-n-Heptylureido)-5-acetylamino-N-(1-diphenylmethylpiperidin-4-yl)benzamide

Triethylamine (0.098 ml, 0.65 mmol) and acetic anhydride (0.067 ml, 0.07 mmol) were added to a solution of the 2-(N'-n-heptylureido)-5-amino-N-(1-diphenylmethylpiperidin-4-yl)-benzamide (0.32 g, 0.59 mmol) in dichloromethane (3 ml) at room temperature. The mixture was stirred for 24 hours and then concentrated. The residue was purified by column chromatography on silica gel (50% ethyl acetate in cyclohexane) to give 2-(N'-n-heptylureido)-5acetylamino-N-(1-diphenylmethylpiperidin-4-yl)benzamide (0.33 g, 96.0%): mp 113°–115° C., $^1$H NMR (CDCl$_3$)ppm: 0.86 (3H, t), 1.27 (8H, m), 1.49–1.69 (4H, m), 1.92–2.08 (4H, m), 2.17 (3H, s), 2.85 (2H, m), 3.22 (2H, q), 3.90 (1H, m), 4.28 (1H, s), 4.57 (1H, t), 6.40 (1H, d), 7.03 (1H, dd), 7.15–7.40 (11H, m), 8.06 (1H, d), 8.30 (1H, d), 10.10 (1H, s).

EXAMPLE 58

2-(N'-n-Heptylureido)-5-(N'-n-butylureido)-N-(1-diphenylmethyl-piperidin-4-yl)benzamide In a similar manner to that of Example 28, 2-(N'-n-heptylureido)-5-(N'-n-butylureido)-N-(1-diphenylmethylpiperidin-4-yl)benzamide was prepared from n-pentanoic acid and 2-(N'-n-heptylureido)-5-amino-N-(1-diphenylmethyl-piperidin-4-yl)benzamide: yield 79.0%; mp 209°–211° C.; $^1$H NMR (DMSO-d$_6$) ppm: 0.83 (3H, t), 0.89 (3H, t), 3.77 (1H, m), 4.29 (1H, s), 6.08(1H, t), 7.00 (1H, bs), 7.15–7.40 (1H, m), 7.91 (1H, d), 8.30 (1H, s), 8.41 (1H, d), 9.06 (1H, d).

EXAMPLE 59

2-[N'-(2-Di-n-butylaminoethyl)ureido]-N-(1-diphenylmethylpiperidin-4-yl)benzamide To a solution of the 1,2[N'-(2-aminoethyl)ureido]-N-(1-diphenylmethylpiperidin-4-yl)-benzamide (0.33 g, 0.7 mmol) obtain in Example 25 and n-butyraldehyde (0.13 ml, 1.44 mmol) in methanol (5 ml) was added by portions NaBH$_3$CN (0.32 g, 5.1 mmol) under stirring and the pH was adjusted at 6 by adding acetic acid. Then the reaction mixture was stirred at room temperature for 2 hours. A few drops of concentrated HCl were added in order to decompose the excess of reducing reagent. The mixture was concentrated. The residue was dissolved in dichloromethane, then basified to pH 10 with 10% NaOH solution and extracted with dichloromethane. The organic layer was dried (MgSO$_4$) and concentrated. The residue was purified by column chromatography on silica gel (ethyl acetate) to give 2-[N'-(2-di-n-butylaminoethyl)ureido]-N-1-diphenylmethylpiperidin-4-yl)benzamide (0.15 g, 35.0%): mp 159°–161° C.; $^1$H NMR (CDCl$_3$)ppm: 0.89 (6H, t), 2.10 (4H, m), 2.48 (4H, t), 2.64 (2H, m), 3.84 (2H, m), 3.31 (2H, q), 3.95 (1H, m), 4.28 (1H, s), 5.30 (1H, bs), 6.06 (1H, d), 6.96 (1H, t), 7.15–7.44 (12H, m), 8.34 (1H, d), 10.20 (1H, s).

EXAMPLE 60

2-[N'-(2-n-Butylaminoethyl)ureido]-N-[(1-diphenylmethylpiperidin-4-yl)methyl]benzamide To a solution of 2-[N'-(2-aminoethyl)ureido]-N-[(1-diphenylmethylpiperidin-4-yl)-methyl] benzamide (500 mg, 1.0 mmol), obtained as described in Example 26, and n-butyraldehyde (88 μl, 1.1 mmol), was added acetic acid (59 μl) and a few minutes later sodiumborohydride triacetate (305 mg, 1.4 mmol) at room temperature. After 12 hours, the excess sodiumborohydride triacetate was destroyed by 10% NaHCO$_3$ solution (10 ml) and the mixture was extracted with ethyl acetate. The organic layer dried (MgSO$_4$) and concentrated. The residue was purified by flash column chromatography on silica gel (AcOEt 90/MeOH 10/NH$_4$OH 1) to give 2-[N'-(2-n-butylaminoethyl)ureido]-N-[(1-diphenylmethylpiperidin-4-yl)methyl]benzamide (110 mg, 20%): mp 148°–150° C.; $^1$H NMR (CDCl$_3$)ppm: 0.91 (3H, t), 1.28–1.61 (9H, m),1.7 (2H, t), 2.35 (1H,bs), 2.61 (2H, t), 2.78 (2H, t), 2.88–2.92 (2H, m), 3.27–3.38 (4H, m), 4.24 (1H, s), 5.37 (1H, bt), 6.39 (1H, bt), 6.92 (1H, t), 7.13–7.40 (12H, m), 8.35 (1H, d), 10.19 (1H, s).

The following compound (Example 61) was prepared in a similar manner, but replacing n-butyraldehyde with acetone.

EXAMPLE 61

2-[N'-(2-Isopropylaminoethyl)ureido]-N-[(1-diphenylmethylpiperidin-4-yl)-methyl]-benzamide Yield 59.0%; $^1$H NMR (CDCl$_3$)ppm: 1.06 (6H, d), 1.35–1.88 (8H, m), 2.75–2.93 (2H, 1H, 2H, m, h, t), 2.93–3.37 (4H, m), 4.24 (1H, s), 5.20(1H, bt), 6.31 (1H, bt), 6.94 (1H, t), 7.14–7.43 (12H, m), 8.37 (1H, d), 10.23 (1H, s).

EXAMPLE 62

2-(N'-n-Butylureido)-5-diethylamino-N-[(1-diphenylmethylpiperidin-4-yl)-methyl]-benzamide Step 1): To a solution of 5-fluoro-2-nitro-N-[(1-diphenylmethylpiperidin-4-yl)methyl]benzamide (prepared according to Preparation 24) (2.1 g, 4.68 mmol) in DMF (30 ml) was added diethylamine (1.46 ml, 14.06 mmol). The solution was refluxed overnight and evaporated under reduced pressure to give 5-diethylamino-2-nitro-N-[(1- diphenylmethylpiperidin-4-yl)methyl]benzamide (2.28 g, 97.5%): mp 167°–168° C.

Step 2): To a solution of 5-diethylamino-2-nitro-N-[(1-diphenylmethylpiperidin-4-yl)methyl]benzamide (1.0 g, 1.99 mmol) was added $PtO_2$ (30 mg). The solution was stirred under $H_2$ atmosphere (3 kg/cm$^2$) for 3 hours. The catalysts were filtered off and the filtrate was evaporated to give 2-amino-5-diethylamino-N-[(1-diphenylmethylpiperidin-4-yl)methyl]benzamide, 930 mg(100%): mp 161°–163° C.

Step 3): To a solution of 2-amino-5-diethylamino-N-[(1-diphenylmethylpiperidin-4-yl)methyl]benzamide (593 mg, 1.259 mmol) in $CHCl_3$ (20 ml) was added n-butylisocyanate (374 mg, 3.779 mmol). The solution was refluxed overnight and evaporated. The residue was purified by column chromatography on silica gel to give 5-diethylamino-2-(N'-n-butylureido)-N-[(1-diphenylmethylpiperidin-4-yl)methyl] benzamide, 366 mg (51%): mp 158°–160° C.;

$^1$H NMR (CDCl$_3$)ppm: 0.90 (3H, t), 1.12 (6H, t), 1.35–1.64 (9H, m), 1.84 (2H, t),2.90 (2H, d), 3.19–3.31 (8H, m), 4.24 (1H, s), 4.47 (1H, bt), 6.38 (1H, bt), 6.75–6.82 (2H, m), 7.16–7.40 (10H, m), 7.87 (1H, d), 8.66 (1H, s).

In a similar manner to that of Example 62, but in Step 1) replacing diethylamine with other amines (dimethylamine, di-n-propylamine, di-n-butylamine, pyrrolidine, piperidine, morpholine, imidazole, pyrazole), metal alkoxides (sodium methoxide, sodium ethoxide, sodium cyclopropylmethoxide), metal thioalkoxides (sodium thiomethoxide, sodium thioethoxide), in Step 2) using $PtO_2$. Raney-Ni as a catalyst or Fe powder/HCl and in Step 3) using n-butylisocyanate or n-propylisocyanate, the compounds described in Examples 63 to 78 were prepared.

EXAMPLE 63

2-(N'-n-Butylureido)-5-dimethylamino-N-[(1-diphenylmethylpiperidin-4-yl)-methyl]-benzamide {dimethylamine, n-butylisocyanate}: mp 201°–203° C.; $^1$H NMR (CDCl$_3$)ppm: 0.90 (3H, t), 1.29–1.84 (12H, m), 2.89 (6H, s), 3.18 (2H, q), 3.28 (2H, t), 4.24 (1H, s), 4.62 (1H, bt), 6.46 (1H, bt), 6.73–6.82 (2H, m), 7.14–7.41 (11H, m), 7.86 (1H, d), 8.82 (1H, s).

EXAMPLE 64

2-(N'-n-Butylureido)-5-(imidazol-1-yl)-N-[(1-diphenylmethylpiperidin-4-yl)-methyl]-benzamide {imidazole, n-butylisocyanate}: mp 197°–199° C.; $^1$H NMR (CDCl$_3$ )ppm: 0.92 (3H, t), 1.33–1.87 (11H, m), 2.84 (2H, m), 3.17–3.28 (4H, m), 4.23 (1H, s), 6.18 (1H, bs), 7.12–7.40 (13H, m), 7.73 (1H, d), 7.93 (1H, s), 8.32 (1H, bt), 8.50 (1H, d), 10.33 (1H, s).

EXAMPLE 65

2-(N'-n-Butylureido)-5-(pyrrolidin-1-yl)-N-[(1-diphenylmethylpiperidin-4-yl)methyl]-benzamide {pyrrolidine, n-butylisocyanate}: mp 200°–202° C.; $^1$H NMR (CDCl$_3$ )ppm: 0.90 (3H, t), 1.21–1.88 (9H, m), 1.99 4H, m), 2.90 (2H, m), 3.15–3.32 (8H, m), 4.24 (1H, s), 4.88 (1H, bt), 6.47 (1H, bt), 6.55 (1H, d), 6.64 (1H, dd), 7.13–7.40 (10H, m), 7.85(1H, d), 8.63 (1H, bs).

EXAMPLE 66

5-Dimethylamino-2-(N'-n-propylureido)-N-[(1-diphenylmethylpiperidin-4-yl)methyl]-benzamide {dimethylamine, n-propylisocyanate}: mp 199°–201° C.; $^1$H NMR (CDCl$_3$)ppm: 0.91 (3H, t), 1.25–1.90 (9H, m), 2.9 (8H, s+m), 3.17 (2H, q), 3.31 (2H, t), 4.25 (1H, s), 4.51 (1H, bt), 6.35 (1H,bt), 6.74 (1H, d), 6.85 (1H, dd), 7.14–7.41 (10H, m), 7.97 (1H, d), 8.93 (1H, bs).

EXAMPLE 67

2-(N'-Butylureido)-5-methoxy-N-[(1-diphenylmethylpiperidin-4-yl)methyl]-benzamide {sodium methoxide, n-butylisocyanate}: mp 206°–208° C.; $^1$H NMR (CDCl$_3$) ppm: 0.92(3H, t), 1.34–1.89(11H, m), 2.91 (2H, m), 3.23 (2H, q), 3.33(2H, t), 3.78(3H, s), 4.24 (1H, s), 4.49 (1H, bt), 6.22 (1H, bt), 6.89 (1H, d), 6.99 (1H, dd), 7.14–7.40 (10H, m), 8.22 (1H, d), 9.61 (1H, s).

EXAMPLE 68

2-(N'-n-Butylureido)-5-ethoxy-N-[(1-diphenylmethylpiperidin-4-yl)methyl]-benzamide {sodium ethoxide, n-butylisocyanate}: mp 191°–193° C.; $^1$H NMR (CDCl$_3$)ppm: 0.85 (3H, t), 1.19–1.81 (14H, m), 2.83 (2H, d), 3.12–3.25 (4H, m), 3.92 (2H, q), 4.17 (1H, s), 4.45 (1H, t), 6.21 (1H, t), 6.82 (1H, d), 6.90 (1H, dd), 7.07–7.34 (10H, m), 8.12 (1H, d), 9.54 (1H, s).

EXAMPLE 69

2-(N'-n-Butylureido)-5-cyclopropylmethoxy-N-[(1-diphenylmethylpiperidin-4-yl)methyl]-benzamide {sodium cyclopropylmethoxide, n-butylisocyanate}: mp 190°–192° C.; $^1$H NMR (CDCl$_3$)ppm: 0.33 (2H, m), 0.62 (2H, m), 0.91 (3H, t), 1.23–1.69(9H, m), 1.83 (3H, m), 2.90 (2H, m), 3.17–3.30 (4H, m), 3.75 (2H, m), 4.24(1H, s), 4.60(1H, bt), 6.35 (1H, bt), 6.96 (2H, m), 7.13–7.41 (10H, m), 8.16 (1H, d), 9.55 (1H, s).

EXAMPLE 70

2-(N'-n-Butylureido)-5-(morpholin-4-yl)-N-[(1-diphenylmethylpiperidin-4-yl)methyl]-benzamide {morpholine, n-butylisocyanate}: mp 208–°210° C.; $^1$H NMR (CDCl$_3$)ppm: 0.91 (3H, t), 1.31–1.88 (11H, m), 2.90 (2H, m), 3.06 (4H, m), 3.19 (2H, m),3.30 (2H, m), 3.84 (4H, m), 4.25 (1H,s), 4.58 (1H, bt), 6.36 (1H, bt), 6.88(1H, d), 7.00(1H, dd), 7.14–7.40(10H, m), 8.13(1H, d), 9.41 (1H, s).

EXAMPLE 71

5-(Morpholin-4-yl)-2-(N'-n-propylureido)-N-[(1-diphenylmethylpiperidin-4-yl)methyl]-benzamide {morpholine, n-propylisocyanate}: mp 215°–217° C.; $^1$H NMR (CDCl$_3$)ppm: 0.92(3H, t), 1.34–1.88(9H, m), 2.90 (2H, m), 3.06(4H, m), 3.18(2H, m), 3.30(2H, m), 3.84(4H, m), 4.24(1H, s), 4.59 (1H, bt), 6.34 (1H, bt), 6.88 (1H, d), 7.01 (1H, dd), 7.14–7.40 (10H, m), 8.13 (1H, d), 9.42 (1H, s).

EXAMPLE 72

5-Methylthio-2-(N'-n-propylureido)-N-[(1-diphenylmethylpiperidin-4-yl)methyl]benzamide {sodium thiomethoxide, n-propylisocyanate}: mp 196°–198° C.; $^1$H NMR (CDCl$_3$) ppm: 0.94 (3H, t), 1.36–1.70 (7H, m), 1.89 (2H, t), 2.45 (3H, s), 2.72 (2H, d), 3.20 (2H, q), 3.30 (2H, t), 4.25 (1H, s), 4.63 (1H, bt), 6.31 (1H, bt), 7.17–7.41 (12H, m), 8.34 (1H, d), 10.07 (1H, s).

EXAMPLE 73

2-N'-n-Butylureido)-5-methylthio-N-[(1-diphenylmethylpiperidin-4-yl)methyl]benzamide {sodium thiomethoxide, n-butylisocyanate}: mp 206°–208° C.; $^1$H NMR (CDCl$_3$)ppm: 0.92 (3H, t), 1.30–1.89 (11H, m), 2.44 (3H, s), 2.91 (2H, m), 3.20–3.32 (4H, m), 4.25 (1H,s), 4.62 (1H, bt), 6.32 (1H, bt), 7.14–7.40 (12H, m), 7.91 (1H, d), 8.33 (1H, d), 10.05 (1H, s).

EXAMPLE 74

2-(N'-n-Butylureido)-5-ethylthio-N-[(1-diphenylmethylpiperidin-4-yl)methyl]benzamide {sodium thioethoxide, n-butylisocyanate}: mp 159°–160° C.; $^1$H NMR (CDCl$_3$)ppm: 0.92 (3H, t), 1.24 (3H, t), 1.30–1.76 (14H, m), 1.85 (2H, t), 2.81–2.94 (4H, m), 3.21–3.33 (4H, m), 4.25 (1H, s), 4.61 (1H, bt), 6.28 (1H, bt), 7.14–7.45 (12H, m), 8.37 (1H, d), 10.19 (1H, s).

EXAMPLE 75

2-(N'-n-Butylureido)-5-(di-n-propyl)amino-N-[(1-diphenylmethylpiperidin-4-yl)methyl]-benzamide {di-n-propylamine, n-butylisocyanate}: mp 171.5°–172.5° C.; $^1$H NMR(CDCl$_3$)ppm: 0.90 (9H, t), 1.28–1.65 (11H, m), 1.83 (2H, t), 2.90 (2H, d), 3.16–3.32 (8H, m), 4.24 (1H, s), 4.55 (1H, bt), 6.47 (1H, bt), 6.70–6.75 (2H, m), 7.13–7.40 (12H, m), 7.76 (1H, d), 8.48 (1H, s).

EXAMPLE 76

5-di-n-Butyl)amino-2-(N'-n-butylureido)-N-[(1-diphenylmethylpiperidin-4-yl)methyl]-benzamide {di-n-butylamine, n-butylisocyanate}: mp 181.5°–182.5° C.; $^1$H NMR (CDCl$_3$)ppm: 0.86–0.94 (9H, m), 1.27–1.87 (17H, m), 2.89 (2H, d), 3.13–3.30 (8H, m), 4.23 (1H, s), 4.64 (1H, bt), 6.54 (1H, bt), 6.67–6.72 (2H, m), 7.13–7.40 (12H, m), 7.73 (1H, d), 8.49 (1H, s).

EXAMPLE 77

(a) 2-(N'-n-Butylureido)-5-hydroxy-N-[(1-diphenylmethylpiperidin4-yl)methyl]benzamide and (b) 5-n-butylcarbamyloxy-2-(N'-n-butylureido)-N-[(1-diphenylmethylpiperidin-4-yl)methyl]benzamide {2-amino-5-hydroxy-N-[(1-diphenylmethylpiperidin-4-yl)methyl]-benzamide and n-butyliso-cyanate}: mp 197°–199° C.; $^1$H NMR(CDCl$_3$)ppm: 0.90 (3H, t), 1.20–1.90 (11H, m), 2.88 (2H, m), 3.18 (2H, td), 3.25 (2H, dd), 4.23 (1H, s), 5.31 (1H, bs), 6.88 (1H, dd), 6.97 (1H, d), 7.10–741 (11H, m), 7.95 (1H, d), 8.66 (1H, s), 9.40 (1H, s); and, mp 153°–155° C.; $^1$H NMR(CDCl$_3$)ppm: 0.90 (6H, t), 1.30–1.85 (15H, m), 2.86 (2H, m), 3.21 (6H, m), 4.21 (1H, s), 4.63 (1H, bs), 5.02 (1H, bs), 6.54 (1H, bs), 7.00–7.40 (12H, m), 8.34 (10.01(1H, s), respectively.

EXAMPLE 78

2-(N'-n-Butylureido)-4-chloro-N-[(1-diphenylmethylpiperidin-4-yl)methyl]-benzamide {2-amino-4-chloro-N-[(1-diphenylmethylpiperidin-4-yl)methyl]benzamide and n-butylisocyanate}: mp 195°–197° C.; $^1$H NMR (CDCl$_3$)ppm: 0.93 (3H, t), 1.30–1.90 (11H, m), 2.91 (2H, m), 3.24 (2H, td), 3.31 (2H, dd), 4.25 (1H, s), 4.67 (1H, bs), 6.36 (1H, bs), 6.87 (1H, dd), 7.14–7.41 (11H, m), 8.51 (1H, d), 10.38 (1H, s).

In a similar manner to that of Example 62, but replacing Step 3) with the method of Example 1, the following compounds of Examples 79 to 105 were prepared.

EXAMPLE 79

2(N'-n-Heptylureido)-5-(imidazol-1-yl)-N-[(1-diphenylmethylpiperidin-4-yl)methyl]-benzamide {2-amino-5-(imidazol-1-yl)-N-[(1-diphenylmethylpiperidin-4-yl)methyl]benzamide and n-heptylamine}: mp 183°–185° C.; $^1$H NMR (CDCl$_3$)ppm: 0.88 (3H, t), 1.24–1.86 (17H, m), 2.89 (2H, m), 3.21 (2H, q), 3.34 (2H, m), 4.22 (1H, s), 4.97 (1H, t), 7.00 (1H, s), 7.07–7.40 (13H, m), 7.55 (1H, d), 8.48 (1H, d), 8.74 (1H, t), 10.55 (1H, s).

EXAMPLE 80

2-(N'-n-Decylureido)-5-dimethylamino-N-[(1-diphenylmethylpiperidin-4 -yl)methyl]-benzamide {2-amino-5-dimethylamino-N-[(1-diphenylmethylpiperidin-4-yl)methyl]benzamide and n-decylamine}: mp 145°–147° C.; $^1$NMR (CDCl$_3$)ppm: 0.88 (3H, t), 1.26–1.86 (27H, m), 2.87 (6H, s), 3.14 (2H, q), 3.26 (2H, t), 4.23 (1H, s), 4.76 (1H, bt), 6.73–6.78 (2H, m), 7.13–7.40 (11H, m), 7.77 (1H, d), 8.72 (1H, s).

EXAMPLE 81

2-(N'-n-Heptylureido)-5-methoxy-N-[(1-diphenylmethylpiperidin-4-yl)methyl]benzamide {2-amino-5-methoxy-N-[(1-diphenylmethylpiperidin-4-yl)methyl]-benzamide and n-heptylamine}: mp 189°–191° C.; $^1$H NMR (CDCl$_3$)ppm: 0.88 (3H, t), 1.29–1.88 (17H, m), 2.90 (2H, m), 3.23 (2H, q), 3.30 (2H, t), 3.78 (3H, s), 4.25 (1H, s), 4.52 (1H, bt), 6.27 (1H, bt), 6.90 (1H, d), 6.98 (1H, dd), 7.14–7.40 (10H, m), 9.21 (1H, d), 9.61 (1H, s).

EXAMPLE 82

2-(N'-n-Heptylureido)-5-(morpholin-4-yl)-N-[(1-diphenylmethylpiperidin-4-yl)methyl]-benzamide {2-amino-5-(morpholin-4-yl)-N-[(1-diphenylmethylpiperidin-4-yl)-methyl]benzamide and n-heptylamine}: mp 153°–155° C.; $^1$H NMR (CDCl$_3$)ppm: 0.88 (3H, t), 1.28–1.88 (17H, m), 2.91 (2H, m), 3.06 (4H, t), 3.20 (2H, q), 3.30 (2H, t), 3.84 (4H, t), 4.24 (1H, s), 4.56 (1H, bt), 6.35 (1H, bt), 6.89 (1H, d), 7.01 (1H, dd), 7.14–7.40 (10H, m), 8.15 (1H, d), 9.45 (1H, s).

EXAMPLE 83

2-(N'-n-Heptylureido)-5-(piperidin-1-yl)-N-[(1-diphenylmethylpiperidin-4-yl)methyl]benzamide {2-amino-5-(piperidin-1-yl)-N-[(1-diphenylmethylpiperidin-4-yl)methyl]benzamide and n-heptylamine}: mp 166°–168° C.; $^1$H NMR (CDCl$_3$)ppm: 0.88 (3H, t), 1.28–1.89 (23H, m), 2.90 (2H, m), 3.04 (2H, q), 3.23 (2H, q), 3.30(2H, t), 4.24(1H, s), 4.48(1H, bt), 6.25 (1H, bt), 6.93 (1H, d), 7.05 (1H, dd), 7.14–7.40(10H, m), 8.12(1H, d), 9.51(1H, s).

EXAMPLE 84

2-(N'-n-Heptylureido)-5-(pyrazol-1-yl)-N-[(1-diphenylmethylpiperidin-4-yl)-methyl]-benzamide {2-amino-5-(pyrazol-1-yl)-N-[(1-diphenylmethylpiperidin-4-yl)methyl]benzamide and n-heptylamine}: mp 176°–178° C.; $^1$H NMR (CDCl$_3$)ppm: 0.88 (3H, t), 1.28–1.87 (17H, m), 2.96 (2H, m), 3.24(2H, q), 3.34 (2H, t), 4.26 (1H, s), 4.70 (1H, bs), 6.46 (1H, dd), 6.66 (1H, bs), 7.14–7.42 (10H, m), 7.56(1H, dd), 7.69(1H, d), 7.88(2H, m), 8.53(1H, d), 10.28(1H, s).

EXAMPLE 85

2-(N'-n-Heptylureido)-5-(pyrrolidin-1-yl)-N-[(1-diphenylmethylpiperidin-4-yl)methyl]-benzamide {2-amino-5-(pyrrolidin-1-yl)-N-[(1-diphenylmethylpiperidin-4-yl)methyl]benzamide and n-heptylamine}: mp 182°–184° C.; $^1$H NMR (CDCl$_3$)ppm: 0.88 (3H, t), 1.27–1.98 (21H, m), 2.90 (2H, m), 3.13–3.29 (8H, m), 4.23 (1H, s), 4.55 (1H, bt), 6.55–6.63 (3H, m), 7.13–7.40 (10H, m), 7.80 (1H, d), 8.57(1H, bs).

EXAMPLE 86

5-Ethoxy-2-(N'-n-heptylureido)-N-[(1-diphenylmethylpiperidin-4-yl)methyl]-benzamide {2-amino-5-ethoxy-N-[(1-diphenylmethylpiperidin-4-yl)methyl]benzamide and n-heptylamine}: mp 188°–189° C.; $^1$H NMR (CDCl$_3$)ppm: 0.88 (3H, t), 1.28–1.88 (20H, m), 2.90 (2H, d), 3.20 (2H, q), 3.29 (2H, t), 3.99 (2H, q), 4.24 (1H, s), 4.51 (1H, t), 6.29 (1H, t), 6.89(1H, d), 6.97 (1H, dd), 7.14–7.41 (10H, m), 8.19 (1H, d), 9.62 (1H, s).

EXAMPLE 87

5-Diethylamino-2-(N'-n-heptylureido)-N-[(1-diphenylmethylpiperidin-4-yl)-methyl]-benzamide {2-amino-5-diethylamino-N-[(1-diphenylmethylpiperidin-4-yl)methyl]benzamide and n-heptylamine} mp 149°–151° C.; $^1$H NMR (CDCl$_3$)ppm: 0.86 (3H, t), 1.00–1.80 (23H, m), 2.83 (2H, m), 3.17 (8H, m), 4.17 (1H, s), 4.40 (1H, bs), 6.30 (1H, bs), 6.72 (2H, m), 7.10–7.40 (10H, m), 7.81 (1H, d), 8.60 (1H, bs).

EXAMPLE 88

2-(N'-Ethylureido)-5-dimethylamino-N-[(1-diphenylmethylpiperidin-4-yl)-methyl]benzamide {2-amino-5-dimethylamino-N-[(1-diphenylmethylpiperidin-4-yl)methyl]benzamide and ethylamine}: mp 186°–188° C.; $^1$H NMR (CDCl$_3$)ppm: 1.01 (3H, t), 1.20–1.90 (7H, m), 2.80 (2H, m), 2.87 (6H, s), 3.03 (2H, m), 3.17 (2H, bs), 4.30 (1H, s), 6.84 (3H, m), 7.18–7.44 (10H, m), 7.90 (1H, d), 8.53 (1H, bs), 9.24 (1H, s).

EXAMPLE 89

2-(N'-n-Heptylureido)-5-dimethylamino-N-[(1-diphenylmethylpiperidin-3-yl)methyl]-benzamide {2-amino-5-dimethylamino-N-[(1-diphenylmethylpiperidin-3-yl)methyl]benzamide and n-heptylamine}: mp 142°–144° C.; $^1$H NMR (CDCl$_3$)ppm: 0.88 (3H, t), 1.12–2.12 (17H, m), 2.53–2.69 (2H, m), 2.86 (6H, s), 3.19 (2H, q), 3.32 (2H, t), 4.24 (1H, s), 4.60 (1H, t), 6.62–6.63 (2H, m), 6.81 (1H, d d), 7.11–7.37 (1H, m), 7.92 (1H, d), 8.84 (1H, s).

EXAMPLE 90

2-(N'-n-Heptylureido)-5-hydroxy-N-[(1-diphenylmethylpiperidin-4-yl)methyl]benzamide {2-amino-5-hydroxy-N-[(1-diphenylmethylpiperidin-4-yl)methyl]-benzamide and n-heptylamine}: mp 165°–167° C.; $^1$H NMR (CDCl$_3$)ppm: 0.86 (3H, t), 1.20–1.90 (17H, m), 2.88 (2H, m), 3.15 (2H, td), 3.23 (2H, dd), 4.23 (1H, s), 5.20 (1H, bt), 6.80 (1H, bt), 6.91(2H, m), 7.10–7.40 (10H, m), 7.95 (1H, d), 8.62 (1H, s), 9.42 (1H, s).

EXAMPLE 91

5-(N-Acetyl-N-methyl)amino-2-(N'-n-heptylureido)-N-[(1-diphenylmethylpiperidin-4-yl)-methyl]benzamide {2-amino-5-(N-acetyl-N-methyl)amino-N-[(1-diphenylmethylpiperidin-4yl)methyl]benzamide and n-heptylamine}: mp 192°–193° C.; $^1$H NMR (CDCl$_3$)ppm: 0.89 (3H, t), 1.29–1.90 (20H, m), 1.83 (3H, s), 2.92 (2H, d), 3.20 (3H, s), 3.20–3.29 (2H, m), 3.33 (2H, t), 4.26 (1H, s), 4.65 (1H, t), 6.77 (1H, bs), 7.14–7.40 (11H, m), 8.50 (1H, d), 10.49 (1H, bs).

EXAMPLE 92

2-(N'-n-Heptylureido)-5-dimethylamino-N-[[1-bis(4-chlorophenyl)methylpiperidin-4-yl]-methyl] benzamide {2-amino-5-dimethylamino-N-[[1-bis(4-chlorophenyl) methylpiperidin-4-yl] methyl]benzamide and n-heptylamine}: mp 216° C.; $^1$H NMR (CDCl$_3$)ppm: 0.88 (3H, t), 1.20–1.90 (17H, m), 2.80–3.05 (2H, m), 2.90 (6H, s), 3.19 (2H, d), 3.30 (2H, t), 4.21 (1H, s), 4.53 (1H, bt), 6.53 (1H, bt), 6.65–6.92 (2H, m), 7.17–7.47 (8H, m), 7.76–8.00 (1H, m), 8.88 (1H, s)

EXAMPLE 93

2-(N'-n-Heptylureido)-5-dimethylamino-N-[[1-bis(4-fluorophenyl)methylpiperidin-4-yl]-methyl] benzamide {2-amino-5-dimethylamino-N-[[1-bis(4-fluorophenyl) methylpiperidin-4-yl]methyl]benzamide and n-heptylamine}: mp 220° C.; $^1$H NMR (CDCl$_3$)ppm: 0.88 (3H, t), 1.15–1.90 (17H, m), 2.78–3.02 (2H, m), 2.90 (6H, s), 3.19 (2H, q), 3.30 (2H, t), 4.23 (1H, s), 4.52 (1H, bt), 6.48 (1H, bt), 6.74 (1H, m), 6.84 (1H,d), 6.93–6.99 (4H, m), 7.29–7.34 (4H, m), 7.92 (1H, d), 8.88 (1H, s)

EXAMPLE 94

2-(N'-n-Heptylureido)-5-dimethylamino-N-[[1-bis(4-methoxyphenyl)methylpiperidin-4yl]methyl] benzamide {2-amino-5-dimethylamino-N-[[1-bis(4-methoxyphenyl) methylpiperidin-4-yl]methyl]benzamide and n-heptylamine}: mp 163° C.; $^1$H NMR (CDCl$_3$)ppm: 0.88 (3H, t), 1.12–1.96 (17H, m), 2.77–3.01 (2H, m), 2.90 (6H, s), 3.19 (2H, q), 3.29 (2H, t), 3.76 (6H, s), 4.17 (1H, s), 4.48 (1H, s), 6.40 (1H, s), 6.62–6.95 (6H, m), 7.17–7.40 (4H, m), 7.96 (1H, d), 8.95 (1H, s)

EXAMPLE 95

2-(N'-n-Heptylureido)-5-dimethylamino-N-[1-(4-biphenylmethylpiperidin-4-yl)methyl]-benzamide {2-amino-5-dimethylamino-N-[-1-(4-biphenylmethylpiperidin-4-yl)-methyl]benzamide and n-heptylamine}: mp 186° C.; $^1$H NMR (DMSO-d$_6$)ppm: 0.86 (3H, t), 1.27 (8H, m), 1.40 (2H, t), 1.58–1.63 (1H, m), 1.68 (2H, d), 2.02 (2H, t), 2.85 (6H, s), 3.02 (2H, q), 3.17 (2H, t), 3.50 (2H, s), 6.34 (1H, bt), 6.77 (1H, dd), 6.86 (1H, d), 7.28–7.45 (5H, m), 7.54–7.62 (4H, m), 7.79 (1H, d), 8.04 (1H, bt), 8.86 (1H, s).

EXAMPLE 96

2-(N'-n-Heptylureido)-5-dimethylamino-N-[1-(2-biphenylmethylpiperidin-4-yl)methyl]-benzamide {2-amino-5-dimethylamino-N-[1-(2-biphenylmethylpiperidin-4-yl)methyl]benzamide and n-heptylamine}: mp 160° C.; $^1$H NMR (DMSO-d$_6$)ppm: 0.84 (3H, t), 1.10–1.63 (15H, m), 1.78 (2H, t), 2.71 (2H, d), 2.84 (6H, s), 2.98 (2H, q), 3.11 (2H, t), 3.32 (2H, s), 6.80 (1H, d), 6.84 (1H, d), 6.91 (1H, bt), 7.21 (1H, dd), 7.28–7.44 (7H, m), 7.50 (1H, dd), 7.87 (1H, d), 8.52 (1H, bt), 9.22 (1H, s).

EXAMPLE 97

2-(N'-n-Heptylureido)-5-dimethylamino-N-[[1-dibenzosuberan-5-yl)piperidin-4 -yl]methyl] benzamide {2-amino-5-dimethylamino-N-[[1-(dibenzosuberan-5-yl)piperidin-4-yl]methyl]benzamide and n-heptylamine}: mp 207° C.; $^1$H NMR (DMSO-d$_6$)ppm: 0.86 (3H, t), 0.98–1.96 (17H, m), 2.60 (2H, d), 2.74 (2H, q), 2.83 (6H, s), 2.96 (2H, q), 3.10 (2H, bt), 3.92 (4H, q), 3.98 (1H, s), 6.81 (2H, d), 6.89 (1H, bt), 6.98–7.29 (8H, m), 7.84 (1H, d), 8.51 (1H, bt), 9.13 (1H, s).

EXAMPLE 98

2-(N'-n-Heptylureido)-5-dimethylamino-N-[(8-diphenylmethyl-8-azabicyclo[3,2,1]octan-3-yl)methyl]benzamide {2-amino-5-dimethylamino-N-[(8-diphenylmethyl-8-azabicyclo[3.2.1]octan-3-yl)methyl] benzamide and n-heptylamine}: mp 195° C.; $^1$H NMR (CDCl$_3$)ppm: 0.88 (3H, t), 1.27 (8H, m), 1.49–1.61 (8H, m), 1.90–2.00 (1H, m), 1.99–2.02 (2H, m), 2.91 (6H, s), 3.17–3.22 (4H, m), 3.29–3.33 (2H, m), 4.44 (1H, s), 4.51 (1H, bt), 6.41 (1H, bt), 6.73 (1H, d), 6.85 (1H, dd), 7.13–7.28 (6H, m), 7.47 (4H, d), 7.96 (1H, d), 8.94(1H, s).

EXAMPLE 99

2-(N'-n-Heptylureido)-5-dimethylamino-N-[1-methyl-1-(1-diphenylmethylpiperidin-4-yl)-ethyl]benzamide {2-amino-5-dimethylamino-N-[1-methyl-1-(1-diphenylmethylpiperidin-4-yl)ethyl]benzamide and n-heptylamine}: mp 190° C.: $^1$H NMR (CDCl$_3$)ppm: 0.88 (3H, t), 1.27 (8H, m), 1.49–1.61 (8H, m), 1.90–2.00 (1H, m), 1.99–2.02 (2H, m), 2.91 (6H, s), 3.17–3.22 (4H, m), 3.29–3.33 (2H, m), 4.44 (1H, s), 4.51 (1H, bt), 6.41 (1H, bt), 6.73 (1H, d), 6.85 (1H, dd), 7.13–7.28 (6H, m), 7.47 (4H, d), 7.96 (1H, d), 8.94 (1H, s).

EXAMPLE 100

5-Dimethylamino-2-(N'-n-pentylureido)-N-[(1-diphenylmethylpiperidin-4-yl)methyl]benzamide {2-amino-5-dimethylamino-N-[(diphenylmethylpiperidin-4-yl)methyl]benzamide and n-pentylamine}: mp 218° C.; $^1$H NMR (CDCl$_3$)ppm: 0.88 (3H, t), 1.08–1.96 (13H, m), 2.75–3.00 (2H, m), 2.90 (6H, m), 3.18 (2H, q), 3.30 (2H, t), 4.25 (1H, s), 4.59 (1H, bt), 6.74 (1H, d), 6.82 (1H, dd), 7.05–7.52 (10H, m), 7.90 (1H, d), 8.92 (1H, s).

EXAMPLE 101

2-(N'-Cyclobutylureido)-5-dimethylamino-N-[(1-diphenylmethylpiperidin-4-yl)methyl]benzamide {2-amino-5-dimethylamino-N-[(1-diphenylmethylpiperidin-4-yl)methyl]benzamide and cyclobutylamine}: mp 210°–212° C.; $^1$H NMR (CDCl$_3$) ppm: 1.30–1.90 (1H, m), 2.32 (2H, m), 2.89 (8H, s+m), 3.30 (2H, dd), 4.18 (1H, m), 4.26 (1H, s), 4.88 (1H, bs), 6.57 (1H, bs), 6.73 (1H, d), 6.81 (1H, d), 7.14–7.45 (10H, m), 7.89 (1H, d), 8.88 (1H, bs).

EXAMPLE 102

2-(N'-Cyclopentylureido)-5-dimethylamino-N-[(1-diphenylmethylpiperidin-4-yl)methyl]benzamide {2-amino-5-dimethylamino-N-[(1-diphenylmethylpiperidin-4-yl)methyl]benzamide and cyclopentylamine}: mp 211°–213° C.; $^1$H NMR (CDCl$_3$)ppm: 1.30–2.00 (15H, m), 2.90 (8H, s+m), 3.30 (2H, dd), 4.02 (1H, m), 4.24 (1H, s), 4.54 (1H, bs), 6.41 (1H, bs), 6.71 (1H, s), 6.83 (1H, d), 7.16–7.40 (10H, m), 7.94 (1H, d), 8.95 (1H, s).

EXAMPLE 103

2-(N'-3-Methoxypropylureido)-5dimethylamino-N-[(1-diphenylmethylpiperidin-4-yl)methyl]benzamide {2amino-5-dimethylamino-N-[(1-diphenylmethylpiperidin-4-yl)methyl]benzamide and 3-methoxypropylamine}: mp 191°–193° C.; $^1$H NMR (CDCl$_3$)ppm: 1.27–1.88 (9H, m), 2.92 (8H, m), 3.28 (7H, q+s), 3.41 (2H, t), 4.24 (1H, s), 4.88 (1H, bt), 6.60 (1H, bt), 6.77 (1H, dd), 6.81 (1H, dd), 7.13–7.40 (10H, m), 8.00 (1H, d), 8.64 (1H, bs).

EXAMPLE 104

2-(N'-3-Methoxypropylureido)-5-(morpholin-4-yl)-N-[(1-diphenylmethylpiperidin-4-yl)methyl] benzamide {2-amino-5-(morpholin-4-yl)-N-[(1-diphenylpiperidin-4-yl)methyl]benzamide and 3-methoxypropylamine}: mp 175°–176° C.; $^1$H NMR (CDCl$_3$)ppm: 1.34–1.88 (9H, m), 2.90 (2H, m), 3.06 (4H, m), 3.31 (7H, m+s), 3.44(2H, t), 3.84 (4H, m), 4.24 (1H, bt), 6.37 (1H, bt), 7.00 (1H, dd), 7.14–7.40 (10H, m), 8.10 (1H, d), 9.32 (1H, s).

EXAMPLE 105

2-(N'-Cyclopropylmethylureido)-5-(morpholin-4-yl)-N-[(1-diphenylmethylpiperidin-4-yl)methyl]benzamide {2-amino-5-(morpholin-4-yl)-N-[(1-diphenylmethylpiperidin-4-yl)-methyl]benzamide and cyclopropylmethylamine}: mp 218°–220° C.; $^1$H NMR (CDCl$_3$)ppm: 0.19 (2H, m), 0.48 (2H, m), 0.93 (1H, m), 1.34–1.88 (7H, m), 2.90 (2H, m), 3.06 (6H, m), 3.32 (2H, t), 3.84 (4H, m), 4.24 (1H, s), 4.69 (1H, bt), 6.34 (1H, bt), 6.89 (1H, d), 6.99 (1H, dd), 7.14–7.40 (10H, m), 8.15 (1H, d), 9.48 (1H, s).

The following compounds described in Examples 106 to 108 were prepared according to Example 26.

EXAMPLE 106

2-(N'-n-Heptylureido)-5-isopropyl-N-[(1-diphenylmethylpiperidin-4-yl)methyl]benzamide {2-amino-5-isopropyl-N-[(1-diphenylmethylpiperidin-4-yl)methyl]-benzamide and n-octanoic acid}: mp 179°–180.5° C.: $^1$H NMR (CDCl$_3$)ppm: 0.88 (3H, t), 1.22 (3H, d), 1.20–1.67 (13H, m), 1.69 (2H, d), 1.86 (2H, t), 2.84 (1H, m), 2.92 (2H, d), 3.23 (2H, dd), 3.32 (2H, t), 4.25 (1H, s), 4.53 (1H, t), 6.24 (1H, t), 7.14–7.42 (12H, m), 8.28 (1H, d), 10.03 (1H, s).

EXAMPLE 107

2-(N'-n-Heptylureido)-6-dimethylamino-N-(1-diphenylmethylpiperidin-4-yl)benzamide {2-amino-6-dimethylamino-N-(1-diphenylmethylpiperidin-4-yl)benzamide and n-octanoic acid}: mp 77° C.; $^1$H NMR (CDCl$_3$)ppm: 0.88 (3H, t), 1.10–1.30 (8H, m), 1.51 (2H, t), 1.61 (2H, m), 1.95 (2H, d), 2.13 (2H, t), 2.66 (6h, s), 2.76 (2H, d), 3.23 (2H, q), 3.97–4.05 (1H, m), 4.29 (1H, s), 4.52 (1H, bt), 6.74 (1H, d), 7.19 (1H, t), 7.26–7.43 (9H, m), 8.19 (1H, d), 9.83 (1H, bt), 11.10(1H,s).

EXAMPLE 108

2-(N'-n-Heptylureido)-4-dimethylamino-N-(1-diphenylmethylpiperidin-4-yl)benzamide {2-amino-4-dimethylamino-N-(1-diphenylmethylpiperidin-4-yl)benzamide and n-octanoic acid}: mp 87° C.; $^1$H NMR (CDCl$_3$)ppm: 0.87 (3H, t), 1.18–1.70 (12H, m), 1.96 (2H, d), 2.07 (2H, t), 2.83 (2H, d), 3.02 (6H, s), 3.24 (2H, q), 3.88–3.91 (1H, m), 4.27 (1H, s), 4.54 (1H, bt), 5.88 (1H, d), 6.23 (1H, dd), 7.10–7.51 (11H, m), 7.94 (1H, d), 11.01 (1H,s).

EXAMPLE 109

5-Amino-2-(N'-n-butylureido)-N-[(1-diphenylmethylpiperidin-4-yl)methyl]-benzamide Step 1): To a solution of 2amino-5nitro-N-[(1-diphenylmethylpiperidin-4-yl)methyl]benzamide (Preparation 28) (1.2 g, 2.69 mmol) in CHCl$_3$ (15 ml) was added n-butylisocyanate (802 mg, 8.09 mmol). After the solution was refluxed for 24 hours, the solvent was evaporated. The residue was purified by column chromatography on silica gel to give 5-nitro-2-(N'-n-butylureido)-N-[(1-diphenylmethylpiperidin-4-yl)methyl]benzamide, 1.1 g (75%).

Step 2): To a solution of 5-nitro-2-(N'-n-butylureido)-N-[(1-diphenylmethylpiperidin-4-yl)methyl]benzamide (960 mg, 1.76 mmol) in MeOH/AcOEt (50 ml/50 ml) was added PtO$_2$ (38 mg) and agitated under H$_2$ atmosphere (3 kg/cm$^2$) until the reaction was complete. The catalysts were filtered off and the filtrate was evaporated. The residue was purified by column chromatography on silica gel to give 5 amino-2-(N'-n-butylureido)-N-[(1-diphenylmethylpiperidin-4-yl) methyl]benzamide. 780 mg (86%): mp 212°–213° C.; $^1$H NMR (DMSO-d$_6$) ppm: 0.83 (3H, t), 1.21–1.88 (11H, m), 2.77 (2H, m), 2.95 (2H, q), 3.10 (2H, t), 4.27 (1H, s), 4.80 (2H, bs), 6.58 (1H, dd), 6.68 (1H, d), 6.75 (1H, bt), 7.13–7.41 (10H, m), 7.58 (1H, d), 8.35 (1H, bt), 8.74 (1H, s).

In a similar manner to that of Example 109, but replacing n-butylisocyanate with n-propylisocyanate, the following compound (Example 110) was prepared.

EXAMPLE 110

5-Amino-2-(N'-n-propylureido)-N-[(1-diphenylmethylpiperidin-4-yl)methyl]-benzamide {n-propylisocyanate}: mp 213°–214° C.; $^1$H NMR (DMSO-d$_6$) ppm: 0.80 (3H, t), 1.21–1.82 (9H, m), 2.77 (2H, m), 2.92 (2H, q), 3.10 (2H, m), 4.27 (1H, s), 4.80 (2H, bs), 6.58 (1H, dd), 6.68 (1H, d), 6.78 (1H, bt), 7.14–7.41 (10H, m), 7.59 (1H, d), 8.34 (1H, bt), 8.75 (1H, s).

EXAMPLE 111

(a) 2-N'-n-Butylureido)-5-methylsulfinyl-N-[(1-diphenylmethylpiperidin-4-yl)methyl]benzamide and (b) 2-(N'-n-butylureido)-5-methylsulfonyl-N-[(1-diphenylmethylpiperidin-4-yl)-methyl]benzamide A solution of 5-methylthio-2-(N'-n-butylureido)-N-[(1-diphenylme-thylpiperidin-4-yl)methyl]benzamide (EXAMPLE 73) (200 mg, 0.367 mmol) in CH$_3$CN/CH$_2$Cl$_2$/MeOH/H$_2$O (10 ml/2 ml/4 ml/0.5 ml) was agitated with OXONE® (2KHSO$_5$KHSO$_4$K$_2$SO$_4$) (142 mg, 0.231 mmol) for 2 hours at room temperature and then an additional OXONE® (15 mg) was added. The reaction mixture was made basic with 25% NH$_4$OH and diluted with CH$_2$Cl$_2$. The organic layer was washed twice with H$_2$O, dried over MgSO$_4$ and evaporated. The residue was purified by column chromatography on silica gel to give 2-(N'-n-butylureido)-5-methylsulfinyl-N-[(1-diphenylmethylpiperidin-4yl) methyl]benzamide. 130 mg (63%): mp 209°–211° C.; $^1$H NMR (CDCl$_3$) ppm: 0.91 (3H, t), 1.33–1.88 (11H, m), 2.69 (3H, s), 2.88 (2H, m), 3.22–3.31 (4H, m), 4.24 (1H, s), 4.85 (1H, bt), 7.03 (1H, bt), 7.13–7.42 (11H, m), 7.91 (1H, d), 8.63 (1H, d), 10.71 (1H, s); and 2-(N'-n-butylureido)-5-methylsulfonyl-N-[(1-diphenylmethylpiperidin-4-yl)-methyl]benzamide, 30 mg (14%): mp 178°–179° C.; $^1$H NMR (CDCl$_3$) ppm: 0.93(3H, t), 1.31–1.88 (11H, m), 2.90 (2.90 (2H, m), 3.02 (3H, s), 3.23–3.34 (4H, m), 4.25 (1H, s), 4.79 (1H, bt), 6.61 (1H, bt), 7.13–7.40 (10H, m), 7.89 (1H, dd), 7.97 (1H, d), 8.73 (1H, d), 10.82 (1H, s), respectively.

EXAMPLE 112

5-Methylamino-2-(N'-n-butylureido)-N-[(1-diphenylmethylpiperidin-4-yl)methyl]benzamide Step 1): A mixture of 2-amino-5-(N-tert-butoxycarbonyl-N-methyl)-amino-N-[(1-diphenylmethylpiperidin-4-yl) methyl]benzamide (Preparation 25) (1.4 g, 2.65 mmol) and n-butylisocyanate (1.4 g, 14.12 mmol) in CHCl$_3$ (25 ml) was refluxed for 8 hours and evaporated. The residue was purified by column chromatography on silica gel to give 5-(N-tert-butoxycarbonyl-N-methyl)amino-2-(N'-n-butylureido)-N-[(1-diphenylmethylpiperidin-4-yl)methyl] benzamide, 1.4 g (84%).

Step 2): A mixture of 5-(N-tert-butoxycarbonyl-N-methyl)amino-2-(N'-n-butylureido)-N-[(1- diphenylmethylpiperidin-4-yl)methyl]benzamide (1.4 g, 2.23 mmol) and trifluoroacetic acid (3 ml) was stirred under cooling in an ice-bath for 30 mins and at room temperature for 30 mins. The reaction mixture was poured into H$_2$O, made basic with NaHCO$_3$ and extracted with CHCl$_3$. The extract was washed with H$_2$O, dried over MgSO$_4$ and evaporated to give 5-methylamino-2-(N'-n-butylureido)-N-[(1-diphenylmethylpiperidin-4-yl)methyl]-benzamide, 310 mg (26.5%): mp 203°–204° C.; $^1$H NMR (CDCl$_3$) ppm: 0.90 (3H, t), 1.28–1.87 (12H, m), 2.79 (3H, s), 2.89 (2H, d), 3.17 (2H, q), 3.27 (2H, t), 4.23 (1H, s), 4.62 (1H, t), 6.56–6.67 (3H, m), 7.13–7.40 (10H, m), 7.82 (1H, d), 8.86 (1H, s).

The following Examples (Example 113 and 114) illustrate pharmaceutical compositions according to the present invention and an "active ingredient" in these Examples is any compound of the formula (1) as hereinabove defined, preferably one of the compounds of Examples 1 to 112.

EXAMPLE 113

Tablet formulation: Tablets each containing 100 mg of active ingredient, 200 mg of lactose, 40 mg of cellulose and 5 mg of magnesium stearate were prepared in accordance with usual procedure.

EXAMPLE 114

Capsule formulation: Hard-shell gelatin capsules each containing 50 mg of active ingredient, 100 mg of lactose, 30 mg of cornstarch and 2 mg of magnesium stearate were prepared in accordance with usual procedure.

We claim:

1. A 2-ureido-benzamide compound of the formula (1)

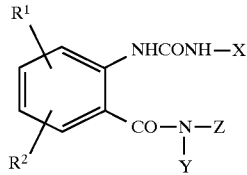

in which R$^1$ is H, halogen atom, (C$_1$–C$_4$)alkyl, (C$_1$–C$_4$) alkoxy or (C$_1$–C$_4$)dialkylamino and R$^2$ is H, halogen atom, hydroxy, nitro (C$_1$–C$_4$)alkyl, (C$_1$–C$_4$)alkoxy, (C$_3$–C$_6$) cycloalkylmethoxy, (C$_1$–C$_4$) alkylthio, (C$_1$–C$_4$) alkylsulfinyl, (C$_1$–C$_4$)alkylsulfonyl or

wherein R$^3$ and R$^4$ are each independently H, (C$_1$–C$_4$)alkyl, (C$_1$–C$_4$)alkanoyl, (C$_1$–C$_4$) alkylsulfonyl or (C$_1$–C$_4$) alkylcarbamoyl, and wherein NR$^3$R$^4$ can form a pyrrolidine, piperidine, morpholine, imidazole, or pyrazole ring;

X is a (C$_3$–C$_{15}$)alkyl, (C$_3$–C$_6$) cycloalkyl, (C$_3$–C$_6$) cycloalkylmethyl, or ω-(C$_1$–C$_4$)alkoxy-(C$_1$–C$_4$) alkyl group; and Y is H or (C$_1$–C$_4$) alkyl and Z is

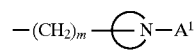

wherein m is an integer from 0 to 4,

is a pyrrolidinyl or piperidyl ring an A$^1$ is a benzyl, diphenylmethyl, dibenzoxepinyl, phenoxycarbonyl or biphenylmethyl group optionally carrying a halogen atom, hydroxy, (C$_1$–C$_7$)alkyl, or (C$_1$–C$_4$)alkoxy, and A$^2$ is a diphenylmethyl, or dibenzoxepinyl group optionally carrying a halogen atom; or —NYZ can form a ring

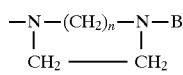

wherein n is an integer from 1 to 3 and B is a phenyl, diphenylmethyl or dibenzocycloheptenyl group optionally carrying halogen atom or (C$_1$–C$_4$)alkoxy; or a pharmaceutically acceptable acid-addition salt thereof.

2. A 2-ureido-benzamide compound according to claim 1 which is of the formula (1$_x$)

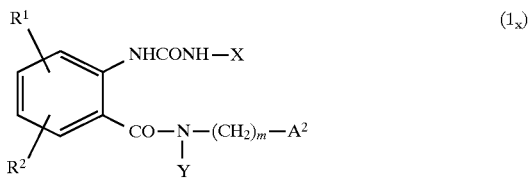

wherein R$^1$ is H; X is (C$_3$–C$_{10}$)alkyl; and Y is H; or a pharmaceutically acceptable acid-addition salt thereof.

3. A 2-ureido-benzamide compound according to claim 1 which is of the formula (1$_y$)

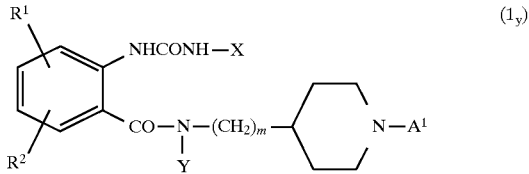

wherein R$^1$ is H; X is (C$_3$–C$_{10}$)alkyl; and Y is H; or a pharmaceutically acceptable acid-addition salt thereof.

4. A 2-ureido-benzamide compound according to claim 1 which is of the formula (1$_z$)

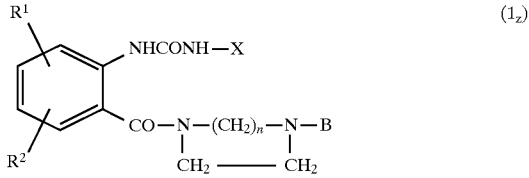

wherein R$^1$ is H and X is (C$_3$–C$_{10}$)alkyl; or a pharmaceutically acceptable acid-addition salt thereof.

5. A compound of claim 2 of the formula (1$_x$) wherein R$^2$ is H; X is (C$_3$–C$_8$)alkyl; m is 1 or 2; and A$^2$ is diphenylmethyl or dibenzoxepinyl; or a pharmaceutically acceptable acid-addition salt thereof.

6. A compound of claim 3 of the formula (1$_y$) wherein R$^2$ is H, di(C$_1$–C$_4$)alkylamino or morpholinyl; X is (C$_3$–C$_8$) alkyl; m is 0, 1 or 2; and A$^1$ is diphenylmethyl optionally carrying a halogen atom or (C$_1$–C$_4$)alkoxy on the phenyl ring or phenoxycarbonyl; or a pharmaceutically acceptable acid-addition salt thereof.

7. A compound of claim 4 of the formula (1$_z$) wherein R$^2$ is H; n is 2 or 3; and B is diphenylmethyl or dibenzocycloheptenyl; or a pharmaceutically acceptable acid-addition salt thereof.

8. A 2-ureido-benzamide compound selected from the group consisting of
2-(N'-n-heptylureido)-5-dimethylamino-N-[(1-diphenylmethylpiperidin-4-yl)-methyl]benzamide;
2-(N'-n-butylureido)-N-[(1-diphenylmethylpiperidin-4-yl)methyl]benzamide;
2-(N'-n-pentylureido)-N-[(1-diphenylmethylpiperidin-4-yl)methyl]benzamide;
2-(N'-n-hexylureido)-N-[(1-diphenylmethylpiperidin-4 -yl)methyl]benzamide;
2-(N'-n-heptylureido)-N-[(1-diphenylmethylpiperidin-4-yl)methyl]benzamide;
2-(N'-n-octylureido)-N-[(1-diphenylmethylpiperidin-4-yl)methyl]benzamide;
2-(N'-n-butylureido)-N-(1-diphenylmethylpiperidin-4-yl)benzamide;
2-(N'-n-hexylureido)-N-(1-diphenylmethylpiperidin-4-yl)benzamide;
2-(N'-n-octylureido)-N-(1-diphenylmethylpiperidin-4-yl)benzamide;
2-(N'-n-decylureido)-N-(1-diphenylmethylpiperidin-4-yl)benzamide;
2-(N'-n-heptylureido)-N-(1-phenoxycarbonylpiperidin-4-yl)benzamide;
2-(N'-n-heptylureido)-5-hydroxy-N-(3,3-diphenylpropyl)benzamide;
2-(N'-n-heptylureido)-N-[2-(1-diphenylmethylpiperidin-4-yl)ethyl]benzamide;
2-(N'-n-pentylureido)-N-[2-(1-diphenylmethylpiperidin-4-yl)ethyl]benzamide;
2-(N'-n-hexylureido)-N-[2-(1-diphenylmethylpiperidin-4-yl)ethyl]benzamide;
2-(N'-n-heptylureido)-5-dimethylamino-N-(1-diphenylmethylpiperidin-4-yl)-benzamide;
1-[2-(N'-n-heptylureido)benzoyl]-4-diphenylmethylhomopiperazine;
1-[2-(N'-n-heptylureido)benzoyl]-4-(10,11-dihydro-5H-dibenzo[a,b]cyclohepten-5-yl)-piperazine;
2-(N'-n-heptylureido)-N-(1-diphenylmethylpiperidin-4-yl)benzamide;
N-(2-bromo-6,11-dihydrodibenz[b,e]oxepin-11-yl)methyl-2-(N'-n-heptylureido)benzamide;
2-(N'-n-heptylureido)-5-acetoamido-N-(1-diphenylmethylpiperidin-4-yl)benzamide;
N-(3,3-diphenylpropyl)-2(N'-n-heptylureido)benzamide;
1-[2-(N'-n-heptylureido)benzoyl]-4-diphenylmethylpiperazine;
2-(N'-n-butylureido)-5-diethylamino-N-[(1-diphenylmethylpiperidin-4-yl)methyl]benzamide;
2-(N'-n-butylureido)-5-dimethylamino-N-[(1-diphenylmethylpiperidin-4-yl)methyl]benzamide;
2-(N'-n-butylureido)-5-(pyrrolidin-1-yl)-N-[(1-diphenylmethylpiperidin-4-yl)methyl]benzamide;
5-dimethylamino-2-(N'-n-propylureido)-N-[(1-diphenylmethylpiperidin-4-yl)methyl]benzamide;
2-(N'-n-butylureido)-5-methoxy-N-[(1-diphenylmethylpiperidin-4-yl)methyl]benzamide;
2-(N'-n-butylureido)-5-ethoxy-N-[(1-diphenylmethylpiperidin-4-yl)methyl]benzamide;
2-(N'-n-butylureido)-5-cyclopropylmethoxy-N-[(1-diphenylmethylpiperidin-4-yl)methyl]benzamide;
2-(N'-n-butylureido)-5-(morpholin-4-yl)-N-[(1-diphenylmethylpiperidin-4-yl)methyl]benzamide;
5-(morpholin-4-yl)-2-(N'-n-propylureido)-N-[(1-diphenylmethylpiperidin-4-yl)methyl]benzamide;
2-(N'-n-butylureido)-5-methylthio-N-[(1-diphenylmethylpiperidin-4-yl)methyl]benzamide;
5-n-butylcarbamyloxy-2-(N'-n-butylureido)-N-[(1-diphenylmethylpiperidin-4-yl)methyl]benzamide;
2-(N'-n-heptylureido)-5-methoxy-N-[(1-diphenylmethylpiperidin-4-yl)methyl]benzamide;
2-(N'-n-heptylureido)-5-(morpholin-4-yl)-N-[(1-diphenylmethylpiperidin-4-yl)methyl]benzamide;
2-(N'-n-heptylureido)-5-(pyrazol-1-yl)-N-[(1-diphenylmethylpiperidin-4-yl)methyl]benzamide;
2-(N'-n-heptylureido)-5-(pyrrolidin-1-yl)-N-[(1-diphenylmethylpiperidin-4-yl)methyl]benzamide;
5-ethoxy-2-(N'-n-heptylureido)-N-[(1-diphenylmethylpiperidin-4-yl)methyl]benzamide;
2-(N'-n-heptylureido)-5-dimethylamino-N-[(1-diphenylmethylpiperidin-3-yl)methyl]benzamide;
5-(N-acetyl-N-methyl)amino-2-(N'-n-heptylureido)-N-[(1-diphenylmethylpiperidin-4-yl)methyl]benzamide;
2-(N'-n-heptylureido)-5-dimethylamino-N-[[1-bis(4-fluorophenyl)methylpiperidin-4-yl]methyl]benzamide;
2-(N'-n-heptylureido)-5-dimethylamino-N-[[1-bis(4-methoxyphenyl)methylpiperidin-4-yl]-methyl]benzamide;
2-(N'-n-heptylureido)-5-dimethylamino-N-[1-(2biphenylmethylpiperidin-4-yl)-methyl]benzamide;
5-dimethylamino-2-(N'-n-pentylureido)-N-[(1-diphenylmethylpiperidin-4-yl)methyl]benzamide;
2-(N'-3-methoxypropylureido)-5-dimethylamino-N-[(1-diphenylmethylpiperidin-4-yl)-methyl]benzamide;
2-(N'-3-methoxypropylureido)-5-(morpholin-4-yl)-N-[(1-diphenylmethylpiperidin-4-yl)methyl]benzamide;
2-(N'-cyclopropylmethylureido)-5-(morpholin-4-yl)-N-[(1-diphenylmethylpiperidin-4-yl)-methyl]benzamide;
2-(N'-n-butylureido)-5-methylsulfinyl-N-[(1-diphenylmethylpiperidin-4-yl)methyl]benzamide;
2-(N'-n-butylureido)-5-methylsulfonyl-N-[(1-diphenylmethylpiperidin-4-yl)methyl]-benzamide; and
pharmaceutically acceptable acid-addition salts thereof.

9. A method for inhibiting acyl-CoA:cholesterol acyltransferase in a mammal, the method comprising: administering to the mammal a pharmaceutically effective amount of a 2-ureido-benzamide compound or a pharmaceutically acceptable acid-addition salt thereof as claimed in claim 1 in order to inhibit acyl-CoA:cholesterol acyltransferase.

10. A method for inhibiting macrophagic acyl-CoA:cholesterol acyltransferase in a mammal, the method comprising: administering to the mammal a pharmaceutically effective amount of a 2-ureido-benzamide compound or a pharmaceutically acceptable acid-addition salt thereof as claimed in claim 1 in order to inhibit macrophagic acyl-CoA:cholesterol acyltransferase.

11. A method for inhibiting accumulation of cholesterol ester in an arterial wall of mammal, the method comprising: administering to the mammal a pharmaceutically effective amount of a 2-ureido-benzamide compound or a pharmaceutically acceptable acid-addition salt thereof as claimed in claim 1 in order to inhibit accumulation of cholesterol ester in an arterial wall.

12. A method of treatment of disorders or diseases associated with acyl-CoA:cholesterol acyltransferase, the method comprising administering to a patient in need of the treatment a pharmaceutically effective amount of a 2-ureido-benzamide compound or a pharmaceutically acceptable acid-addition salt thereof as claimed in claim 1.

13. A method of treatment according to claim 12 wherein the disorder or disease associated with acyl-CoA: cholesterol acyltransferase is atherosclerosis.

14. A 2-ureido-benzamide compound selected from the group consisting of:
2-(N'-n-Heptylureido)-5-dimethylamino-N-[(1-diphenylmethylpiperidin-4-yl)methyl]benzamide;

2-(N'-n-Butylureido)-N-[(1-diphenylmethylpiperidin-4-yl)methyl]benzamide;
2-(N'-n-Pentylureido)-N-[(1-diphenylmethylpiperidin-4-yl)methyl]benzamide;
2-(N'-n-Hexylureido)-N-[(1-diphenylmethylpiperidin-4-yl)methyl]benzamide;
2-(N'-n-Heptylureido)-N-[(1-diphenylmethylpiperidin-4-yl)methyl]benzamide;
2-(N'-n-Octylureido)-N-[(1-diphenylmethylpiperidin-4-yl)methyl]benzamide;
2-(N'-n-Butylureido)-N-(1-diphenylmethylpiperidin-4-yl)benzamide;
2-(N'-n-Pentylureido)-N-(1-diphenylmethylpiperidin-4-yl)benzamide;
2-(N'-n-Hexylureido)-N-(1-diphenylmethylpiperidin-4-yl)benzamide;
2-(N'-n-Octylureido)-N-(1-diphenylmethylpiperidin-4-yl)benzamide;
2-(N'-n-Nonylureido)-N-(1-diphenylmethylpiperidin-4-yl)benzamide;
2-(N'-n-Decylureido)-N-(1-diphenylmethylpiperidin-4-yl)benzamide;
3;5-Dimethoxy-2-(N'-n-heptylureido)-N-(1-diphenylmethylpiperidin-4-yl) benzamide;
5-Fluoro-2-(N'-n-heptylureido)-N-(1-diphenylmethylpiperidin-4-yl) benzamide;
2-(N'-n-Heptylureido)-3-isopropyl-N-(1-diphenylmethylpiperidin-4-yl) benzamide;
2-(N'-n-Heptylureido)-5-nitro-N-(1-diphenylmethylpiperidin-4-yl)benzamide;
2-(N'-n-Heptylureido)-N-[3-(1-diphenylmethylpiperidin-3-yl)propyl]benzamide;
2-(N'-n-Heptylureido)-N-(2,6-diisopropylphenyl)benzamide;
2-(N'-n-Heptylureido)-5-hydroxy-N-(3,3-diphenylpropyl)benzamide;
2-[N'-(2-t-Butoxycarbonylaminoethyl)ureido]-N-(1-diphenylmethylpiperidin-4-yl)-benzamide;
1-[2-(N'-n-Heptylureido)benzoyl]-4-(2-methoxyphenyl)piperazine;
1-[2-(N'-n-Heptylureido)benzoyl]-4-diphenylmethylpiperazine;
2-[N'-(2Aminoethyl)ureido]-N-(1-diphenylmethylpiperidin-4-yl)benzamide;
2-[N'-(2-Aminoethyl)ureido]-N-[(1-diphenylmethylpiperidin-4-yl)methyl]-benzamide;
2-(N'-n-Heptylureido)-N-(1-phenoxycarbonylpiperidin-4-yl)benzamide
2-(N'-n-Heptylureido)-N-[2-(1-diphenylmethylpiperidin-4-yl)ethyl]benzamide;
2-(N'-n-Pentylureido)-N-[2-(1-diphenylmethylpiperidin-4-yl)ethyl]benzamide;
2-(N'-n-Hexylureido)-N-[2-(1-diphenylmethylpiperidin-4-yl)ethyl]benzamide;
2-(N'-n-Heptylureido)-5-dimethylamino-N-(1-diphenylmethylpiperidin-4-yl)benzamide;
2-(N'-n-Heptylureido)-3-dimethylamino-N-(1-diphenylmethylpiperidin-4-yl)benzamide;
2-(N'-n-Heptylureido)-N-methyl-N-[(1-diphenylmethylpiperidin-4-yl)methyl]-benzamide;
2-(N'-(1;1-Dimethyltridecyl)ureido)-N-(1-diphenylmethylpiperidin-4-yl)benzamide;
1-[2-(N'-n-Heptylureido)benzoyl]-4-diphenylmethylhomopiperazine;
1-[2-(N'-n-Heptylureido)benzoyl]-4-(10,11-dihydro-5H-debenzo[a,d]cyclohepten-5-yl)piperazine;
2-(N'-n-Heptylureido)-N-[3-(1-diphenylmethylpiperidin-4-yl)propyl]benzamide;
N-(1-Benzylpiperidin-4-yl)-2-(N'-n-Heptylureido)benzamide;
N-(1-Benzylpiperidin-4-yl)-2-(N'-n-Octylureido)benzamide;
2-(N'-n-Heptylureido)-N-(1-diphenylmethylpiperidin-4-yl)benzamide;
N-(3,5-Di-t-butyl-4-hydroxyphenyl)-2-(N'-n-heptylureido)benzamide;
N-(4-n-Heptylphenyl)-2-(N'-n-heptylureido)benzamide;
N-(2-Bromo-6,11-dihydrodibenz[b,e]oxepin-11-yl)methyl-2-(N'-n-heptylureido)benzamide;
N-(3,3-Diphenylpropyl)-2-(N'-n-heptylureido)benzamide;
N-[1-(2-Bromo-6,11-dihydrodibenz[b,e]oxepin-11-yl)piperidin-4-yl]-2-(N'-n-heptylureido)benzamide;
2-(N'-n-Heptylureido)-N-(1-diphenylmethylpiperidin-3-yl)benzamide
2-(N'-n-Heptylureido)-5-amino-N-(1-diphenylmethylpiperidin-4-yl)benzamide;
2-(N'-n-Heptylureido)-5-methylsulfonylamino-N-(1-diphenylmethylpiperidin-4-yl)benzamide;
2-(N'-n-Heptylureido)-5-acetylamino-N-(1-diphenylmethylpiperidin-4-yl)benzamide;
2-(N'-n-Heptylureido)-5-(N'-n-butylureido)-N-(1-diphenylmethylpiperidin-4-yl)benzamide;
2-[N'-(2-Di-n-butylaminoethyl)ureido]-N-(1-diphenylmethylpiperidin-4-yl)benzamide;
2-[N'-(2-n-Butylaminoethyl)ureido]-N-[(1-diphenylmethylpiperidin-4-yl)methyl]benzamide;
2-[N'-(2-Isopropylaminoethyl)ureido]-N-[(1-diphenylmethylpiperidin-4-yl)methyl]-benzamide;
2-(N'-n-Butylureido)-5-diethylamino-N-[(1-diphenylmethylpiperidin-4-yl]-benzamide;
2-(N'-n-Butylureido)-5-dimethylamino-N-[(1-diphenylmethylpiperidin-4-yl)methyl]-benzamide;
2-(N'-n-Butylureido)-5-(imidazol-1yl)-N-[(1-diphenylmethylpiperidin-4-yl)methyl]-benzamide;
2-(N'-n-Butylureido)-5-(pyrrolidin-1-yl)-N-[(1-diphenylmethylpiperidin-4-yl)methyl]-benzamide;
5-Dimethyl-2-(N'-n-propylureido)-N-[(1-diphenylmethylpiperidin-4-yl)methyl]-benzamide;
2-(N'-n-Butylureido)-5-methoxy-N-[(1-diphenylmethylpiperidin-4-yl)methyl]benzamide;
2-(N'-n-Butylureido)-5-ethoxy-N-[(1-diphenylmethylpiperidin-4-yl)methyl]-benzamide;
2-(N'-n-Butylureido)-5-cyclopropylmethoxy-N-[(1-diphenylmethylpiperidin-4-yl)methyl]-benzamide;
2-(N'-n-Butylureido)-5-(morpholin-4-yl)-N-[(1-diphenylmethylpiperidin-4-yl)methyl]-benzamide;
5-(Morpholin-4-yl)-2-(N'-n-propylureido)-N-[(1-diphenylmethylpiperidin-4-yl)methyl]-benzamide;
5-Methylthio-2-(N'-n-propylureido)-N-[(1-diphenylmethylpiperidin-4-yl)methyl]benzamide;
2-(N'-n-Butylureido)-5-methylthio-N-[(1-diphenylmethylpiperidin-4-yl)methyl]benzamide;
2-(N'-n-Butylureido)-5-ethylthio-N-[(1-diphenylmethylpiperidin-4-yl)methyl]-benzamide;
2-(N'-n-Butylureido)-5-(di-n-propyl)amino-N-[(1-diphenylmethylpiperidin-4-yl)methyl]-benzamide;
5-(di-n-Butyl)amino-2-(N'-n-butylureido)-N-[(1-diphenylmethylpiperidin-4-yl)methyl]-benzamide;
2-(N'-n-Butylureido)-5-hydroxy-N-[(1-diphenylmethylpiperidin-4-yl)methyl]benzamide; and
5-n-butylcarbamyloxy-2-(N'-n-butylureido)-N-[(1-diphenylmethylpiperidin-4-yl)methyl]benzamide;
2-(N'-n-Butylureido)-4-chloro-N-[(1-diphenylmethylpiperidin-4-yl)methyl]-benzamide;
2-(N'-n-Heptylureido)-5-(imiadazol-1-yl)-N-[(1-diphenylmethylpiperidin-4-yl)methyl]-benzamide;

2-(N'-n-Decylureido)-5-dimethylamino-N-[(1-diphenylmethylpiperidin-4-yl)methyl]-benzamide;

2-(N'-n-Heptylureido)-5-methoxy-N-[(1-diphenylmethylpiperidin-4-yl)methyl]benzamide;

2-(N'-n-Heptylureido)-5-(morpholin-4-yl)-N-[(1-diphenylmethylpiperidin-4-yl)methyl]-benzamide;

2-(N'-n-Heptylureido)-5-(piperidin-1-yl)-N-[(1-diphenylmethylpiperidin-4-yl)methyl]benzamide;

2-(N'-n-Heptylureido)-5-(pyrazol-1-yl)-N-[(1-diphenylmethylpiperidin-4-yl)-methyl]-benzamide;

2-(N'-n-Heptylureido)-5-(pyrrolidin-1-yl)-N-[(1-diphenylmethylpiperidin-4-yl)methyl]-benzamide;

5-Ethoxy-2-(N'-n-heptylureido)-N-[(1-diphenylmethylpiperidin-4-yl)methyl]-benzamide;

5-Diethylamino-2-(N'-n-heptylureido)-N-[(1-diphenylmethylpiperidin-4 -yl)methyl]-benzamide;

2-(N'-n-Heptylureido)-5-N-[(1-diphenylmethylpiperidin-3-yl)methyl]-benzamide;

2-(N'-n-Heptylureido)-5-hydroxy-N-[(1-diphenylmethylpiperidin-4 -yl)methyl]-benzamide;

5-(N-Acetyl-N-methyl)amino-2-(N'-n-Heptylureido)-N-[(1-diphenylmethylpiperidin-4 -yl)methyl]-benzamide;

2-(N'-n-Heptylureido)-5-dimethylamino-N-[[1-bis(4-chlorophenyl)methylpiperidin-4-yl]-methyl]-benzamide;

2-(N'-n-Heptylureido)-5-dimethylamino-N-[[(1-bis(4-fluorophenyl)methylpiperidin-4 -yl]-methyl]benzamide;

2-(N'-n-Heptylureido)-5-dimethylamino-N-[[(1-bis(4-methoxyphenyl)methylpiperidin-4-yl]methyl]-benzamide;

2-(N'-n-Heptylureido)-5-dimethylamino-N-[1-(4-biphenylmethylpiperidin-4 -yl)methyl]-benzamide;

2-(N'-n-Heptylureido)-5-dimethylamino-N-[1-(2-biphenylmethylpiperidin-4 -yl)methyl]-benzamide;

2-(N'-n-Heptylureido)-5-dimethylamino-N-[1-methyl-1-(1diphenylmethylpiperidin-4-yl)-ethyl]-benzamide;

5-Dimethylamino-2-(N'-n-pentylureido)-N-[(1-diphenylmethylpiperidin-4 -yl)methyl]-benzamide;

2-(N'-Cyclobutylureido)-5-dimethylamino-N-[(1-diphenylmethylpiperidin-4 -yl)methyl]-benzamide;

2-(N'Cyclopentylureido)-5-dimethylamino-N-[(1-diphenylmethylpiperidin-4 -yl)methyl]benzamide;

2-(N'-3-Methoxypropylureido)-5-dimethylamino-N-[(1-diphenylmethylpiperidin-4 -yl)methyl]benzamide;

2-(N'-3-Methoxypropylureido)-5-(morpholin-4yl)-N-[(1-diphenylmethylpiperidin-4 -yl)methyl]benzamide;

2-(N'-Cyclopropylmethylureido)-5-(morpholin-4-yl)-N-[(1-diphenylmethylpiperidin-4 -yl)methyl]benzamide;

2-(N'-n-Heptylureido)-5-isopropyl-N-[(1-diphenylmethylpiperidin-4 -yl)methyl]-benzamide;

2-(N'-n-Heptylureido)-6-dimethylamino-N-(1-diphenylmethylpiperidin-4-yl)benzamide;

2-(N'-n-Heptylureido)-4-dimethylamino-N-(1-diphenylmethylpiperidin-4-yl)benzamide;

5-Amino-2-(N'-n-butylureido)-N-[(1-diphenylmethylpiperidin-4-yl]-benzamide;

5-Amino-2-(N'-n-propylureido)-N-[(1-diphenylmethylpiperidin-4-yl)methyl]-benzamide;

2-(N'-n-Butylureido)-5-methylsulfinyl-N-[(1-diphenylmethylpiperidin-4-yl)methyl]-benzamide;

2-(N'-n-butylureido)-5-methylsulfonyl-N-[(1-diphenylmethylpiperidin-4-yl)-methyl(]benzamide;

5-Methylamino-2-(N'-n-butylureido)-N-[(1-diphenylmethylpiperidin-4-yl)methyl]benzamide; and pharmaceutically acceptable acid-addition salts thereof.

15. A 2-ureido-benzamide compound as claimed in claim 14, wherein the compound is selected from the group consisting of:

5-Dimethylamino-2-(N'-n-propylureido)-N-[(1-diphenylmethylpiperidin-4-yl)methyl]-benzamide;

2-(N'-n-Butylureido)-5-dimethylamino-N-[(1-diphenylmethylpiperidin-4-yl)methyl]-benzamide;

5-(Morpholin-4-yl)-2-(N'-n-propylureido)-N-[(1-diphenylmethylpiperidin-4-yl)methyl]-benzamide; and pharmaceutically acceptable acid-addition salts thereof.

16. A pharmaceutical composition comprising: (1) a pharmaceutically acceptable amount of a 2-ureido-benzamide compound or a pharmaceutically acceptable acid-addition salt thereof as claimed in claim 1, and (2) a pharmaceutically acceptable carrier, excipient, or diluent.

17. A pharmaceutical composition comprising: (1) a pharmaceutically acceptable amount of a 2-ureido-benzamide compound or a pharmaceutically acceptable acid-addition salt thereof as claimed in claim 8; and (2) a pharmaceutically acceptable carrier, excipient, or diluent.

18. A pharmaceutical composition comprising: (1) a pharmaceutically acceptable amount of a 2-ureido-benzamide compound or a pharmaceutically acceptable acid-addition salt thereof as claimed in claim 14; and (2) a pharmaceutically acceptable carrier, excipient, or diluent.

19. A pharmaceutical composition comprising: (1) a pharmaceutically acceptable amount of a 2-ureido-benzamide compound or a pharmaceutically acceptable acid-addition salt thereof as claimed in claim 15; and (2) a pharmaceutically acceptable carrier, excipient, or diluent.

20. A method for treating or preventing hypercholesterolemia, atherosclerosis, ischemic heart disease, or cerebrovascular disease in a mammal, the method comprising: administering to the mammal a pharmaceutically effective amount of a 2-ureido-benzamide compound or a pharmaceutically acceptable acid-addition salt thereof as claimed in claim 1 in order to treat or prevent the hypercholesterolemia, atherosclerosis, ischemic heart disease, or cerebrovascular disease.

21. A method for treating or preventing hypercholesterolemia, atherosclerosis, ischemic heart disease, or cerebrovascular disease in a mammal, the method comprising: administering to the mammal a pharmaceutically effective amount of a 2-ureido-benzamide compound or a pharmaceutically acceptable acid-addition salt thereof as claimed in claim 8 in order to treat or prevent the hypercholesterolemia, atherosclerosis, ischemic heart disease, or cerebrovascular disease.

22. A method for treating or preventing hypercholesterolemia, atherosclerosis, ischemic heart disease, or cerebrovascular disease in a mammal, the method comprising: administering to the mammal a pharmaceutically effective amount of a 2-ureido-benzamide compound or a pharmaceutically acceptable acid-addition salt thereof as claimed in claim 14 in order to treat or prevent the hypercholesterolemia, athersclerosis, ischemic heart disease, or cerebrovascular disease.

23. A method as claimed in claim 20, wherein the effective amount of the 2-ureido-benzamide compound or the pharmaceutically acceptable acid-addition salt thereof is 10 μg to 100 mg per kilogram of body weight of the mammal.

24. A pharmaceutical composition as claimed in claim 16, wherein the pharmaceutically acceptable amount of the 2-ureido-benzamide compound or the pharmaceutically acceptable acid-addition salt thereof is 10 μg to 100 mg.

25. A 2-ureido-benzamide compound or a pharmaceutically acceptable acid-addition salt thereof as claimed in claim 3, wherein $R^2$ is H, halogen atom, hydroxy, nitro, $(C_1–C_4)$alkyl, $(C_1–C_4)$alkoxy, $(C_3–C_6)$ cycloalkylmethoxy, $(C_1–C_4)$ alkylthio, $(C_1–C_4)$ alkylsulfinyl, or $(C_1–C_4)$ alkylsulfonyl.

26. A 2-ureido-benzamide compound or a pharmaceutically acceptable acid-addition salt thereof as claimed in claim 7, wherein B is diphenylmethyl.

* * * * *